(12) United States Patent
Sung et al.

(10) Patent No.: US 8,771,667 B2
(45) Date of Patent: Jul. 8, 2014

(54) TCTEX-1 REGULATORY SEQUENCE AS STEM CELL MARKER

(75) Inventors: Ching-Hwa Sung, New York, NY (US); Jen-Zen Chuang, New York, NY (US)

(73) Assignee: Cornell University, Ithaca, NY (US)

( * ) Notice: Subject to any disclaimer, the term of this patent is extended or adjusted under 35 U.S.C. 154(b) by 14 days.

(21) Appl. No.: 13/496,974

(22) PCT Filed: Sep. 20, 2010

(86) PCT No.: PCT/US2010/049496
§ 371 (c)(1),
(2), (4) Date: Mar. 19, 2012

(87) PCT Pub. No.: WO2011/035244
PCT Pub. Date: Mar. 24, 2011

(65) Prior Publication Data
US 2012/0183512 A1    Jul. 19, 2012

Related U.S. Application Data

(60) Provisional application No. 61/243,841, filed on Sep. 18, 2009.

(51) Int. Cl.
*A61K 35/00* (2006.01)
*C12N 15/85* (2006.01)

(52) U.S. Cl.
USPC ........................................ 424/93.1; 435/325

(58) Field of Classification Search
USPC ........................................ 424/93.1; 435/325
See application file for complete search history.

(56) References Cited

FOREIGN PATENT DOCUMENTS

WO    2007-005733    1/2007

OTHER PUBLICATIONS

Altman, J. et al., "Autoradiographic and histological evidence of postnatal hippocampal neurogenesis in rats" J Comp Neurol (1965) pp. 319-335, vol. 124.
Barker, N. et al., "Identification of stem cells in small intestine and colon by marker gene Lgr5" Nature (Oct. 25, 2007) pp. 1003-1007, vol. 449, No. 7165.
Barker, N. et al., "Crypt stem cells as the cells-of-origin of intestinal cancer" Nature (Jan. 29, 2009) pp. 608-611, vol. 457, No. 7229.
Brazel, C.Y. et al., "Sox2 expression defines a heterogeneous population of neurosphere-forming cells in the adult murine brain" Aging Cell (May 16, 2005) pp. 197-207, vol. 4, No. 4.
Cameron, H. A. et al., "Differentiation of newly born neurons and glia in the dentate gyrus of the adult rat" Neuroscience (1993) pp. 337-344, vol. 56, No. 2.
Chuang, J. Z. et al., "Subunit heterogeneity of cytoplasmic dynein: Differential expression of 14 kDa dynein light chains in rat hippocampus" The Journal of Neuroscience (Aug. 1, 2001) pp. 5501-5512, vol. 21, No. 15.
Chuang, J.Z. et al., "The dynein light chain Tctex-1 has a dynein-independent role in actin remodeling during neurite outgrowth" Developmental Cell (Jul. 2005) pp. 75-86, vol. 9.
Couillard-Despres, S. et al., "Targeted transgene expression in neuronal precursors: watching young neurons in the old brain" European Journal of Neuroscience (2006) pp. 1535-1545, vol. 24, No. 6.
Dedesma, C. et al., "Dynein light chain Tctex-1 identifies neural progenitors in adult brain" The Journal of Comparative Neurology (2006) pp. 773-786, vol. 496, No. 6.
Duan, X. et al., "Development of neural stem cell in the adult brain" Current Opinion in Neurobiology (2008) pp. 108-115, vol. 18, No. 1.
Ehninger, D. et al., "Neurogenesis in the adult hippocampus" Cell Tissue Res (2008) pp. 243-250, vol. 331, No. 1.
Englund, C. et al., "Pax6, Tbr2, and Tbr1 are expressed sequentially by radial glia, intermediate progenitor cells, and postmitotic neurons in developing neocortex" The Journal of Neuroscience (Jan. 5, 2005) pp. 247-251, vol. 25, No. 1.
Eriksson, P. S. et al., "Neurogenesis in the adult human hippocampus" Nature Medicine (Nov. 1998) pp. 1313-1317, vol. 4, No. 11.
Ever, L. et al., "Radial 'glial' progenitors: neurogenesis and signaling" Current Opinion in Neurobiology (2005) pp. 29-33, vol. 15, No. 1.
Filippov, V. et al., "Subpopulation of nestin-expressing progenitor cells in the adult murine hippocampus shows electrophysiological and morphological characteristics of astrocytes" Molecular and Cellular Neuroscience (2003) pp. 373-382, vol. 23, No. 3.
Fukuda, S. et al., "Two distinct subpopulations of nestin-positive cells in adult mouse dentate gyrus" The Journal of Neuroscience (Oct. 15, 2003) pp. 9357-9366, vol. 23, No. 28.
Gal, J. S. et al., "Molecular and morphological heterogeneity of neural precursors in the mouse neocortical proliferative zones" The Journal of Neuroscience (Jan. 17, 2006) pp. 1045-1056, vol. 26, No. 3.
Garcia, A. D. et al., "GFAP-expressing progenitors are the principal source of constitutive neurogenesis in adult mouse forebrain" Nature Neuroscience (Nov. 2004) pp. 1233-1241, vol. 7, No. 11.
Gotta, M. et al., "Asymmetrically distributed *C. elegans* homologs of AGS3/PINS control spindle position in the early embryo" Current Biology (Jun. 17, 2003) pp. 1029-1037, vol. 13, No. 12.
Gotz, M. et al., "Pax6 controls radial glia differentiation in the cerebral cortex" Neuron (Nov. 1998) pp. 1031-1044, vol. 21, No. 5.
Hastings, N. B. et al., "Rapid extension of axons into the CA3 region by adult-generated granule cells" The Journal of Comparative Neurology (1999) pp. 146-154, vol. 413, No. 1.

(Continued)

*Primary Examiner* — Marcia S Noble
*Assistant Examiner* — Magdalene Sgagias
(74) *Attorney, Agent, or Firm* — Scully, Scott, Murphy & Presser, P.C.

(57) ABSTRACT

The disclosure relates to an isolated regulatory sequence for Tctex-1 that is transcriptionally active in adult neural progenitor and stem cells, including Type 1, Type 2 and Type 3 progenitors, as well as during development. The disclosure also relates to a method for selectively expressing a genetic sequence in neural progenitor cells. The disclosure of inserting and expressing a specific sequence in these cells allows marking, identification, sorting, tracking, and manipulating neural progenitor and stem cells.

8 Claims, 14 Drawing Sheets

(56) References Cited

OTHER PUBLICATIONS

Hevner, R. F. et al., "Tbr1 regulates differentiation of the preplate and layer 6" Neuron (Feb. 2001) pp. 353-366, vol. 29, No. 2.

Hodge, R. D. et al., "Intermediate progenitors in adult hippocampal neurogenesis: Tbr2 expression and coordinate regulation of neuronal output" The Journal of Neuroscience (Apr. 2, 2008) pp. 3707-3717, vol. 28, No. 14.

Jessberger, S. et al., "Seizures induce proliferation and dispersion of doublecortin-positive hippocampal progenitor cells" Experimental Neurology (2005) pp. 342-351, vol. 196, No. 2.

Kempermann, G. et al., "Experience-induced neurogenesis in the senescent dentate gyrus" The Journal of Neuroscience (May 1, 1998) pp. 3206-3212, vol. 18, No. 9.

King, S. M. et al., "The mouse t-complex-encoded protein Tctex-1 is a light chain of brain cytoplasmic dynein" The Journal of Biological Chemistry (Dec. 13, 1996) pp. 32281-32287, vol. 271, No. 50.

Komitova, M. et al., "Sox-2 is expressed by neural progenitors and astroglia in the adult rat brain" Neuroscience Letters (2004) pp. 24-27, vol. 369, No. 1.

Kornack, D. R. et al., "Continuation of neurogenesis in the hippocampus of the adult macaque monkey" Proc Natl Acad Sci USA (May 1999) pp. 5768-5773, vol. 96, No. 10.

Kronenber, G. et al., "Subpopulations of proliferating cells of the adult hippocampus respond differently to physiologic neurogenic stimuli" The Journal of Comparative Neurology (2003) pp. 455-463, vol. 467.

Machado, R. D. et al., "Functional interaction between BMPR-II and Tctex-1, a light chain of Dynein, is isoform-specific and disrupted by mutations underlying primary pulmonary hypertension" Human Molecular Genetics (2003) pp. 3277-3286, vol. 12, No. 4.

Markakis, E. A. et al., "Adult-generated neurons in the dentate gyrus send axonal projections to field CA3 and are surrounded by synaptic vesicles" The Journal of Comparative Neurology (1999) pp. 449-460, vol. 406, No. 4.

Matsuda, T. et al., "Electroporation and RNA interference in the rodent retina in vivo and in vitro" Proc Natl Acad Sci USA (Jan. 6, 2004) pp. 16-22, vol. 101, No. 1.

Mignone, J.L. et al., "Neural stem and progenitor cells in nestin-GFP transgenic mice" The Journal of Comparative Neurology (2004) pp. 311-324, vol. 469, No. 3.

Mills, J.C. et al., "Molecular characterization of mouse gastric epithelial progenitor cells" PNAS (Nov. 12, 2002) pp. 14819-14824, vol. 99, No. 23.

Mueller, S. et al., "Interaction of the poliovirus receptor CD155 with the dynein light chain Tctex-1 and its implication for poliovirus pathogenesis" The Journal of Biological Chemistry (2002) pp. 7897-7904, vol. 277, No. 10.

Nadano, D. et al., "Human tastin, a proline-rich cytoplasmic protein, associates with the microtubular cytoskeleton" Biochem J. (2002) pp. 669-677, vol. 364, Pt. 3.

Nagano, F. et al., "Interaction of Doc2 with tctex-1, a light chain of cytoplasmic dynein: Implication in dynein-dependent vesicle transport" The Journal of Biological Chemistry (Nov. 13, 1998) pp. 30065-30068, vol. 273, No. 46.

Palmer, T. D. et al., "The adult rat hippocampus contains primordial neural stem cells" Molecular and Cellular Neuroscience (1997) pp. 389-404, vol. 8, No. 6.

Pfister, K. K. et al., "Cytoplasmic dynein nomenclature" The Journal of Cell Biology (Nov. 7, 2005) pp. 411-413, vol. 171, No. 3.

Roy, N. S. et al., "Promoter-targeted selection and isolation of neural progenitor cells from the adult human ventricular zone" Journal of Neuroscience Research (2000) pp. 321-331, vol. 59, No. 3.

Roy, N. S. et al., "In vitro neurogenesis by progenitor cells isolated from the adult human hippocampus" Nature Medicine (Mar. 2000) pp. 271-277, vol. 6, No. 3.

Sachdev, P. et al., "G protein beta gamma subunit interaction with the dynein light-chain component Tctex-1 regulates neurite outgrowth" The EMBO Journal (2007) pp. 2621-2632, vol. 26, No. 11.

Saito, T. et al., "Efficient gene transfer into the embryonic mouse brain using in vivo electroporation" Developmental Biology (2001) pp. 237-246, vol. 240, No. 1.

Sanada, K. et al., "G Protein betagamma Subunits and AGS3 Control Spindle Orientation and Asymmetric Cell Fate of Cerebral Cortical Progenitors" Cell (Jul. 15, 2005) pp. 119-131, vol. 122, No. 1.

Schaefer, M. et al., "Heterotrimeric G proteins direct two modes of asymmetric cell division in the *Drosophila* nervous system" Cell (Oct. 19, 2001) pp. 183-194, vol. 107, No. 2.

Schwarzer, C. et al., "Voltage-dependent anion-selective channel (VDAC) interacts with the dynein light chain Tctex1 and the heat-shock protein PBP74" The International Journal of Biochemistry & Cell Biology (2002) pp. 1059-1070, vol. 34, No. 9.

Seaberg, R. M. et al., "Adult rodent neurogenic regions: the ventricular subependyma contains neural stem cells, but the dentate gyrus contains restricted progenitors" The Journal of Neuroscience (Mar. 1, 2002) pp. 1784-1793, vol. 22, No. 5.

Seri, B. et al., "Cell types, lineage, and architecture of the germinal zone in the adult dentate gyrus" The Journal of Comparative Neurology (2004) pp. 359-378, vol. 478, No. 4.

Seri, B. et al., "Astrocytes give rise to new neurons in the adult mammalian hippocampus" The Journal of Neuroscience (Sep. 15, 2001) pp. 7153-7160, vol. 21, No. 18.

Steiner, B. et al., "Type-2 cells as link between glial and neuronal lineage in adult hippocampal neurogenesis" Glia (2006) pp. 805-814, vol. 54, No. 8.

Tabata, H. et al.,"Efficient in utero gene transfer system to the developing mouse brain using electroporation: visualizatin of neuronal migration in the developing cortex" Neuroscience (2001) pp. 865-872, vol. 103, No. 4.

Tai, A. W. et al., "Rhodopsin's carboxy-terminal cytoplasmic tail acts as a membrane receptor for cytoplasmic dynein by binding to the dynein light chain Tctex-1" Cell (Jun. 25, 1999) pp. 877-887, vol. 97.

Tai, A. W. et al., "Cytoplasmic dynein regulation by subunit heterogeneity and its role in apical transport" The Journal of Cell Biology (Jun. 25, 2001) pp. 1499-1509, vol. 153.

Takesono, A. et al., "Receptor-independent activators of heterotrimeric G-protein signaling pathways" The Journal of Biological Chemistry (1999) pp. 33202-33205, vol. 274, No. 47.

Van Praag, H. et al., "Functional neurogenesis in the adult hippocampus" Nature (Feb. 28, 2002) pp. 1030-1034, vol. 415, No. 6875.

Wang, S. et al., "Promoter-based isolation and fluorescence-activated sorting of mitotic neuronal progenitor cells from the adult mammalian ependymal/subependymal zone" Developmental Neuroscience (2000) pp. 167-176, vol. 22, No. 1-2.

Wang, S. et al., "Isolation of neuronal precursors by sorting embryonic forebrain transfected with GFP regulated by the T alpha 1 tubulin promoter" Nature Biotechnology (Feb. 1998) pp. 196-201, vol. 16, No. 2.

Wang, X. et al., "Rapid promoter analysis in developing mouse brain and genetic labeling of young neurons by doublecortin-DsRed-express" Journal of Neuroscience Research (2007) pp. 3567-3573, vol. 85, No. 16.

Xu, Y. et al., "Neurogenesis in the ependymal layer of the adult rat 3rd ventricle" Experimental Neurology (2005) pp. 251-264, vol. 192, No. 2.

Yamaguchi, M. et al., "Visualization of neurogenesis in the central nervous system using nestin promoter-GFP transgenic mice" Developemental Neuroscience Neuroreport (2000) pp. 1991-1996, vol. 11, No. 9.

Zhao, C. et al., "Mechanisms and functional implications of adult neurogenesis" Cell (Feb. 22, 2008) pp. 645-660, vol. 132, No. 4.

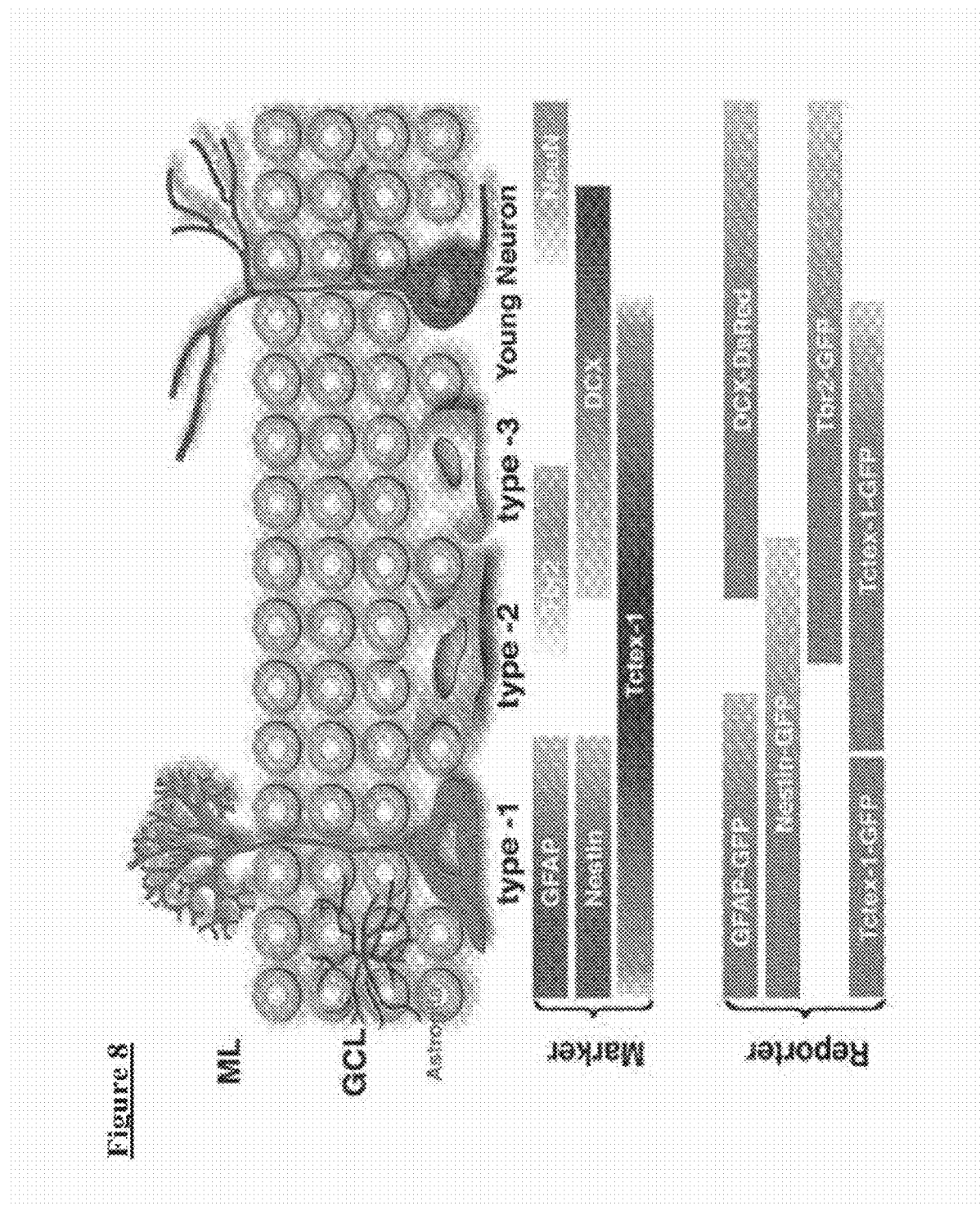

SEQUENCE LISTING

<160> NUMBER OF SEQ ID NOS: 11

<210> SEQ ID NO 1
<211> LENGTH: 10263
<212> TYPE: DNA
<213> ORGANISM: Homo sapiens

<400> SEQUENCE: 1

| | | | | | |
|---|---|---|---|---|---|
| ccctgctaca | ttttttgtaat | ggtgcctgtc | tttgttttac | agcactccat | cgatcagcct | 60 |
| gattttatct | ggcaattaaa | aatgaataaa | tcccacacca | cagcaccacc | tggaaggaaa | 120 |
| cattctccta | cagccatgtg | gagaagcccc | cccgacactc | agccatcctg | tctctgtgtc | 180 |
| acttttggag | ccagacagtc | tgggctcata | cccagccagg | actcagccac | gtgctctcag | 240 |
| gccagctgct | tcatctctgg | gagactggcc | ttcctcctcc | gtgacatgga | gccatccctg | 300 |
| cttcacaggg | ctgtttgggg | aactcactga | gtcatccagg | cacagcccta | gagcaacagc | 360 |
| cagaacaaag | caagcccgac | tcaaaagggt | ttcttctacc | cttccatctc | cccttcagga | 420 |
| aggcccaaga | gtaggaagtt | aagccactgt | tctgggattg | ggagggacgc | gggcagccat | 480 |
| ggggaaaact | tcaatctagg | tgtttccatt | ggtctttatc | tggtcatgct | gtatcccagt | 540 |
| ggaacttcgg | catccagaca | aacacagttt | ggttacggca | ttgagtgtgt | cagttcaaca | 600 |
| ctgattttat | tggcctctat | gtatcaagca | cgtgccagat | atcgaggatc | taaaaagaag | 660 |
| tgagactcaa | tctctgcatt | taagaaggac | ccatcccagc | cagaacatgg | acacacagac | 720 |
| aaataactca | taacatggtg | ggatgagtac | aaaacccaag | gatcagaagg | caagagtcac | 780 |
| tccacacagg | agcagagagg | gctggtggga | ccagggaggg | cttcccaggg | agagacgtgt | 840 |
| gggacagctc | cgccagggga | ctgaaatagt | cagccatgca | ctaggagttt | gaaacaatgc | 900 |
| ctgcttgctt | tcctcagcct | aacagcaaat | cttgactttg | gcttctaaat | ctggtgaaag | 960 |
| gggaaaagta | caagaaaagt | aaaaccaatg | aagaaaagag | atgaggagga | tgggaaaggg | 1020 |
| acacattgtt | tattcttagg | ggcccctatt | tctttcatcc | aatcatctat | tgtctctgag | 1080 |
| cagtcagtca | tcagatcaaa | ggaaataaat | gttcagccct | ccctggtacg | ggggaaacgt | 1140 |
| caccagagtg | gaaatgcaga | gatctgcggt | agcatgagtg | cgtgtgaatg | tgactgtcat | 1200 |
| caccacacac | gctttcaagg | gaagactaca | gaacgttctc | aaagcccaca | agccacagcc | 1260 |
| ctgcaggtca | tttcaagcgg | gcggcagctc | gctcctgtat | tgtttaccac | agctatttcc | 1320 |
| ttgagaagtt | tcacagcttc | agcgtgcagc | caccatgctt | tctgcctcgt | acacagggga | 1380 |
| aaagttgagt | gactgcattg | tccttgaaat | tttacctgaa | aacctcatga | cttttttgct | 1440 |
| tgcatagatt | cttttttttt | ttctctgaga | cggagttcgc | tcttgttgcc | caggcgggaa | 1500 |
| tgcaatggcg | cgatcttggc | tcaccacaac | ctccgcctcc | caggttcatg | aaattctcct | 1560 |
| gcctcaacct | cccgagtagc | tgacattaca | ggcatgcacc | accatcctcc | gctaattttg | 1620 |
| tattttagt | agagacaggg | tttcttcatg | ttggtcaggc | tggtctcaaa | ctcccaacct | 1680 |
| caggtgatct | gcccaccgtg | gcctcccaaa | gtgctgggat | tacaggtgtg | agccactgcg | 1740 |
| accggcctgc | ttgcatagat | tctttacgga | agctgattac | agccacaaag | gaaggtgatg | 1800 |
| aataaagaac | agctctcagc | tcagttccct | attcataggc | ttaaaagact | cattttttgca | 1860 |
| acaatgagac | agcacgcatg | catatccatc | agaaagtctg | acacagaaat | gaagatgtgc | 1920 |
| gtttatacat | tttctgtcta | tcttgttact | cattcagagg | tgggttttct | gggaagcgaa | 1980 |
| tgacacctca | acttcagaat | cctttatttg | cacggccctg | tccaaggccc | tagatgccct | 2040 |
| gtacctggtt | ccctctttgt | tttcccaaag | tctccacaag | ttgtacaagt | tcaggtccc | 2100 |

```
tcagatatct ctacttcaca ttagaagact cggctgggtg cggtggctca cgcctgtaat    2160
cccagcactt tgggaagctg aggtgggtgg atcacgaggt caggagtttt gagaccagcc    2220
tggccaacat ggtgaaaccc tgtctttact aaaaatacaa aaattagccg ggcatggtgg    2280
tgggcacctg taatcccagc tactcgggaa gctgagacaa aattgtttga acctgggagg    2340
tggaggttgc agtgagctga gatcgcgcca ttgcactcca gcctgggtga cagagcgaga    2400
ctctgtctca aaaaaataaa taaggccggg cgtggtggct cacgcttgta atcccagcac    2460
tttgggagga cgaggcaggt ggatcatgaa gtcaggagat ggagaccatc ctggccaaca    2520
tgttaaaacc ctgtctccac taaaaataca aaaaattag ccaggtgtgg cggcaggtgc     2580
ctatagtccc agctacttcg gaggctgagg caggagaatg gtgttaaccc gggaggcaga    2640
gcttgcagtg agctgaaatt gcagccactg cactctagcc tgggcaacag agtgagactc    2700
tgtctcaaaa aataataata ataaaataag taaataaata aacaggctgg gctcggtggc    2760
tcacacctgt aatcccaaca ctttgggagg ccgaggtggg tggatcacct gaggtcagga    2820
gtttgagacc agcctagcca acctggtgaa acctcatcta tactaaaaat acaaaaatta    2880
tctgggcatg gtggcaggca cctgtaatcc tagctaccgg ggaggctgag gcaggagaat    2940
cacttgaacc tgggaggcag gggttgcagt gaaccgagat cgtgccattg cactccagcc    3000
tgggcaacag agtgagactc catctcaaat aaataaaaaa aaataaaaat acataaaaat    3060
aaataaataa ataaataaaa cattagaaga ctcacacgtg ggcttgaatc tataaaactt    3120
gaagcctacc tgagagagga caaagttgaa caggcgcttt ctctgaaaga tcactgcaat    3180
tcaccgctga ttccgagtat tctttctcat tcggggagcc ttttaccacc caaaaacaac    3240
aaaaaatatt actttagaat cagaaatagg aattcatgac tgaaatagga agccatggca    3300
ttcatacttt aaacttgacc tctttgtatg gaagagcaaa gaaatgagaa ttaatattat    3360
tatttattta tttatttatt tatttgagat ggagtctcgc tctgtcacca ggctggagtg    3420
cagtggcgcg atctcagctc actgcaacct ccacctcccg ggttcaagca attccctgc     3480
ctcagcctcc tgagtagctg ggactacagg cgcccgccac cacacccagc taatttttt     3540
gtatttttta gtagagtttc accatgttgg ccaggatgat ctcgatctct tgacctcatg    3600
atccatccgc ctaggcctcc caaagtgctg agatgacagg cgtgagccat cacacccggc    3660
cgagaattaa tattattata tccttctagg tactactcac aattgttgtt atgctttctg    3720
ttgtgccaac agctactatt tatttagctc ttactctgaa ccagatagtt taagtacttt    3780
gcatacatta tctctactaa tccttattgc cacattatga agtaaatgta cccattctac    3840
agatgaggag agtgagtctt ggagtgatta agtaacttac ctaaactcac actctaaact    3900
gggtctgttt aactccaaaa ccttatgctt catttaggca aagcagctaa gttagaatct    3960
ccaactatct tggctaaata atcttttcta caccaattct aatttctttt tttcttttt     4020
tgagacggag tcttactctg ttgcccaggc tggattgcag tggcaggatc ttggctcact    4080
gccacctccg cctcccaggt tcaagtgatt ctcgtgcctc agcctcctgg gcagctggga    4140
ttacaggtgc ctgccaccac acccagctaa ttttttgtatt tttttttttt ttttagagat   4200
ggggtttcat catgttggcc aggctggtct caaattcctg atctcaaggg atctacccac    4260
cttggcctcc caaagtactg ggattacagg cgtgagccac cgcacccagc ccaattctaa    4320
tttaataaat ctttaatatc taatgtgcac tttcctctca tagtctcttt cttaccaagc    4380
aatttagaga ttaaggaagc ttaattaaaa gaaatttaaa ttagacccta gctaactttt    4440
```

-continued

```
ttataattcc aaaatgatat ttatgttcca cctccaaacg agaaattacg gatgatcaaa    4500
acaataaagt cgattcagag agagcaaaat agtaataaac tgtaagtata agaatttgca    4560
aaccaaagaa gaaagcaaat gacactctac cctttaaaaa aaaaaatcac accatatagc    4620
ttttggatag tgttttttctg ttttgttttg gttttttaatt aactctgaag tcacttccac    4680
catatcactt aaatcattat tatctcaaat gttaaatgta tgttattcaa taaaattaca    4740
agatatcttt tatctaattt attatgtttt gtttcctacc ttttcaatgt cataaattta    4800
agaaaagtta caataactat aatctctacc caccccactc ccccactcct aaaacgacct    4860
gctgcaacgg ccagccatgc cttctcatcc taccttcgca tctgcttcaa gagaagagac    4920
cagagccggc tctgcagaga aggaagtcaa ttcttcttgt tagagtaact gacgtatttc    4980
tcttcccttc ctgtcgggca caggctgacg cagtgcaccc tgtgtggcca gccttacatg    5040
cctcggtggc tactcccaca tcactaggga cccagggagc aaagccaccc caaaaccaca    5100
tcaaggagct cttctatgcc aacatttttac attttttagct ggaggaaaga ccaggctgat    5160
gctggtgaaa tgtttcaccc ttcctaagga aactccctac agagactaca gccttcaaat    5220
attcaaatgt tctcacattt gtgaagggtt tcacattgac ttcagtgtaa atgactaacc    5280
acatctcaaa gaacagctat taactcaaga ataatttaca agaaagggggg acagccaggc    5340 caagagcgat gaagattgta atgaaatcac caagggggaac cttcaaaatg ctgtgcgtgt    5400
actaggtagt attactcagc accgtgaagt gtccctgccc tgctaactca ggcatggcca    5460
aggacttgct ctggagagca ataagacaat gaagtgtgtg caaaggtgcc acgtgccacg    5520
taggcttggc acctaccgag ccagtactgg ggccaccatt cattctcttt cccttctctt    5580
tcccttgatg actccagaca caggctgctc cagcaacctc gtctcagcat ggagaagaca    5640
tgaagcagag ccatggaaga tccttgatgg tcatggagtg tgagtggcaa ataaatgttt    5700
gctgtcatca accactgaga gtgtagggcc atttgtttct gcagctaacc tagcctattc    5760
tgctgatgta gtgtgtagtg ttttcacaaa cacagaactg agcaccaaac tatttaataa    5820
ctactatagc atgaatattt acccattgga acaaatgcca gcggaggccc tgctatacca    5880
cgagttatcc tttagttatt ggatcttggg gatgaggtcc cagggaaggg gctgcagtca    5940
ccaggattga gaggaagagg gacccaagaa gctcagagca gccactgttt catggggtac    6000
agaggtattt cagcacaact gtgcctccgc ttcccagctc aatagcagat ctaaatatag    6060
gcacttctta gctaatctct ttagcttttc tcagcacagg actctcactt tagatatgtg    6120
tcagccagag tttcttttcc tttacaacat taaattcctc agccatgagt gtttcaacag    6180
caccctcgtc ctcatcgtct tcttctgtta ctattatttt gactcagcat gatctcatag    6240
taacacactt cttggcacag gggaagaaag gaaaaaatgg aaaatccaca ggatggcatt    6300
tggactatga agggctgcag attatagcag aacaacactg ctggatatta ttattattat    6360
tatttttttt tttttttttt tgagaccgag tctcgctctt tcacccagtc gggactgcag    6420
tggcgcgatc tcggctcact gcaagctccg cctcccgggt tcacgctatt ctcctgcctc    6480
agcctcccga gtagctggga ctacaggcgc ccaccaccgc acccagctaa ttttttgtat    6540
ttttagtaga tacagggttt caccgtgtta gccaggatgg tctcgatctc ctgacctcgt    6600
gatccgcccg cctcggcctc ccaaagtgct gggattacag gcgtgagcca ccgcctgg    6660 cctattattt tatttttttga gacggagttt cgctcttgtt acccgggctg gagtgcaatg    6720
gcgctatctc agctcaccgc aatctctgcc tcctgggttc aagcgattct cctgcctcag    6780
cctcccaagt agctgggatt acaagcatgc accaccatgc ctggctaatt ttgtatttttt    6840
```

```
agtagagata gggtttctcc atgttggtca ggctagtctc gaactcccga cctctggtga   6900
tctgcccacc tcagcctccc aaagtactgg gattacaggt gtgagccact gcgcccagcc   6960
actgctggat attattgatg ttatttattg atgtgacagt tcattgattg ctatgattat   7020
taggcccaca cttgctaaat aaaggtattg gcagctccag tcccacagtc tgtattcaag   7080
aaatttgact ccagaaaaga aaggtgattg cacgcaaacc tgccaaccta tcactaacct   7140
ccaaattgaa aaacaaacct aagattcact ccactgactt actgcataga aactaaacat   7200
tattctaaaa tatggcagaa tgccaaagat tcatgagcag ttacgagtaa aggtgtctga   7260
gctccaatgc ttctgatgga catccattcg tggcagatgg aaggtgctgg aaatggcatc   7320
tggtgaactg ccaaatgtct taacgatttt aaattcctta gccctacaga ctacatcagt   7380
tgggcagaat ataataccac atcactgcat ttttccaagc actacaacat cacataagcc   7440
tagagaattc aaaccctcct atttacagat atatccgttt aaaagaaaaa attccataaa   7500
ggccatgttt tagtcaactt tgtagcctca acccccagct cagagcctga cacaaaggga   7560
gtgctcccata tatgtgtatt gaacaagtga acagatagtt gtgaagataa acagaccagc   7620
tcatccgttt actggcagcc tcaaaatgtc atacatcgcg atcatttaac aaatgttctt   7680
taatagttaa aattggagag tggtacccaa tgtataaaag ctaaaatcat gtaagcattt   7740
ttaaaatgca catttgcatg ttttctgttg atttatgtgc atgctggtga tccgcagtta   7800
taacaagatc catgcattaa ttatgcacca tcctagcaga cattcaggaa attgatttaa   7860
attaggaagt tcctaaaagg ttgtggggaa aattgaaaag gctgtcccaa gtgtcatgtt   7920
cttccattgc aggtgtttgc tcagaaccgg tttactcttg ctttgcacat aattctgtga   7980
cacttagcta ctgaactcca ggtccacaac aaagtagcag aagaaaaaag atttcagagg   8040
ctcctgattg gctcaggatc gtggtggggc caagagcttg aaccaggta ggcagagaac   8100
atccaaaacg agatctcagg tgatactgag aagggcaggc aggcaaagca atgtcagcat   8160
cagaatcaca tgtggactga ggcgcacgac tgaaacacca ggacagggga gttgaagcca   8220
ggtaataaga aaggaattca aaaggtagat aaagttcaga atccaaggag aggaagacca   8280
ggtgtggtaa agcaaccagc ctgcccagca agtctcctcg ctcaggccga acacccaggg   8340
ccaagcagcc ttgtgtcagt cagggctctg ccctcctctc gccagccctg tttccctcaa   8400
ggaggcaggt agttgcatct tcctccactc cccagttctc tccatttggg tctgaggcaa   8460
agctaacacc catgagggaa atgattcatg caataaattt taggccgggc atggtggctc   8520
acagctataa tcccagcact tgggaggct gaggctggag gatcccttaa gcccgggagt   8580
ttgagacctg cctgggcaac acagtgagat cccatctcta caaaagacat attaaaaaaa   8640
taggtgggtg tggtggctag tgcctggaat cccagctgct caggaggcta aggcaggaga   8700
ataccttgag cccaggagtt caagctctta gtggtctttg gatgactaaa cttcaacaca   8760
tcttagctca aaatctccga tcacaccact gcattccagc ccgggcaaca gaatgacacc   8820
ctgtctctaa ataaataaat aaataaatgt taattgtgta gctattatgt gccaggcaca   8880
atgtggaagg aaggggatac attagtgaat aaaacagatc cttcctgcat ggtacttagt   8940
ttctaaatgg agacacacca tcaacaagca accataaata cgttcttgca aactgagaga   9000
agtgctatga ggaaaatgta caggatgcag gggtggagga tgaggaggtc ggctacctta   9060
gatgccgtgg tcacagaatg gctctctgta ggagattttg agctaagata tgttaaaagt   9120
ttagtcatcc aaagatcact aagattagtc tatagtctga caacttagta actattgact   9180
```

```
tatggcaggg cagaatgggt gaggggaggg aggagtcgtt gggttaggtt cctcttgaag    9240
ggctctaata agaccctgat agaccgacca ggttacagtc cgatggtcat aatccagatg    9300
agagatatca atctttaact ggggtcccga gcatatgggg tagaaataac aagggttgtt    9360
gatggattag atgtgggatt tgaagtttag gtctaccaaa tccctgggac ccttgcagtc    9420
agctctttct tggggaatgg gaagtgggtt ccagcaacct gaattcaagt gcatgacgaa    9480
accagaaaaa gcaaacgcca aaatcaaaac tcggagcctc agaataccctg ccaatagatg    9540 catatgcccc agctttccgt ggagggcagt ttaccagagc ccagtgcaat tcctaatttc    9600
cataaagaac ccacatacaa ataaagtctg tctagttcac tatggttaag gtagtcagga    9660
agtgtgccac atttttacaaa attttccacc caaaatgttt ttttttaatg gtgcttaaag    9720
gaaaaattct catttacctg gaaaacttaa ctccccaaag ggaagtttcg ttcagatagc    9780
taaagcatgc caatcccagt ccccaaggga actgcaacaa cgtctcaccg ggcgcactgc    9840
cttcagcagt cactttcgag tttgttgcca ggtgtccgag cgggtttgaa cgtccgcgtc    9900
aatccacaca gtacaaaccg gaggaggggc cgggaccacc cttcccctcc aggactgcct    9960
tttgtacgtg tgttttgttt ctgttgctaa ggtttaggga gctgcccggc taccctcacg    10020
gattcccatg gaaactacca cctcccagag gacaggagga gaggcgaatt cagggtccac    10080
ccacgggccc cgcccaggga tggggtcact gagggtccgg gcagcgaagg gcggggcccg    10140
ggagctgggc atgggcgagg caggcgcgag aggagagggg cgtggcaggt ccggggcggg    10200
gcctgagtgc gcctgcgcag tccgcgccac tcagggagcc ggaggggacg cgccggagga    10260
aag                                                                 10263
```

<210> SEQ ID NO 2
<211> LENGTH: 6006
<212> TYPE: DNA
<213> ORGANISM: Mus musculus

<400> SEQUENCE: 2

```
taggttgggg cgagttgaca attaaagcta accaccatgc agtcccagaa cactgtgtcc      60
tctggggatg tcgaagccat ctatgctctg tggccttgc acagtgacaa tatcagcaaa       120
cctcacactc tgggacaaaa cctgtccctg tggtttacac atgcctgcat tcattcttgc      180
tacaatgctg gttgctgccc tgggcccggc aggcagtgac cttgattcag gcatctggag      240
ctgctggcaa gggggccaga acaggaaatg gagagtagaa agacaaaggg ggtgagaagg      300
ggaggccgac actgtttgta gccaggccct tgcttcttta cctactgatg ggtgttttga      360
gctggcagcc actgaaccaa aggaaataga tgtcggtcct gtattgtgtg ggccagcacg      420
ccagcagaat ggaagtgagc aggtagcagt gtgcaagtgc gagcctgcct gagaacacac      480
tgtcccaccc cgccccactc tgttcccaca gcctgcaggc cacagctgct cactgaggag      540
cctcgagctt ttggaggctg cagctaggcc cagctgttcc accacagctt tttttttttt      600
ttgagaatct tctcagcttc agggtgggac cacaacactt ctgcctccaa cgcaaaggac      660
aagccggggt gaccaaatag accttcacac tgtccctgag aaatcacacc ctttatgttc      720
cttgtgtagc ttcttctctc atgaaggttt tgatagccg cagagaacac gagcccaccc       780
aaggcagaag aggaataaag aagggcagtt atctctagtt ccagccagaa ctgggctccc      840
atttacaggc ttccaagatt ttgcgtaaat gaacattatc agaaagcctt gcacaggaag      900
ggaattgtgt gctcaaaaag tttatctttg ccgattatca ttaatcattg gtgggttttc      960
tggggaagtc aagccctggc caaggtcccg tttctttaat gtttatttttg acagttttta    1020
```

```
caaggcgggt cagcctcaga tcccttagaa catactcccg gaaggctatc ccagtggggc      1080
agaaccatgg ctctctgtga gagtgctatg tatgctcctc atttgggtgg atccgtgcta      1140
cccagctttc ccctgcacct cccatggtct tgtagaatca gagtaaaaga gagggggaaa      1200
aaaaaatcag gattttcatg gtttaaactt gacctcttca cacagaaggt caaagaagta      1260
aaaattaaca caacgttgcc atggcaacca cagactcctg tcactatgtt ttttgttgtt      1320
gggatagcca ctgttagttt agtactccct ctaggccccg cagattagca agtatgttat      1380
acactaaagg tctctgtggc aggctgaagt cagtgtaccc actctacaga tttgaaaatg      1440
gaggcagggt atttggtaat ttacctgaag tcacactggg actctgaaac ctgattcttt      1500
gtctggatac agaagttaag aagttatagt ctccaattaa ttatcttgtc tgaatgattt      1560
ttttttctct atcaactcta ctatcaataa agatctaata tacactttcc tttgacaact      1620
tatgtcatac tgaggtatct atttgggact gaataaagct caattaagag aaatttaagg      1680
gtctggtggg tcatgccttt aatttcggta ctcaggaatc agaggtaggt ggatctcagt      1740
gagttcaagg ccagcctggt ctacctatag taagtttgag gccagcttgt ctatatatag      1800
tgagcttagg tcaaaaatct ctacaaagtg agaacctgtc aagatagaga gagaaaatag      1860
ggtttaaagt aggtcctggg caattttact tctttattgt aaaattatat ttatctttca      1920
tcttcaaact agaggtcaag gttgacgaaa acagcctaaa ccaatgaagc tgattcagaa      1980
caaaacaagt ggtgtacata agaccttgaa agccaaggta gccagatgct atgctattgc      2040
ctaagaaggc atgccatgcg gctttggtat gctgtctcgt gttttgttct ttaaatctta      2100
agttactttc ctgattagaa catcattact ttctctctct ctctctctct ctctctctct      2160
ctctctccct ctctctctct ctctctctct ctcttttctt tctttctttc tttctttctt      2220
tctttctttc tttctttctt tctttctttc tttctttctt ccttcctttc tttctttctt      2280
tcttcctttc ttgagacagg gtttctctga gtagctcaac ctgccccaga acttgatttg      2340
tagcccaggc tggcctcaaa ctcacagaga tccacctgcc tgtgcctcct gagtaccacc      2400
actgccaggc tcatcattac attatcaatg tctcctattc aacacaatca caaggcttgc      2460
tgttcctgcc atcaatctag ggacagctct aacagctgaa agaccacgag ctcccatgta      2520
gactccgggc ttcctcctac cttaatctgg agtgtgtcct gatgaggaag tcagttcctt      2580
caccattgac ctgtgtgtct tcttcctgcc tgccaggcac tggctgaggc tgatggttta      2640
catggctgtc ccaagtgtgg ctgtagctaa tcccacgtca ccaaggaccc agacagcgga      2700
gacgtcctaa tgctacgcca aggagctcac atgaggattt acactgcaa gctagaagat      2760
aagagacttc ggtgaaatgc ctcatccttc cccccaaacg cccagcagag cccagtgtgt      2820
ttcctgtgtg tgacctcagg tgcatgacta ctgacaccac aaagaacagc ttctcatgga      2880
ccgtcatggg catttccagg gtaaattttt ttgaaggctg acatgcatgc aggatagtat      2940
gtaaatcata agcatatttg tcatgttctg aatggctgtc ccttctcaaa cttattcaaa      3000
tgtaactgcc atggcattgg gtatcagtgg tgtgacgaga aggccacagg gtctctactc      3060
tcaggctaga ttaacagtag catcctggga gtgggcccct tgattcaatt gtgggtttct      3120
tatatttttg gttgtgagcc tagcctttaa cggatgagac atctttccag cccccagagt      3180
gggtttctta agaaaaatg agtttgggtg ctttactgct cctcctcccc ctcctcctcc      3240
tcttcctcct ctgcttcctc ctcctcttct tctccctccc ttctttccat ctccacttct      3300
gctatgggat gccttccctc tgtatatgac ctagatgcca gtatcaggac cctgaacttg      3360
```

```
cccaccttca gcatagatgc tgagggttgg gatgtagtag ggagactaaa gtaagagggt    3420
gagctttggg ggctgtggag atggtttggc agatagaaga ctagctgtct gttttagtta    3480
gagttttgct gctgtgaaca gacaccatga ccaagacaac tcttataagg acaacattta    3540
attggggctg gcttacaggt tcagaggttc agtccattat catcaaggca ggagcatggc    3600
agcatccaag taggcatggt gcaagcagag ctgagagttc tacatcttca tctgaaggct    3660
gctatgagga gtctggcttc caggcagcta ggatgaggtg ttaaagccca cacccacagt    3720
gacacgccta ctccaacaag gccacatctt ctactagtgc caccccatta ggagagcata    3780
tacaaaccat cacactgtcc aagcatgatg acctgagtct ggactcccag tacccacaga    3840
acagccaggt gcagaggtgt catccagtgc tggggaggag tagagagagg caaaagagtt    3900
tgggtactct tttcctcctc ctcctcctcc cattcctcct ccctaggcag aatggcaagc    3960
tccaggttca gtgggagacc tgattcaata agaaagagta atagcaggtt atgcttatgc    4020
ctacttctgc cttctacaaa tgcacacgcg tgcacacaca taccacatga ccacaaataa    4080
atacattaaa aactggagta aagggtaaca ccaatcttga gcaatctcaa gcaaatcact    4140
ctgtgaatcc ccacttcctg gtgagactca ctaggcttgc ctcctggctt gatagcctgc    4200
tcccgttcaa tcgcagtgtt tgtggtgtgt ctgttatggg ctgggtacca ccacaggggc    4260
tgcgatggag aagctctggc cctaaggtaa aatcctcaat aaataggaac ttgtatttat    4320
tggttagtag aactataggc atgaagtgct gagtcaccc atttaggaat atttgagaga    4380
aaatgctttg aaaatgagaa tcgttaccta aaatgtagac acttcagtct gcttggctgc    4440
ataacaaata tgacggaagg ggcagcttgc atagcaactt cttttctcac aatttgggag    4500
cccaaggtta agatacgggc aaggctgagt gaggcccatt ttcattttg ttttattgt    4560 ttttacattc tctttgcttc atagcccagg ctagccgcct gcctcaccct cccaagtgct    4620
gggattacgt gagtgtgcca cccatgcctg ggttatttct agtcatttaa atttttatt    4680 tattcataaa acagagacgt gaagattggg tttattttt ttcaattttt tattagatat    4740
tttcttcatt tacatttcaa atgctatcct gaaagtcccc tatcccctcc cctcgccctg    4800
ctctcctggg tttattattt attttgaaag atcttatttt ttatttatgt gtctgctgag    4860
gccagaagaa gacatcagct cccttagaga aagggctaca ggatgagaaa tgtctcatat    4920
gtgtgctggg agccaagctt ttctggaaga gcggatgggt tcttaactgc tgattcatct    4980
cactaggccc tctcttcatt attaaaaagc aaaaaattta aacttcattg ctattcagca    5040
aaagagtcat gtccgagtat atcatttaaa aatatatctt tgggttacaa aggaaacaat    5100
aaagggagct tggagactct catctgaggc tcccaactac aatgagcagc aggtcacggt    5160
gttggcagag acagatgtgt agaagctgag caggtaggta caaacagagt agattaaaag    5220
agtggtgatg ttgacttggc cacaggatca tcaggtggat gactgacaac aacattagcc    5280
aggcactagc ctgccaatgt gcttcttacc atgagagctc ccaactttct ttttttttt    5340 tttttttttt tggttttttt tcgagacagg gtttctctgt atagctctgg ctgtcctgga    5400
actcactttg tagaccaggc tggcctcgaa ctcgggaatc cgcctgcctc tgcatcccaa    5460
gtgctgggat taaaggcgtg tgccaccacg cccgtgaga gctcccaact ttggttcaga    5520
tagctgatcc ggaaggagaa gcaaccaatg cgccatactg ttgaagtcat tctacaatt    5580 tgttcctagt caagatttgt ttgaaagttt cattttctat agtgtgagcg ggagggaggg    5640
ccaggacctc tttcttcccc tcggagacca gcttttgttc ctttgtttgg tttggttgt    5700 cggtgtttag agagaggtta ggtggctctg acagtttgct ttggaaacca catcccagag    5760
```

```
ggctcagaga cacacatgcc ctgttacttg gagactgaag aggagcagca ggcggggccg    5820
aagggtgggc ggagccacta gtggagggc cggtggtagg aggagccttt ggtggaggga     5880
ccgggcccta gagcgtaggt agttattggt agtggtcagg gtcccccgcg cggggcgga     5940 gtgggcgtgt tctggccgcg cctgcgcagt ccactctact cggcgggcga aggagacgcg    6000
ttaaag                                                              6006
```

<210> SEQ ID NO 3
<211> LENGTH: 9407
<212> TYPE: DNA
<213> ORGANISM: Artificial sequence
<220> FEATURE:
<223> OTHER INFORMATION: Description of Artifical Sequence: Synthetic
      construct including nucleotide sequence of mouse Tctex-1
      regulatory sequence and nucleotide sequence encoding modified
      green flurescent protein

<400> SEQUENCE: 3

```
gaattctagg ttggggcgag ttgacaatta aagctaacca ccatgcagtc ccagaacact      60
gtgtcctctg gggatgtcga agccatctat gctctgtggc ctttgcacag tgacaatatc     120
agcaaacctc acactctggg acaaaacctg tccctgtggt ttacacatgc ctgcattcat     180
tcttgctaca atgctggttg ctgccctggg cccggcaggc agtgaccttg attcaggcat     240
ctggagctgc tggcaagggg gccagaacag gaaatggaga gtagaaagac aaaggggtg     300 agaaggggag gccgacactg tttgtagcca ggcccttgct tctttaccta ctgatgggtg     360
ttttgagctg gcagccactg aaccaaagga aatagatgtc ggtcctgtat tgtgtgggcc     420
agcacgccag cagaatggaa gtgagcaggt agcagtgtgc aagtgcgagc ctgcctgaga     480
acacactgtc ccaccccgcc ccactctgtt cccacagcct gcaggccaca gctgctcact     540
gaggagcctc gagcttttgg aggctgcagc taggcccagc tgttccacca cagctttttt     600
ttttttttga gaatcttctc agcttcaggg tgggaccaca cacttctgc ctccaacgca     660 aaggacaagc cggggtgacc aaatagacct tcacactgtc cctgagaaat cacacccttt     720
atgttccttg tgtagcttct ttctctatga aggttttttga tagccgcaga gaacacgagc     780
ccacccaagg cagaagagga ataaagaagg gcagttatct ctagttccag ccagaactgg     840
gctcccattt acaggcttcc aagattttgc gtaaatgaac attatcagaa agccttgcac     900
aggaagggaa ttgtgtgctc aaaaagttta tctttgccga ttatcattaa tcattggtgg     960
gttttctggg gaagtcaagc cctggccaag gtcccgtttc tttaatgttt attttgacag    1020
tttttacaag gcgggtcagc ctcagatccc ttagaacata ctcccggaag gctatcccag    1080
tggggcagaa ccatggctct ctgtgagagt gctatgtatg ctcctcattt gggtggatcc    1140
gtgctaccca gctttcccct gcacctccca tggtcttgta gaatcagagt aaaagagagg    1200
gggaaaaaaa aatcaggatt tcatggtttt aaacttgacc tcttcacaca gaaggtcaaa    1260
gaagtaaaaa ttaacacaac gttgccatgg caaccacaga ctcctgtcac tatgtttttt    1320
gttgttggga tagccactgt tagtttagta ctccctctag gccccgcaga ttagcaagta    1380
tgttatacac taaaggtctc tgtggcaggc tgaagtcagt gtaccactc tacagatttg    1440 aaaatggagg cagggtattt ggtaatttac ctgaagtcac actgggactc tgaaacctga    1500
ttctttgtct ggatacagaa gttaagaagt tatagtctcc aattaattat cttgtctgaa    1560
tgattttttt ttctctatca actctactat caataaagat ctaatataca ctttcctttg    1620
acaacttatg tcatactgag gtatctatttt gggactgaat aaagctcaat taagagaaat    1680
```

```
ttaagggtct ggtgggtcat gcctttaatt tcggtactca ggaatcagag gtaggtggat   1740
ctcagtgagt tcaaggccag cctggtctac ctatagtaag tttgaggcca gcttgtctat   1800
atatagtgag cttaggtcaa aaatctctac aaagtgagaa cctgtcaaga tagagagaga   1860
aaatagggtt taaagtaggt cctgggcaat tttacttctt tattgtaaaa ttatatttat   1920
ctttcatctt caaactagag gtcaaggttg acgaaaacag cctaaaccaa tgaagctgat   1980
tcagaacaaa acaagtggtg tacataagac cttgaaagcc aaggtagcca gatgctatgc   2040
tattgcctaa gaaggcatgc catgcggctt tggtatgctg tctcgtgttt tgttctttaa   2100
atcttaagtt actttcctga ttagaacatc attactttct ctctctctct ctctctctct   2160
ctctctctct ctccctctct ctctctctct ctctctctct tttctttctt tctttctttc   2220
tttctttctt tctttctttc tttctttctt tcttctttc tttcttcctt cctttctttc   2280
tttctttctt cctttcttga gacagggttt ctctgagtag ctcaacctgc cccagaactt   2340
gatttgtagc ccaggctggc ctcaaactca cagagatcca cctgcctgtg cctcctgagt   2400
accaccactg ccaggctcat cattacatta tcaatgtctc ctattcaaca caatcacaag   2460
gcttgctgtt cctgccatca atctagggac agctctaaca gctgaaagac cacgagctcc   2520
catgtagact ccgggcttcc tcctaccttA atctggagtg tgtcctgatg aggaagtcag   2580
ttccttcacc attgacctgt gtgtcttctt cctgcctgcc aggcactggc tgaggctgat   2640
ggtttacatg gctgtcccaa gtgtggctgt agctaatccc acgtcaccaa ggacccagac   2700
agcggagacg tcctaatgct acgccaagga gctcacatga ggattttaca ctgcaagcta   2760
gaagataaga gacttcggtg aaatgcctca tccttccccc caaacgccca gcagagccca   2820 gtgtgttttcc tgtgtgtgac ctcaggtgca tgactactga caccacaaag aacagcttct   2880
catggaccgt catgggcatt tccagggtaa attttttga aggctgacat gcatgcagga   2940
tagtatgtaa atcataagca tatttgtcat gttctgaatg gctgtcccctt tcaaacttA   3000 ttcaaatgta actgccatgg cattgggtat cagtggtgtg acgagaaggc cacagggtct   3060
ctactctcag gctagattaa cagtagcatc ctgggagtgg gccccttgat tcaattgtgg   3120
gtttcttata ttttttggttg tgagcctagc ctttaacgga tgagacatct ttccagcccc   3180
cagagtgggt ttcttataag aaaatgagtt tgggtgcttt actgctcctc ctcccccctcc   3240 tcctcctctt cctcctctgc ttcctcctcc tcttcttctc cctcccttct ttccatctcc   3300
acttctgcta tgggatgcct tccctctgta tatgacctag atgccagtat caggaccctg   3360
aacttgccca ccttcagcat agatgctgag ggttgggatg tagtagggag actaaagtaa   3420
gagggtgagc tttggggget gtggagatgg tttggcagat agaagactag ctgtctgttt   3480
tagttagagt tttgctgctg tgaacagaca ccatgaccaa gacaactctt ataaggacaa   3540
catttaattg gggctggctt acaggttcag aggttcagtc cattatcatc aaggcaggag   3600
catggcagca tccaagtagg catggtgcaa gcagagctga gagttctaca tcttcatctg   3660
aaggctgcta tgaggagtct ggcttccagg cagctaggat gaggtgttaa agcccacacc   3720
cacagtgaca cgcctactcc aacaaggcca catcttctac tagtgccacc ccattaggag   3780
agcatataca aaccatcaca ctgtccaagc atgatgacct gagtctggac tcccagtacc   3840
cacagaacag ccaggtgcag aggtgtcatc cagtgctggg gaggagtaga gagaggcaaa   3900
agagtttggg tactcttttc ctcctcctcc tcctcccatt cctcctccct aggcagaatg   3960
gcaagctcca ggttcagtgg gagacctgat tcaataagaa agagtaatag caggttatgc   4020
```

-continued

```
ttatgcctac ttctgccttc tacaaatgca cacgcgtgca cacacatacc acatgaccac    4080
aaataaatac attaaaaact ggagtaaagg gtaacaccaa tcttgagcaa tctcaagcaa    4140
atcactctgt gaatccccac ttcctggtga gactcactag gcttgcctcc tggcttgata    4200
gcctgctccc gttcaatcgc agtgtttgtg gtgtgtctgt tatgggctgg gtaccaccac    4260
aggggctgcg atggagaagc tctggcccta aggtaaaatc ctcaataaat aggaacttgt    4320
atttattggt tagtagaact ataggcatga agtgctgagt caacccattt aggaatattt    4380
gagagaaaat gctttgaaaa tgagaatcgt tacctaaaat gtagacactt cagtctgctt    4440
ggctgcataa caaatatgac ggaaggggca gcttgcatag caacttcttt tctcacaatt    4500
tgggagccca aggttaagat acgggcaagg ctgagtgagg cccattttca ttttttgtttt    4560 tattgttttt acattctctt tgcttcatag cccaggctag ccgcctgcct caccctccca    4620
agtgctggga ttacgtgagt gtgccaccca tgcctgggtt atttctagtc atttaaattt    4680
tttatttatt cataaaacag agacgtgaag attgggttta ttttttttca attttttatt    4740
agatattttc ttcatttaca tttcaaatgc tatcctgaaa gtcccctatc ccctcccctc    4800
gccctgctct cctgggttta ttatttattt tgaaagatct tatttttttat ttatgtgtct    4860 gctgaggcca aagaagaca tcagctccct tagagaaagg gctacaggat gagaaatgtc     4920
tcatatgtgt gctgggagcc aagcttttct ggaagagcgg atgggttctt aactgctgat    4980
tcatctcact aggccctctc ttcattatta aaaagcaaaa aatttaaact tcattgctat    5040
tcagcaaaag agtcatgtcc gagtatatca tttaaaaata tatctttggg ttacaaagga    5100
aacaataaag ggagcttgga gactctcatc tgaggctccc aactacaatg agcagcaggt    5160
cacggtgttg gcagagacag atgtgtagaa gctgagcagg taggtacaaa cagagtagat    5220
taaaagagtg gtgatgttga cttggccaca ggatcatcag gtggatgact gacaacaaca    5280
ttagccaggc actagcctgc caatgtgctt cttaccatga gagctcccaa ctttcttttt    5340
tttttttttt tttttttggt ttttttttcga gacagggttt ctctgtatag ctctggctgt    5400
cctggaactc actttgtaga ccaggctggc ctcgaactcg gaatccgcc tgcctctgca     5460 tcccaagtgc tgggattaaa ggcgtgtgcc accacgcccg gtgagagctc caactttgg    5520 ttcagatagc tgatccggaa ggagaagcaa ccaatgcgcc atactgttgg aagtcattct    5580
acaatttgtt cctagtcaag atttgtttga aagtttcatt ttctatagtg tgagcgggag    5640
ggagggccag gacctctttc ttcccctcgg agaccagctt tgttcctttt gtttggtttg    5700
ggttgtcggt gtttagagag aggttaggtg gctctgacag tttgctttgg aaaccacatc    5760
ccagagggct cagagacaca catgccctgt tacttggaga ctgaagagga gcagcaggcg    5820
gggccgaagg gtgggcggag ccactagtgg aggggccggt ggtaggagga gcctttggtg    5880
gagggaccgg gccctagagc gtaggtagtt attggtagtg gtcagggtcc cccgcgcggg    5940
ggcggagtgg gcgtgttctg gccgcgcctg cgcagtccac tctactcggc gggcgaagga    6000
gacgcgttaa agatggaaga cttccagggg gatccaccgg tcgccaccat ggtgagcaag    6060
ggcgaggagc tgttcaccgg ggtggtgccc atcctggtcg agctggacgg cgacgtaaac    6120
ggccacaagt tcagcgtgtc cggcgagggc gagggcgatg ccacctacgg caagctgacc    6180
ctgaagttca tctgcaccac cggcaagctg cccgtgccct ggcccaccct cgtgaccacc    6240
ctgacctacg gcgtgcagtg cttcagccgc taccccgacc acatgaagca gcacgacttc    6300
ttcaagtccg ccatgcccga aggctacgtc caggagcgca ccatcttctt caaggacgac    6360
ggcaactaca agacccgcgc cgaggtgaag ttcgagggcg acaccctggt gaaccgcatc    6420
```

```
gagctgaagg gcatcgactt caaggaggac ggcaacatcc tggggcacaa gctggagtac    6480
aactacaaca gccacaacgt ctatatcatg gccgacaagc agaagaacgg catcaaggtg    6540
aacttcaaga tccgccacaa catcgaggac ggcagcgtgc agctcgccga ccactaccag    6600
cagaacaccc ccatcggcga cggccccgtg ctgctgcccg acaaccacta cctgagcacc    6660
cagtccgccc tgagcaaaga ccccaacgag aagcgcgatc acatggtcct gctggagttc    6720
gtgaccgccg ccgggatcac tctcggcatg gacgagctgt acaagtaaag cggccgctcg    6780
ggttggactg tgagagggag ggtggcggcg gagatccggg tgtggcgggg cccggtctgg    6840
gaagacacag cttctgctca cggccacctg gcccgaggct gatgagccta cacacaattt    6900
gtcaaaaatc ccacacaatt tgtcaaaaac aataataata aaaccctaac acttcctctt    6960
ttgacatttc taaagtgtca actaaggata ttctgaggga agagtaagac atttgcattt    7020
atcagaatct ttcagttttg gtcggtctat tttcccaaca cacttttcgg cagtcaggat    7080
cctttgtttt gaacgttggc ggttccctgc ggacactccg cgtcattccc gcgtgggcgg    7140
tgcccgcggt ccgcggagac tgcgctgggc tcgtgtctcg gtggggttca cggcgtcggg    7200
aggatgacgt cactccaccc cttccgcact gctgcagacc ccagccggga ccgaggttgg    7260
gaaaggaggc atcctgctgt ggcatgtata gtgacacagg cgcgcagggc cagctccggg    7320
tgaccgcagt gggggtctgc tgcccagtct gtctgtctgc caaggaccga cgtgcgaaca    7380
gaacctgcct ttgtctcggt gccgcacctt gtccttcagt gcggcgctcc ctcccaccca    7440
ggccacagcg actgggtaca tttcatttca gtttaagata gtaacggaat ctctcattct    7500
tgtgggggaa gaatgtaatg cctcttagta ccctagccac tcgccttgat gatgtgttgt    7560
caaaatgttt ttcccttcgt gctaacacgc atttgaaaaa cagctgaatg gacgccagtt    7620
aaagaatagt tgctcatttt ttccctgaat aatctttgtt gaaactcaat aaaatcccac    7680
acaatttgtc aaaacaata ataataaaac cctaacactt cctcttttga catttctaaa    7740
gtgtcaacta aggatattct gagggaagag taagacattt gcatttatca gaatctttca    7800
gttttggtct attttcccaa cacacttttc ggcagtcagg atcatttgt ttgaacgttg    7860 gtggaacgca agtaaagact ctgaagccac gattccgaag cagcagcaca ggggatgttt    7920
ggccagacag cgatctcatg tatggctgaa gattggcttt tatggtagtc acagccagct    7980
agactttata ggaaggaaat ggccatgtga aaaggtagcc ctcacaaccg cgttctaatt    8040
ccagcttgta catgtagact gactgaagtg aagtatccag acagtgatct gtgttttaca    8100
cagagtgtca gcagcaggag gacggccact ctgcattgtt tacccagcag ccctctcagc    8160
tgagcctttt ctacctgcct ctagctcccc aggtttccct cagctcattt ccctctctgg    8220
tagcagctgg cagtgctccc tgatttcaat ataatttctc ttctgttatt tcttactct    8280 aagtgtatgg gaagtgacac tagggttttg cttttgtggct taggatcact gtagtcactt    8340
aggaagagcc tttcagtcga cttaccctgg agagtcacca catttcact atttcagtga    8400 tttcggctt gtttccaact gacttcttag agggtctagc aagggaaatg gctttgggtg    8460
gtcaattctc attctcctga agaggaaggg gtgatactca atactagaac agggcaggt    8520 ccactgtggt cagcagtaag ggaagtctgt agcaaaacag gactgagtga ctgccgaggg    8580
aggctgtgct atccgatcca gggcctgtcc agtgctaagg ctatcccaga acttggaata    8640
gttcatttgt tctcaggtaa gaagcatact gcaggctagt gcctggccaa tgttttcagg    8700
aaaccctcac acccactcaa atccagtatt atgttaagag gagactaaga aaactacttc    8760
```

| | |
|---|---|
| gggcatcacc ttgctgctgg cagccctcaa gtcagctgat gcttcgtcct gaagtagttc | 8820 |
| attgggggtta agaaaatgat gggcacacat gagcctttta cgtgttaaac atcctagtca | 8880 |
| ttatctttac aatgatgact tatgtttctt cagctgcttt gtatggcagt ggagtggctc | 8940 |
| ggaatatggc acctgcactg gctaattgtg ctgacagcca gctgcagggg aaggagagac | 9000 |
| aggattctag tttgaagtga cacctggctt gcagtgtgac actcagctgc ttcacacctc | 9060 |
| tggggtctga ggttcatctg cacagtcgac agcctgattt ctaagtctcc ttcagtatct | 9120 |
| cattgtgtgc tcattgatgc tctgcagaaa gctcttttaa accaaactta tctacatttt | 9180 |
| cttccttaac agactgcatt tgttgttgat gaagtgagca gcattgtaaa ggaggtaaga | 9240 |
| ggaaacagtc ttgttttcca ggcgtttggt tggtactatg tgtcttggag ttaccattac | 9300 |
| tgtgatttaa caccatgacc acagcaattt gaggaacaaa gaagggtttc ttcagcttac | 9360 |
| acttccacat cacagttcat catcaaagga agtcaggata ggaattc | 9407 |

<210> SEQ ID NO 4
<211> LENGTH: 21
<212> TYPE: DNA
<213> ORGANISM: Artificial sequence
<220> FEATURE:
<223> OTHER INFORMATION: Synthetic primer

<400> SEQUENCE: 4
gaggagctgt tcaccggggt g           21

<210> SEQ ID NO 5
<211> LENGTH: 21
<212> TYPE: DNA
<213> ORGANISM: Artificial sequence
<220> FEATURE:
<223> OTHER INFORMATION: Synthetic primer

<400> SEQUENCE: 5
gtggttgtcg ggcagcagca c           21

<210> SEQ ID NO 6
<211> LENGTH: 9499
<212> TYPE: DNA
<213> ORGANISM: Artificial Sequence
<220> FEATURE:
<223> OTHER INFORMATION: Description of Artificial Sequence: Synthetic
      construct including nucleotide sequence of mouse Tctex-1
      regulatory sequence and nucleotide sequence encoding modified
      green fluorescent protein

<400> SEQUENCE: 6

| | |
|---|---|
| gaattctagg ttggggcgag ttgacaatta aagctaacca ccatgcagtc ccagaacact | 60 |
| gtgtcctctg gggatgtcga agccatctat gctctgtggc ctttgcacag tgacaatatc | 120 |
| agcaaacctc acactctggg acaaaacctg tccctgtggt ttacacatgc ctgcattcat | 180 |
| tcttgctaca atgctggttg ctgccctggg cccggcaggc agtgacccttg attcaggcat | 240 |
| ctggagctgc tggcaagggg gccagaacag gaaatggaga gtagaaagac aaaggggggtg | 300 |
| agaaggggag gccgacactg tttgtagcca ggcccttgct tctttaccta ctgatgggtg | 360 |
| ttttgagctg gcagccactg aaccaaagga aatagatgtc ggtcctgtat tgtgtgggcc | 420 |
| agcacgccag cagaatggaa gtgagcaggt agcagtgtgc aagtgcgagc ctgcctgaga | 480 |
| acacactgtc ccaccccgcc ccactctgtt cccacagcct gcaggccaca gctgctcact | 540 |
| gaggagcctc gagcttttgg aggctgcagc taggcccagc tgttccacca cagcttttt | 600 |

```
tttttttttga gaatcttctc agcttcaggg tgggaccaca acacttctgc ctccaacgca      660
aaggacaagc cggggtgacc aaatagacct tcacactgtc cctgagaaat cacacccttt      720
atgttccttg tgtagcttct ttctctatga aggttttga tagccgcaga gaacacgagc       780
ccacccaagg cagaagagga ataaagaagg gcagttatct ctagttccag ccagaactgg      840
gctcccattt acaggcttcc aagattttgc gtaaatgaac attatcagaa agccttgcac      900
aggaagggaa ttgtgtgctc aaaaagttta tctttgccga ttatcattaa tcattggtgg      960
gttttctggg gaagtcaagc cctggccaag gtcccgtttc tttaatgttt attttgacag     1020
ttttttacaag gcgggtcagc ctcagatccc ttagaacata ctcccggaag gctatcccag    1080
tggggcagaa ccatggctct ctgtgagagt gctatgtatg ctcctcattt gggtggatcc     1140
gtgctaccca gctttcccct gcacctccca tggtcttgta gaatcagagt aaaagagagg     1200
gggaaaaaaa aatcaggatt ttcatggttt aaacttgacc tcttcacaca gaaggtcaaa    1260
gaagtaaaaa ttaacacaac gttgccatgg caaccacaga ctcctgtcac tatgttttt     1320
gttgttggga tagccactgt tagtttagta ctccctctag gccccgcaga ttagcaagta     1380
tgttatacac taaaggtctc tgtggcaggc tgaagtcagt gtacccactc tacagatttg     1440
aaaatggagg cagggtattt ggtaatttac ctgaagtcac actgggactc tgaaacctga    1500
ttctttgtct ggatacagaa gttaagaagt tatagtctcc aattaattat cttgtctgaa    1560
tgattttttt ttctctatca actctactat caataaagat ctaatataca cttttccttg    1620
acaacttatg tcatactgag gtatctattt gggactgaat aaagctcaat aagagaaat    1680
ttaagggtct ggtgggtcat gcctttaatt tcggtactca ggaatcagag gtaggtggat    1740
ctcagtgagt tcaaggccag cctggtctac ctatagtaag tttgaggcca gcttgtctat    1800
atatagtgag cttaggtcaa aaatctctac aaagtgagaa cctgtcaaga tagagagaga    1860
aaatagggtt taaagtaggt cctgggcaat tttacttctt tattgtaaaa ttatatttat    1920
ctttcatctt caaactagag gtcaaggttg acgaaaacag cctaaaccaa tgaagctgat    1980
tcagaacaaa acaagtggtg tacataagac cttgaaagcc aaggtagcca gatgctatgc    2040
tattgcctaa gaaggcatgc catgcggctt tggtatgctg tctcgtgttt tgttcttaa     2100
atcttaagtt acttcctga ttagaacatc attactttct ctctctctct ctctctctct    2160
ctctctctct ctccctctct ctctctctct ctctctctct tttctttctt tctttctttc    2220
tttcttttctt tctttctttc tttctttctt tctttctttc tttcttcctt cctttctttc  2280
tttctttctt cctttcttga gacagggttt ctctgagtag ctcaacctgc cccagaactt    2340
gatttgtagc ccaggctggc ctcaaactca cagagatcca cctgcctgtg cctcctgagt    2400
accaccactg ccaggctcat cattacatta tcaatgtctc ctattcaaca caatcacaag    2460
gcttgctgtt cctgccatca atctagggac agctctaaca gctgaaagac cacgagctcc    2520
catgtagact ccgggcttcc tcctacctta atctggagtg tgtcctgatg aggaagtcag    2580
ttccttcacc attgacctgt gtgtcttctt cctgcctgcc aggcactggc tgaggctgat    2640
ggtttacatg gctgtcccaa gtgtggctgt agctaatccc acgtcaccaa ggacccagac    2700
agcggagacg tcctaatgct acgccaagga gctcacatga ggattttaca ctgcaagcta    2760
gaagataaga gacttcggtg aaatgcctca tccttccccc caaacgccca gcagagccca    2820
gtgtgttttcc tgtgtgtgac ctcaggtgca tgactactga caccacaaag aacagcttct    2880
catgaccgt catgggcatt tccagggtaa attttttga aggctgacat gcatgcagga     2940
tagtatgtaa atcataagca tatttgtcat gttctgaatg gctgtcccctt ctcaaactta    3000
```

```
ttcaaatgta actgccatgg cattgggtat cagtggtgtg acgagaaggc cacagggtct   3060
ctactctcag gctagattaa cagtagcatc ctgggagtgg gccccttgat tcaattgtgg   3120
gtttcttata ttttttggttg tgagcctagc ctttaacgga tgagacatct ttccagcccc   3180
cagagtgggt ttcttataag aaaatgagtt tgggtgcttt actgctcctc ctcccccctcc   3240
tcctcctctt cctcctctgc ttcctcctcc tcttcttctc cctcccttct ttccatctcc   3300
acttctgcta tgggatgcct tccctctgta tatgacctag atgccagtat caggaccctg   3360
aacttgccca ccttcagcat agatgctgag ggttgggatg tagtagggag actaaagtaa   3420
gagggtgagc tttgggggct gtggagatgg tttggcagat agaagactag ctgtctgttt   3480
tagttagagt tttgctgctg tgaacagaca ccatgaccaa gacaactctt ataaggacaa   3540
catttaattg gggctggctt acaggttcag aggttcagtc cattatcatc aaggcaggag   3600
catggcagca tccaagtagg catggtgcaa gcagagctga gagttctaca tcttcatctg   3660
aaggctgcta tgaggagtct ggcttccagg cagctaggat gaggtgttaa agcccacacc   3720
cacagtgaca cgcctactcc aacaaggcca catcttctac tagtgccacc ccattaggag   3780
agcatataca aaccatcaca ctgtccaagc atgatgacct gagtctggac tcccagtacc   3840
cacagaacag ccaggtgcag aggtgtcatc cagtgctggg gaggagtaga gagaggcaaa   3900
agagtttggg tactcttttc ctcctcctcc tcctcccatt cctcctccct aggcagaatg   3960
gcaagctcca ggttcagtgg gagacctgat tcaataagaa agagtaatag caggttatgc   4020
ttatgcctac ttctgccttc tacaaatgca cacgcgtgca cacacatacc acatgaccac   4080
aaataaatac attaaaaact ggagtaaagg gtaacaccaa tcttgagcaa tctcaagcaa   4140
atcactctgt gaatccccac ttcctggtga gactcactag gcttgcctcc tggcttgata   4200
gcctgctccc gttcaatcgc agtgtttgtg gtgtgtctgt tatgggctgg gtaccaccac   4260
aggggctgcg atggagaagc tctggcccta aggtaaaatc tcaataaat aggaacttgt   4320
atttattggt tagtagaact ataggcatga agtgctgagt caacccattt aggaatattt   4380
gagagaaaat gctttgaaaa tgagaatcgt tacctaaaat gtagacactt cagtctgctt   4440
ggctgcataa caaatatgac ggaaggggca gcttgcatag caacttcttt tctcacaatt   4500
tgggagccca aggttaagat acgggcaagg ctgagtgagg cccatttca ttttgtttt   4560
tattgttttt acattctctt tgcttcatag cccaggctag ccgcctgcct caccctccca   4620
agtgctggga ttacgtgagt gtgccaccca tgcctgggtt atttctagtc atttaaattt   4680
tttatttatt cataaaacag agacgtgaag attgggttta ttttttttca atttttatt   4740
agatattttc ttcatttaca tttcaaatgc tatcctgaaa gtccctatc ccctcccctc   4800
gccctgctct cctgggttta ttatttattt tgaaagatct tatttttat ttatgtgtct   4860
gctgaggcca gaagaagaca tcagctccct tagagaaagg gctacaggat gagaaatgtc   4920
tcatatgtgt gctgggagcc aagcttttct ggaagagcgg atgggttctt aactgctgat   4980
tcatctcact aggccctctc ttcattatta aaaagcaaaa aatttaaact tcattgctat   5040
tcagcaaaag agtcatgtcc gagtatatca tttaaaaata tatctttggg ttacaaagga   5100
aacaataaag ggagcttgga gactctcatc tgaggctccc aactacaatg agcagcaggt   5160
cacggtgttg gcagagacag atgtgtagaa gctgagcagg taggtacaaa cagagtagat   5220
taaaagagtg gtgatgttga cttggccaca ggatcatcag gtggatgact gacaacaaca   5280
ttagccaggc actagcctgc caatgtgctt cttaccatga gagctcccaa cttttcttttt   5340
```

```
tttttttttt ttttttttggt ttttttttcga gacagggttt ctctgtatag ctctggctgt    5400
cctggaactc actttgtaga ccaggctggc ctcgaactcg gaatccgcc tgcctctgca       5460 tcccaagtgc tgggattaaa ggcgtgtgcc accacgcccg gtgagagctc caactttgg       5520 ttcagatagc tgatccggaa ggagaagcaa ccaatgcgcc atactgttgg aagtcattct       5580
acaatttgtt cctagtcaag atttgtttga aagtttcatt ttctatagtg tgagcgggag      5640
ggagggccag gacctctttc ttcccctcgg agaccagctt tgttccttt gtttggtttg       5700 ggttgtcggt gtttagagag aggttaggtg gctctgacag tttgctttgg aaaccacatc      5760
ccagagggct cagagacaca catgccctgt tacttggaga ctgaagagga gcagcaggcg      5820
gggccgaagg gtgggcggag ccactagtgg aggggccggt ggtaggagga gcctttggtg      5880
gagggaccgg gccctagagc gtaggtagtt attggtagtg gtcagggtcc cccgcgcggg     5940
ggcggagtgg gcgtgttctg gccgcgcctg cgcagtccac tctactcggc gggcgaagga     6000
gacgcgttaa agatggaaga cttccagggg gatccaccgg tcgccaccat ggtgagcaag      6060
ggcgaggagc tgttcaccgg ggtggtgccc atcctggtcg agctggacgg cgacgtaaac     6120
ggccacaagt tcagcgtgtc cggcgagggc gagggcgatg ccacctacgg caagctgacc     6180
ctgaagttca tctgcaccac cggcaagctg cccgtgccct ggcccaccct cgtgaccacc     6240
ctgacctacg gcgtgcagtg cttcagccgc taccccgacc acatgaagca gcacgacttc     6300
ttcaagtccg ccatgcccga aggctacgtc caggagcgca ccatcttctt caaggacgac     6360
ggcaactaca agacccgcgc cgaggtgaag ttcgagggcg acaccctggt gaaccgcatc     6420
gagctgaagg gcatcgactt caaggaggac ggcaacatcc tggggcacaa gctggagtac     6480
aactacaaca gccacaacgt ctatatcatg gccgacaagc agaagaacgg catcaaggtg     6540
aacttcaaga tccgccacaa catcgaggac ggcagcgtgc agctcgccga ccactaccag     6600
cagaacaccc ccatcggcga cggccccgtg ctgctgcccg acaaccacta cctgagcacc     6660
cagtccgccc tgagcaaaga ccccaacgag aagcgcgatc acatggtcct gctggagttc     6720
gtgaccgccg ccgggatcac tctcggcatg gacgagctgt acaagtaaag cggccgctcg     6780
ggttggactg tgagagggag ggtggcggcg agatccgggg tgtggcgggg cccggtctgg     6840
gaagacacag cttctgctca gcggccgct cgggttggac tgtgagaggg agggtggcgg     6900
cggagatccg ggtgtggcgg ggccggtct gggaagacac agcttctgct cacgccacc      6960 tggcccgagg ctgatgagcc tacacacaat tgtcaaaaa tcccacacaa tttgtcaaaa      7020
acaataataa taaaaccta acacttcctc ttttgacatt tctaaagtgt caactaagga     7080
tattctgagg gaagagtaag acatttgcat ttatcagaat ctttcagttt tggtcggtct      7140
attttcccaa cacactttc ggcagtcagg atccttttgt ttgaacgttg gcggttccct      7200
gcggacactc cgcgtcattc ccgcgtgggc ggtgcccgcg gtccgcggag actgcgctgg     7260
gctcgtgtct cggtggggtt cacgcgtcg ggaggatgac gtcactccac cccttccgca     7320
ctgctgcaga ccccagccgg gaccgaggtt gggaaaggag gcatcctgct gtggcatgta     7380
tagtgacaca ggcgcgcagg gccagctccg ggtgaccgca gtgggggtct gctgcccagt     7440
ctgtctgtct gccaaggacc gacgtgcgaa cagaacctgc ctttgtctcg gtgccgcacc     7500
ttgtccttca gtgcggcgct ccctcccacc caggccacag cgactgggta catttcattt     7560
cagtttaaga tagtaacgga atctctcatt cttgtggggg aagaatgtaa tgcctcttag     7620 tacccctagcc actcgccttg atgatgtgtt gtcaaaatgt ttttcccttc gtgctaacac    7680
gcatttgaaa aacagctgaa tggacgccag ttaaagaata gttgctcatt ttttccctga     7740
```

-continued

```
ataatctttg ttgaaactca ataaaatccc acacaatttg tcaaaaacaa taataataaa    7800
accctaacac ttcctctttt gacatttcta aagtgtcaac taaggatatt ctgagggaag    7860
agtaagacat ttgcatttat cagaatcttt cagttttggt ctattttccc aacacacttt    7920
tcggcagtca ggatcatttt gtttgaacgt tggtggaacg caagtaaaga ctctgaagcc    7980
acgattccga agcagcagca caggggatgt ttggccagac agcgatctca tgtatggctg    8040
aagattggct tttatggtag tcacagccag ctagacttta taggaaggaa atggccatgt    8100
gaaaaggtag ccctcacaac cgcgttctaa ttccagcttg tacatgtaga ctgactgaag    8160
tgaagtatcc agacagtgat ctgtgtttta cacagagtgt cagcagcagg aggacggcca    8220
ctctgcattg tttacccagc agccctctca gctgagcctt ttctacctgc ctctagctcc    8280
ccaggtttcc ctcagctcat ttccctctct ggtagcagct ggcagtgctc cctgatttca    8340
atataatttc tcttctgtta ttttcttact ctaagtgtat gggaagtgac actagggttt    8400
tgctttgtgg cttaggatca ctgtagtcac ttaggaagag cctttcagtc gacttaccct    8460
ggagagtcac cacattttca ctatttcagt gatttcggct ttgtttccaa ctgacttctt    8520
agagggtcta gcaagggaaa tggctttggg tggtcaattc tcattctcct gaagaggaag    8580
gggtgatact caatactaga acagggcagg gtccactgtg gtcagcagta agggaagtct    8640
gtagcaaaac aggactgagt gactgccgag ggaggctgtg ctatccgatc cagggcctgt    8700
ccagtgctaa ggctatccca gaacttggaa tagttcattt gttctcaggt aagaagcata    8760
ctgcaggcta gtgcctggcc aatgttttca ggaaaccctc acaccactc aaatccagta     8820
ttatgttaag aggagactaa gaaaactact tcgggcatca ccttgctgct ggcagccctc    8880
aagtcagctg atgcttcgtc ctgaagtagt tcattgggt taagaaaatg atgggcacac     8940
atgagccttt tacgtgttaa acatcctagt cattatcttt acaatgatga cttatgtttc    9000
ttcagctgct ttgtatggca gtggagtggc tcggaatatg gcacctgcac tggctaattg    9060
tgctgacagc cagctgcagg ggaaggagag acaggattct agtttgaagt gacacctggc    9120
ttgcagtgtg acactcagct gcttcacacc tctggggtct gaggttcatc tgcacagtcg    9180
acagcctgat ttctaagtct ccttcagtat ctcattgtgt gctcattgat gctctgcaga    9240
aagctctttt aaaccaaact tatctacatt ttcttcctta acagactgca tttgttgttg    9300
atgaagtgag cagcattgta aaggaggtaa gaggaaacag tcttgttttc caggcgtttg    9360
gttggtacta tgtgtcttgg agttaccatt actgtgattt aacaccatga ccacagcaat    9420
ttgaggaaca aagaagggtt tcttcagctt acacttccac atcacagttc atcatcaaag    9480
gaagtcagga taggaattc                                                 9499
```

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Junctional sequence

<400> SEQUENCE: 7
ggggatccac cggtcgccac c                                               21

<210> SEQ ID NO 8
<211> LENGTH: 251
<212> TYPE: PRT
<213> ORGANISM: Artificial Sequence
<220> FEATURE:
<223> OTHER INFORMATION: Description of Artificial Sequence: Amino acid
      sequence of modified green fluorescent protein

<400> SEQUENCE: 8

```
Met Glu Asp Phe Gln Gly Asp Pro Pro Val Ala Thr Met Val Ser Lys
1               5                   10                  15

Gly Glu Glu Leu Phe Thr Gly Val Val Pro Ile Leu Val Glu Leu Asp
            20                  25                  30

Gly Asp Val Asn Gly His Lys Phe Ser Val Ser Gly Glu Gly Glu Gly
        35                  40                  45

Asp Ala Thr Tyr Gly Lys Leu Thr Leu Lys Phe Ile Cys Thr Thr Gly
    50                  55                  60

Lys Leu Pro Val Pro Trp Pro Thr Leu Val Thr Thr Leu Thr Tyr Gly
65                  70                  75                  80

Val Gln Cys Phe Ser Arg Tyr Pro Asp His Met Lys Gln His Asp Phe
                85                  90                  95

Phe Lys Ser Ala Met Pro Glu Gly Tyr Val Gln Glu Arg Thr Ile Phe
            100                 105                 110

Phe Lys Asp Asp Gly Asn Tyr Lys Thr Arg Ala Glu Val Lys Phe Glu
        115                 120                 125

Gly Asp Thr Leu Val Asn Arg Ile Glu Leu Lys Gly Ile Asp Phe Lys
    130                 135                 140

Glu Asp Gly Asn Ile Leu Gly His Lys Leu Glu Tyr Asn Tyr Asn Ser
145                 150                 155                 160

His Asn Val Tyr Ile Met Ala Asp Lys Gln Lys Asn Gly Ile Lys Val
                165                 170                 175

Asn Phe Lys Ile Arg His Asn Ile Glu Asp Gly Ser Val Gln Leu Ala
            180                 185                 190

Asp His Tyr Gln Gln Asn Thr Pro Ile Gly Asp Gly Pro Val Leu Leu
        195                 200                 205

Pro Asp Asn His Tyr Leu Ser Thr Gln Ser Ala Leu Ser Lys Asp Pro
    210                 215                 220

Asn Glu Lys Arg Asp His Met Val Leu Leu Glu Phe Val Thr Ala Ala
225                 230                 235                 240

Gly Ile Thr Leu Gly Met Asp Glu Leu Tyr Lys
                245                 250
```

<210> SEQ ID NO 9
<211> LENGTH: 14000
<212> TYPE: DNA
<213> ORGANISM: Homo sapiens

<400> SEQUENCE: 9

```
ccctgctaca ttttttgtaat ggtgcctgtc tttgttttac agcactccat cgatcagcct    60
gattttatct ggcaattaaa aatgaataaa tcccacacca cagcaccacc tggaaggaaa    120
cattctccta cagccatgtg agaagccccc ccgacactc agccatcctg tctctgtgtc     180
acttttggag ccagacagtc tgggctcata cccagccagg actcagccac gtgctctcag    240
gccagctgct tcatctctgg gagactggcc ttcctcctcc gtgacatgga gccatccctg    300
cttcacaggg ctgtttgggg aactcactga gtcatccagg cacagcccta gagcaacagc    360
cagaacaaag caagcccgac tcaaaagggt tcttctacc cttccatctc cccttcagga    420
aggcccaaga gtaggaagtt aagccactgt tctgggattg ggagggacgc gggcagccat    480
ggggaaaact tcaatctagg tgtttccatt ggtctttatc tggtcatgct gtatcccagt    540
```

```
ggaacttcgg catccagaca aaacacagttt ggttacggca ttgagtgtgt cagttcaaca    600
ctgattttat tggcctctat gtatcaagca cgtgccagat atcgaggatc taaaaagaag    660
tgagactcaa tctctgcatt taagaaggac ccatcccagc cagaacatgg acacacagac    720
aaataactca taacatggtg ggatgagtac aaaacccaag gatcagaagg caagagtcac    780
tccacacagg agcagagagg gctggtggga ccagggaggg cttcccaggg agagacgtgt    840
gggacagctc cgccagggga ctgaaatagt cagccatgca ctaggagttt gaaacaatgc    900
ctgcttgctt tcctcagcct aacagcaaat cttgactttg gcttctaaat ctggtgaaag    960
gggaaaagta caagaaaagt aaaaccaatg aagaaaagag atgaggagga tgggaaaggg   1020
acacattgtt tattcttagg ggcccctatt tctttcatcc aatcatctat tgtctctgag   1080
cagtcagtca tcagatcaaa ggaaataaat gttcagccct ccctggtacg ggggaaacgt   1140
caccagagtg gaaatgcaga gatctgcggt agcatgagtg cgtgtgaatg tgactgtcat   1200
caccacacac gctttcaagg gaagactaca gaacgttctc aaagcccaca agccacagcc   1260
ctgcaggtca tttcaagcgg gcggcagctc gctcctgtat tgtttaccac agctatttcc   1320
ttgagaagtt tcacagcttc agcgtgcagc caccatgctt tctgcctcgt acacagggga   1380
aaagttgagt gactgcattg tccttgaaat tttacctgaa aacctcatga cttttttgct   1440
tgcatagatt cttttttttt ttctctgaga cggagttcgc tcttgttgcc caggcgggaa   1500
tgcaatggcg cgatcttggc tcaccacaac ctccgcctcc caggttcatg aaattctcct   1560
gcctcaacct cccgagtagc tgacattaca ggcatgcacc accatcctcc gctaattttg   1620 tattttagt agagacaggg tttcttcatg ttggtcaggc tggtctcaaa ctcccaacct   1680
caggtgatct gcccaccgtg gcctcccaaa gtgctgggat tacaggtgtg agccactgcg   1740
accggcctgc ttgcatagat tctttacgga agctgattac agccacaaag gaaggtgatg   1800
aataaagaac agctctcagc tcagttccct attcataggc ttaaaagact cattttttgca   1860 acaatgagac agcacgcatg catatccatc agaaagtctg acacagaaat gaagatgtgc   1920
gtttatacat tttctgtcta tcttgttact cattcagagg tgggttttct gggaagcgaa   1980
tgacacctca acttcagaat cctttatttg cacggccctg tccaaggccc tagatgccct   2040
gtacctggtt ccctctttgt tttcccaaag tctccacaag ttgtacaagt ttcaggtccc   2100
tcagatatct ctacttcaca ttagaagact cggctgggtg cggtggctca cgcctgtaat   2160
cccagcactt tgggaagctg aggtgggtgg atcacgaggt caggagtttt gagaccagcc   2220
tggccaacat ggtgaaaccc tgtctttact aaaaatacaa aaattagccg ggcatggtgg   2280
tgggcacctg taatcccagc tactcgggaa gctgagacag aattgtttga acctgggagg   2340
tggaggttgc agtgagctga gatcgcgcca ttgcactcca gcctgggtga cagagcgaga   2400
ctctgtctca aaaaaataaa taaggccggg cgtggtggct cacgcttgta atcccagcac   2460
tttgggagga cgaggcaggt ggatcatgaa gtcaggagat ggagaccatc ctggccaaca   2520
tgttaaaacc ctgtctccac taaaaataca aaaaaattag ccaggtgtgg cggcaggtgc   2580
ctatagtccc agctacttcg gaggctgagg caggagaatg gtgttaaccc gggaggcaga   2640
gcttgcagtg agctgaaatt gcagccactg cactctagcc tgggcaacag agtgagactc   2700
tgtctcaaaa aataataata ataaaataag taaataaata aacaggctgg gctcggtggc   2760
tcacacctgt aatcccaaca ctttgggagg ccgaggtggg tggatcacct gaggtcagga   2820
gtttgagacc agcctagcca acctggtgaa acctcatcta tactaaaaat acaaaaatta   2880
```

```
tctgggcatg gtggcaggca cctgtaatcc tagctaccgg ggaggctgag gcaggagaat    2940
cacttgaacc tgggaggcag gggttgcagt gaaccgagat cgtgccattg cactccagcc    3000
tgggcaacag agtgagactc catctcaaat aaataaaaaa aaataaaaat acataaaaat    3060
aaataaataa ataaataaaa cattagaaga ctcacacgtg ggcttgaatc tataaaactt    3120
gaagcctacc tgagagagga caaagttgaa caggcgcttt ctctgaaaga tcactgcaat    3180
tcaccgctga ttccgagtat tctttctcat tcggggagcc ttttaccacc caaaaacaac    3240
aaaaaatatt actttagaat cagaaatagg aattcatgac tgaaatagga agccatggca    3300
ttcatacttt aaacttgacc tctttgtatg gaagagcaaa gaaatgagaa ttaatattat    3360
tatttattta tttatttatt tatttgagat ggagtctcgc tctgtcacca ggctggagtg    3420
cagtggcgcg atctcagctc actgcaacct ccacctcccg ggttcaagca attcccctgc    3480
ctcagcctcc tgagtagctg ggactacagg cgcccgccac cacacccagc taattttttt    3540 gtattttttta gtagagtttc accatgttgg ccaggatgat ctcgatctct tgacctcatg    3600
atccatccgc ctaggcctcc caaagtgctg agatgacagg cgtgagccat cacacccggc    3660
cgagaattaa tattattata tccttctagg tactactcac aattgttgtt atgctttctg    3720
ttgtgccaac agctactatt tatttagctc ttactctgaa ccagatagtt taagtacttt    3780
gcatacatta tctctactaa tccttattgc cacattatga agtaaatgta cccattctac    3840
agatgaggag agtgagtctt ggagtgatta agtaacttac ctaaactcac actctaaact    3900
gggtctgttt aactccaaaa ccttatgctt catttaggca aagcagctaa gttagaatct    3960
ccaactatct tggctaaata atcttttcta caccaattct aatttctttt tttcttttt     4020 tgagacggag tcttactctg ttgcccaggc tggattgcag tggcaggatc ttggctcact    4080
gccacctccg cctcccaggt tcaagtgatt ctcgtgcctc agcctcctgg gcagctggga    4140
ttacaggtgc ctgccaccac acccagctaa ttttttgtatt tttttttttt ttttagagat    4200 gggtttcat catgttggcc aggctggtct caaattcctg atctcaaggg atctacccac    4260
cttggcctcc caaagtactg ggattacagg cgtgagccac cgcacccagc ccaattctaa    4320
tttaataaat ctttaatatc taatgtgcac tttcctctca tagtctcttt cttaccaagc    4380
aatttagaga ttaaggaagc ttaattaaaa gaaatttaaa ttagaccta gctaactttt     4440 ttataattcc aaaatgatat ttatgttcca cctccaaacg agaaattacg gatgatcaaa    4500
acaataaagt cgattcagag agagcaaaat agtaataaac tgtaagtata agaatttgca    4560
aaccaaagaa gaaagcaaat gacactctac cctttaaaaa aaaaaatcac accatatagc    4620
ttttggatag tgttttctg ttttgttttg gttttaatt aactctgaag tcacttccac      4680
catatcactt aaatcattat tatctcaaat gttaaatgta tgttattcaa taaaattaca    4740
agatatcttt tatctaattt attatgtttt gtttcctacc ttttcaatgt cataaattta    4800
agaaaagtta caataactat aatctctacc caccccactc ccccactcct aaaacgacct    4860
gctgcaacgg ccagccatgc cttctcatcc taccttcgca tctgcttcaa gagaagagac    4920
cagagccggc tctgcagaga aggaagtcaa ttcttcttgt tagagtaact gacgtatttc    4980
tcttcccttc ctgtcgggca caggctgacg cagtgcaccc tgtgtggcca gccttacatg    5040
cctcggtggc tactcccaca tcactaggga cccagggagc aaagccaccc caaaaccaca    5100
tcaaggagct cttctatgcc aacattttac attttttagct ggaggaaaga ccaggctgat    5160
gctggtgaaa tgtttcaccc ttcctaagga aactccctac agagactaca gccttcaaat    5220
attcaaatgt tctcacattt gtgaagggtt tcacattgac ttcagtgtaa atgactaacc    5280
```

```
acatctcaaa gaacagctat taactcaaga ataatttaca agaaagggg acagccaggc    5340 caagagcgat gaagattgta atgaaatcac caaggggaac cttcaaaatg ctgtgcgtgt    5400
actaggtagt attactcagc accgtgaagt gtccctgccc tgctaactca ggcatggcca    5460
aggacttgct ctggagagca ataagacaat gaagtgtgtg caaaggtgcc acgtgccacg    5520
taggcttggc acctaccgag ccagtactgg ggccaccatt cattctcttt cccttctctt    5580
tcccttgatg actccagaca caggctgctc agcaacctc gtctcagcat ggagaagaca    5640
tgaagcagag ccatggaaga tccttgatgg tcatggagtg tgagtggcaa ataaatgttt    5700
gctgtcatca accactgaga gtgtagggcc atttgtttct gcagctaacc tagcctattc    5760
tgctgatgta gtgtgtagtg ttttcacaaa cacagaactg agcaccaaac tatttaataa    5820
ctactatagc atgaatattt acccattgga acaaatgcca gcggaggccc tgctatacca    5880
cgagttatcc tttagttatt ggatcttggg gatgaggtcc cagggaaggg gctgcagtca    5940
ccaggattga gaggaagagg gacccaagaa gctcagagca gccactgttt catggggtac    6000
agaggtattt cagcacaact gtgcctccgc ttcccagctc aatagcagat ctaaatatag    6060
gcacttctta gctaatctct ttagcttttc tcagcacagg actctcactt tagatatgtg    6120
tcagccagag tttcttttcc tttacaacat taaattcctc agccatgagt gtttcaacag    6180
caccctcgtc ctcatcgtct tcttctgtta ctattatttt gactcagcat gatctcatag    6240
taacacactt cttggcacag gggaagaaag gaaaaaatgg aaaatccaca ggatggcatt    6300
tggactatga agggctgcag attatagcag aacaacactg ctggatatta ttattattat    6360 tattttttt tttttttttt tgagaccgag tctcgctctt tcacccagtc gggactgcag    6420
tggcgcgatc tcggctcact gcaagctccg cctcccgggt tcacgctatt ctcctgcctc    6480
agcctcccga gtagctggga ctacaggcgc ccaccaccgc acccagctaa ttttttgtat    6540
ttttagtaga tacaggggttt caccgtgtta gccaggatgg tctcgatctc ctgacctcgt    6600
gatccgcccg cctcggcctc ccaaagtgct gggattacag gcgtgagcca ccacgcctgg    6660
cctattattt tatttttga gacggagttt cgctcttgtt acccgggctg gagtgcaatg    6720
gcgctatctc agctcaccgc aatctctgcc tcctgggttc aagcgattct cctgcctcag    6780
cctcccaagt agctgggatt acaagcatgc accaccatgc ctggctaatt ttgtatttt    6840 agtagagata gggtttctcc atgttggtca ggctagtctc gaactcccga cctctggtga    6900
tctgcccacc tcagcctccc aaagtactgg gattacaggt gtgagccact gcgcccagcc    6960
actgctggat attattgatg ttatttattg atgtgacagt tcattgattg ctatgattat    7020
taggcccaca cttgctaaat aaaggtattg gcagctccag tcccacagtc tgtattcaag    7080
aaatttgact ccagaaaaga aaggtgattg cacgcaaacc tgccaaccta tcactaacct    7140
ccaaattgaa aaacaaacct aagattcact ccactgactt actgcataga aactaaacat    7200
tattctaaaa tatggcagaa tgccaaagat tcatgagcag ttacgagtaa aggtgtctga    7260
gctccaatgc ttctgatgga catccattcg tggcagatgg aaggtgctgg aaatggcatc    7320
tggtgaactg ccaaatgtct taacgatttt aaattcctta gccctacaga ctacatcagt    7380
tgggcagaat ataataccac atcactgcat ttttccaagc actacaacat cacataagcc    7440
tagagaattc aaaccctcct atttacagat atatccgttt aaagaaaaa attccataaa    7500 ggccatgttt tagtcaactt tgtagcctca accccagct cagagcctga cacaaaggga    7560
gtgctccata tatgtgtatt gaacaagtga acagatagtt gtgaagataa acagaccagc    7620
```

```
tcatccgttt actggcagcc tcaaaatgtc atacatcgcg atcatttaac aaatgttctt   7680
taatagttaa aattggagag tggtacccaa tgtataaaag ctaaaatcat gtaagcattt   7740
ttaaaatgca catttgcatg ttttctgttg atttatgtgc atgctggtga tccgcagtta   7800
taacaagatc catgcattaa ttatgcacca tcctagcaga cattcaggaa attgatttaa   7860
attaggaagt tcctaaaagg ttgtggggaa aattgaaaag gctgtcccaa gtgtcatgtt   7920
cttccattgc aggtgtttgc tcagaaccgg tttactcttg cttttgcacat aattctgtga   7980
cacttagcta ctgaactcca ggtccacaac aaagtagcag aagaaaaaag atttcagagg   8040
ctcctgattg gctcaggatc gtggtggggc caagagcttg gaaccaggta ggcagagaac   8100
atccaaaacg agatctcagg tgatactgag aagggcaggc aggcaaagca atgtcagcat   8160
cagaatcaca tgtggactga ggcgcacgac tgaaacacca ggacagggga gttgaagcca   8220
ggtaataaga aaggaattca aaaggtagat aaagttcaga atccaaggag aggaagacca   8280
ggtgtggtaa agcaaccagc ctgcccagca agtctcctcg ctcaggccga acacccaggg   8340
ccaagcagcc ttgtgtcagt cagggctctg ccctcctctc gccagccctg tttccctcaa   8400
ggaggcaggt agttgcatct tcctccactc cccagttctc tccatttggg tctgaggcaa   8460
agctaacacc catgagggaa atgattcatg caataaattt taggccgggc atggtggctc   8520
acagctataa tcccagcact tgggaggct gaggctggag gatcccttaa gcccgggagt   8580
ttgagacctg cctgggcaac acagtgagat cccatctcta caaagacat attaaaaaaa   8640
taggtgggtg tggtggctag tgcctggaat cccagctgct caggaggcta aggcaggaga   8700
ataccttgag cccaggagtt caagctctta gtggtctttg gatgactaaa cttcaacaca   8760
tcttagctca aaatctccga tcacaccact gcattccagc ccgggcaaca gaatgacacc   8820
ctgtctctaa ataaataaat aaataaatgt taattgtgta gctattatgt gccaggcaca   8880
atgtggaagg aaggggatac attagtgaat aaaacagatc cttcctgcat ggtacttagt   8940
ttctaaatgg agacacacca tcaacaagca accataaaata cgttcttgca aactgagaga   9000
agtgctatga ggaaaatgta caggatgcag gggtggagga tgaggaggtc ggctacctta   9060
gatgccgtgg tcacagaatg gctctctgta ggagattttg agctaagata tgttaaaagt   9120
ttagtcatcc aaagatcact aagattagtc tatagtctga caacttagta actattgact   9180
tatggcaggg cagaatgggt gaggggaggg aggagtcgtt gggttaggtt cctcttgaag   9240
ggctctaata agaccctgat agaccgacca ggttacagtc cgatggtcat aatccagatg   9300
agagatatca atctttaact gggtcccga gcatatgggg tagaaataac aagggttgtt   9360
gatggattag atgtgggatt tgaagtttag gtctaccaaa tccctgggac ccttgcagtc   9420
agctcttcct tggggaatgg gaagtgggtt ccagcaacct gaattcaagt gcatgacgaa   9480
accagaaaaa gcaaacgcca aaatcaaaac tcggagcctc agaatacctg ccaatagatg   9540
catatgcccc agctttccgt ggagggcagt ttaccagagc ccagtgcaat tcctaatttc   9600
cataaagaac ccacatacaa ataaagtctg tctagttcac tatggttaag gtagtcagga   9660
agtgtgccac attttacaaa attttccacc caaaatgttt ttttttaatg gtgcttaaag   9720
gaaaaattct catttacctg gaaaacttaa ctccccaaag ggaagtttcg ttcagatagc   9780
taaagcatgc caatcccagt ccccaaggga actgcaacaa cgtctcaccg ggcgcactgc   9840
cttcagcagt cactttcgag tttgttgcca ggtgtccgag cgggtttgaa cgtccgcgtc   9900
aatccacaca gtacaaaccg gaggagggc cgggaccacg cttcccctcc aggactgcct   9960
tttgtacgtg tgttttgttt ctgttgctaa ggtttaggga gctgcccggc taccctcacg   10020
```

```
gattcccatg gaaactacca cctcccagag gacaggagga gaggcgaatt cagggtccac    10080
ccacgggccc cgcccaggga tggggtcact gagggtccgg gcagcgaagg gcggggcccc    10140
ggagctgggc atgggcgagg caggcgcgag aggagagggg cgtggcaggt ccggggcggg    10200
gcctgagtgc gcctgcgcag tccgcgccac tcagggagcc ggaggggacg cgccggagga    10260
aagatggaag actaccaggc tgcggaggag gtaaccgccg ggtcggcgac ggaagggtgg    10320
aggcctagag ccctggccgc ggaaggacac gcggtcctgc ccggaaaggc ctggctgccc    10380
acctccttca gctaggccag tctcggcagc ccacggcctg agcttcccgg tcgccggcgc    10440
tccgcccggc cccattctgc ccggacattg ccgccgtttc cccggcgcgg ggggcgggaa    10500
ggggattgag cttcttcccg cgcggggagg caccgggcgt gactcggaga gagcgccccg    10560
gtgagcggtg ccgagaaacc ttcccgcagg gcctcgcctc cggcccgcag ccaagctcgc    10620
cgagaggatg acatcaccgc cccttgctct gcggggctga ccccagcccc agcccagcc    10680 tggagcgggg cgcggcggcc gggctgggag cgccgaggct tggacgtctc cccgcggagg    10740
tgcgggtgac gctcccgccg ccagcccctc cgccccgggc tggcgtcccg gccatcccgc    10800
gcctttgtct cgggcctcac ctggttctgc aacgctggga atgagtagca catttcattt    10860
ccgtttaata tgtctgtaag aaagctcatt gttgtgggga aaaaatcatc ttttatgcct    10920
ccttgaggaa gtaggataaa gcccacgatg tcgccaagca gaagacaccc atcggcaccg    10980
tgtgcgttaa atggctttcc ttcaagctca cggtcattcg gggaatagag ctgatgggcg    11040
cagctgagat acaacactca ttttcttctt actgaataat ccttgttgaa attcagatag    11100
agccctatgg atttattatg cagcctgtca aaatataaa ctatagatac atttggtaag    11160
gttggatatc ttaccattta tgaaatttag tggctgggcg cagtggctca cgcctgtaat    11220
cccagcactt tgggaggcct aggcgggcgg atcacctgag gtcaggagtt cgagagcagc    11280
ctgaccaaca tggagaaacc ccgtctcttt taaaaataca aaattagccg ggcgtggtgg    11340
cgcatgcctg taatcccagc tactcgggag gccgaggcag gagaatccct tgaacctggg    11400
aggcagaggt tgccgtgagc caagatcgcg ccattgcact ccagcctggg caacaagagc    11460
gaaactccgt ctcaaaaacc aaaaaaaaag aaaaaaattt cgtttaagga ggaatgtttt    11520
cagggaaaat aaaactaaaa cttaaggact gattctagag tttcagtttt gatctgattt    11580
cctaactagc acacacttcc tgtgacagtg gcataatcag tgtttgaatg ctgatggcaa    11640
ccaagtgaat aatgacgaga agagctggtt caggagcagt tggcaaagaa aaaagccttt    11700 cccttaaac tgttactaat ataatattgg aaaatgtctt gtattacagt aatatcgagt     11760
aaaacttcta aaaagaaat cgctttgtaa aggaaagcgc ttaatactgc agtccgattc      11820
tgactcccac aaataaggtg gctaagtggc ttcattattc gagatctcaa tcgcatatgt    11880
gtaaaatgaa ggggctggac agagtgatga gtgttctacc tgggatggag gccctgggag    11940
gtggagacca tggctgtctt gtagtaggca tgtcttaggt atttactgaa tggcccgttc    12000
tggtcctccc accagcctct tagcagcctt ttctgcatct cttctaactt cgtgtagatg    12060
cctgggcctt tgtaactatt ctctcaactc accattcatc tttcttggag acgttaaaac    12120
tatccactgg attcaataca actctgcttt ccactaaaaa ttctttaaaa tgtccctcaa    12180
cctttttcgt actgtaacca tatgggaggt gatacagtgc ctttcctttg tgattaaggt    12240
cacggtagtc acttggaagg atcctttaag cttccagaaa tgacttaatc tctaagatat    12300
tgcaaattgt tcttcactca gtgagttggt tttgtttcca agtccgactt ctgagtacag    12360
```

```
caagtgaggt ggcttcgggc agtcagctcc tgaaccccct aaaaagaaag ggcagggcct    12420
gcagtggaca gcagccagac agggaggaag actcactgcc aagtcagggt tctctgcctt    12480
gattccctca ggatgcacgt tgactgaggg ccccaggggt tgccctctcg aaggcgtgtc    12540
cagagctacg tacctttcct gggactcagc agtaacttta aacgcttgtg ctcatgtgaa    12600
gagcacattg gcaggcaagt gcctgactaa tgttattttc aggatgacct tttacccatt    12660
cagatctacc atgtgtaaaa ggaaaactat actcctggca ctagattcct gcaggcagcc    12720
cacctcctga gtcatccaga cactgacaga gaacagccat gctggcagct ggtggttagt    12780
cctggagtcg gagggcagca ctgggaaaga aaaataatta cctggagata atgtaatcat    12840
cgtacatttt acaagtaatg gtgctttaaa aaaatctcct caaggtcaaa ctgatcctcc    12900
taatcagttt acatcatgga agagagaatt acatcttaaa tggattactt cagcagcttc    12960
agttaattta tacaaaaatc aaccaactca ttaagcctct ctattggtta atgattctag    13020
cagccagttg aaatggaaga agagaatgaa ttctagttta aagtgaagtc ttagattgtg    13080
gcatgattaa aacaaaacag gccaggtgt ggtggcttac gcctgtaatc ccagcatttt    13140
gggaggctga ggcgggagga tcacctgagg tcaggagttc gagaccagcc tggccaacat    13200
gatgaaaccc catctctact aaaaatacga aaattagccg ggtgtggtgg agggcacctg    13260
taatcccagc tacttgggag gctgaggcag gagaatcact tgaacctggg aggcagagat    13320
tgcagtgagc tgagattgcg ccactgcatt ccagcctggg ctacagagcg acactccgtc    13380
tcaaaaataa ataaataaaa ataaaacaat acctttaaat tatgtgcatg tattctagtc    13440
ttctggtttc tgaagactgt aatgccatcc ttggtaaagc tgaacagtct agttagatta    13500
tttctaaggt cttcatttct acattatgtt cattacctac atttgcattt atcaatgtag    13560
tggaaatatc ttttaaataa atcaaactta actgaatgtt cttccttaca gactgctttt    13620
gttgttgatg aagtgagcaa cattgtaaaa gaggtaagag gagaaatgct cacttcttaa    13680
atgtttaatg gcttatatta gagaaaataa tgtgttttaa atactatctt ggaattgttt    13740
cgactgagtc tgtgtgtttt ggtgtttcaa ataacagttt ttacttcagt aaatagctag    13800
ataagagttg cttctatatt atgtaaatta catatttaa atcagataag gagttttatg    13860
tacatagcat tattactgca tatcaccaag atttgattct ataatctttt aagcataaaa    13920
gaatcctggt atacaaataa atgtctccag ggttgaatga agaaagagtg agtataagaa    13980
aattgaacaa tcaatttcca                                                14000

<210> SEQ ID NO 10
<211> LENGTH: 9
<212> TYPE: PRT
<213> ORGANISM: Homo sapiens

<400> SEQUENCE: 10

Met Glu Asp Tyr Gln Ala Ala Glu Glu
1               5

<210> SEQ ID NO 11
<211> LENGTH: 14
<212> TYPE: PRT
<213> ORGANISM: Homo sapiens

<400> SEQUENCE: 11

Thr Ala Phe Val Val Asp Glu Val Ser Asn Ile Val Lys Glu
1               5                   10
```

TCTEX-1 REGULATORY SEQUENCE AS STEM CELL MARKER

STATEMENT REGARDING FEDERALLY SPONSORED RESEARCH OR DEVELOPMENT

This invention was made with government support under Contract No. EY11307 awarded by the National Institutes of Health. The government has certain rights in the invention.

CROSS-REFERENCE TO RELATED APPLICATIONS

This application claims the benefit of priority of U.S. Provisional Application No. 61/243,841, filed Sep. 18, 2009, the entire contents of which is hereby incorporated by reference.

INCORPORATION BY REFERENCE OF SEQUENCE LISTING

The Sequence Listing in the ASCII text filed, named as SequenceListing.txt of 68600 bytes, created on Mar. 19, 2012, and submitted to the United States Patent and Trademark Office via EFS-Web, is incorporated herein by reference.

BACKGROUND OF THE DISCLOSURE

This disclosure relates to an isolated genetic regulatory sequence specific to neural progenitor cells and methods to use said regulatory sequence to mark, isolate, and manipulate neural progenitors.

Stem cell research in the central nervous system holds great promise for the development of novel therapies for brain damage and other human diseases. Researchers are keenly interested in adult stem cells because they do not pose the ethical questions raised by embryonic stem cells. One of the ultimate goals in adult stem cell research is to better understand the biology of these cells so that scientists may develop strategies to directly manipulate them within the damaged brain.

In the dentate gyrus (DG) of the hippocampus, new neurons continue to be born from resident stem/progenitor cells at the subgranular zone (SGZ) throughout our lives (Altman and Das, 1965; Cameron et al., 1993; Eriksson et al., 1998; Kornack and Rakic, 1999). Adult-generated granular neurons are indistinguishable from neighboring granular neurons in terms of their morphology, synaptic connections, and electrophysiological properties (Cameron et al., 1993; Hastings and Gould, 1999; Markakis and Gage, 1999; van Praag et al., 2002). Thus, it is likely that these adult-generated cells functionally participate in learning and memory.

At least three partially overlapping cell populations have been identified at adult SGZ based on their distinct morphologies and expression of molecular markers (Ehninger and Kempermann, 2008; Zhao et al., 2008). Type-1 progenitors (or neural stem-like cells, Type B cells (Seri et al., 2001)), which rarely divide, can be identified by their expression of glial fibrillary acidic protein (GFAP) and nestin (Fukuda et al., 2003) and by their radial processes with highly elaborated arbors branching into the molecular layers (Mignone et al., 2004). A nuclear transcription protein Sox2 has also been recognized as a marker for mainly Type-1 cells (Steiner et al., 2006). There are at least two types of transient amplifying progenitors. Type-2 cells (or Type D cells (Seri et al., 2001)), are most highly proliferative cells at SGZ, have short horizontal processes; they express transcription factor Tbr2 (T-box brain gene 2) (Hodge et al., 2008) and low-level neuronal-lineage markers such as doublecortin (DCX). Type-3 progenitors represent slow-proliferating cells committed to the neural fate, and during their transit to exit cell cycle to become postmitotic neurons. These cells are highly variable in morphology and often have vertically orientated processes displaying DCX, polysialylated neural cell adhesion molecule, and TuJ1. Whereas the identity of the neural stem cells in the adult DG has been under debate (Garcia et al., 2004; Palmer et al., 1997; Seaberg and van der Kooy, 2002; Seri et al., 2001), the prevailing model has been that type-1 progenitors represent the primary precursors that give rise to transient amplifying progenitors, which subsequently differentiate into both astroglials and granule neurons (Seri et al., 2004; Seri et al., 2001).

Regulatory sequence-targeted selection has provided proof-in-principle that high-yield and high-purity of neural-lineage specific progenitors can be isolated from the adult hippocampus. However, the previously-described regulatory sequences have poor tissue-specificity. For example, the Tα-tubulin promoter also targets to neurons; GFAP promoter also targets to astroglials.

Despite the emphasis on characterizing and utilizing neural stem cells, many studies have shown that the cycling Type 2 and Type 3 progenitors, but not the Type 1 progenitors, are most responsive to various regulatory influences (Jessberger et al., 2005; Kempermann et al., 1998; Kronenberg et al., 2003) and thus are excellent candidates for manipulation and use in research, development, and medicine.

It has been recently discovered that Tctex-1 (or DYNLT1 (Pfister et al., 2005)), previously recognized as a light chain of cytoplasmic dynein (King et al., 1996), is selectively enriched in stem-like cells and cycling progenitors, but not in mature granule cells and astrocytes, in the adult dentate gyrus (DG) (Chuang et al., 2001; Dedesma et al., 2006). The SGZ-enriched Tctex-1 expression pattern was confirmed by in situ hybridization, suggesting that Tctex-1 expression is primarily regulated at the transcriptional level. Disclosed herein are the genomic sequences specifying Tctex-1 expression in the dentate progenitors of adult hippocampus and Tctex-1:GFP reporter mice in which the adult hippocampal stem-like and progenitor cells are genetically marked.

Disclosed are the genomic sequences specifying Tctex-1 expression in neural progenitors. Further disclosed are Tctex-1-GFP reporter constructs and mice in which neural progenitors and stem cells are marked.

SUMMARY OF THE DISCLOSURE

Disclosed is an isolated regulatory sequence for Tctex-1 that is transcriptionally active in neural progenitor cells, including Type 1, Type 2 and Type 3 progenitor cells. Disclosed is a method of selectively expressing a nucleic acid of interest in said cells by introducing an effector sequence under control of said regulatory sequence into a cell population; the effector sequence can be siRNA, an antisense molecule, microRNA, an apatamer, or a sequence encoding an effector protein of interest.

Further disclosed is a method of marking said cells by introducing a marker under control of said regulatory sequence into said cell population to allow selective harvesting of neural progenitor cells. The disclosure also relates to the content and properties of such cell population harvested from the brain.

In addition, the disclosure relates to a method of assessing the changes in levels of neural progenitors and stem cells within a cell population by introducing a marker under control of said regulatory sequence into said cell population and measuring spatial and temporal changes in that marker between different conditions. In one embodiment, the different conditions are a neural disease and a normal control.

BRIEF DESCRIPTION OF THE DRAWINGS

FIG. 8. Schematic depicting the estimated timeline of the expression of specific markers and reporters at adult SGZ.

Figure 9A:
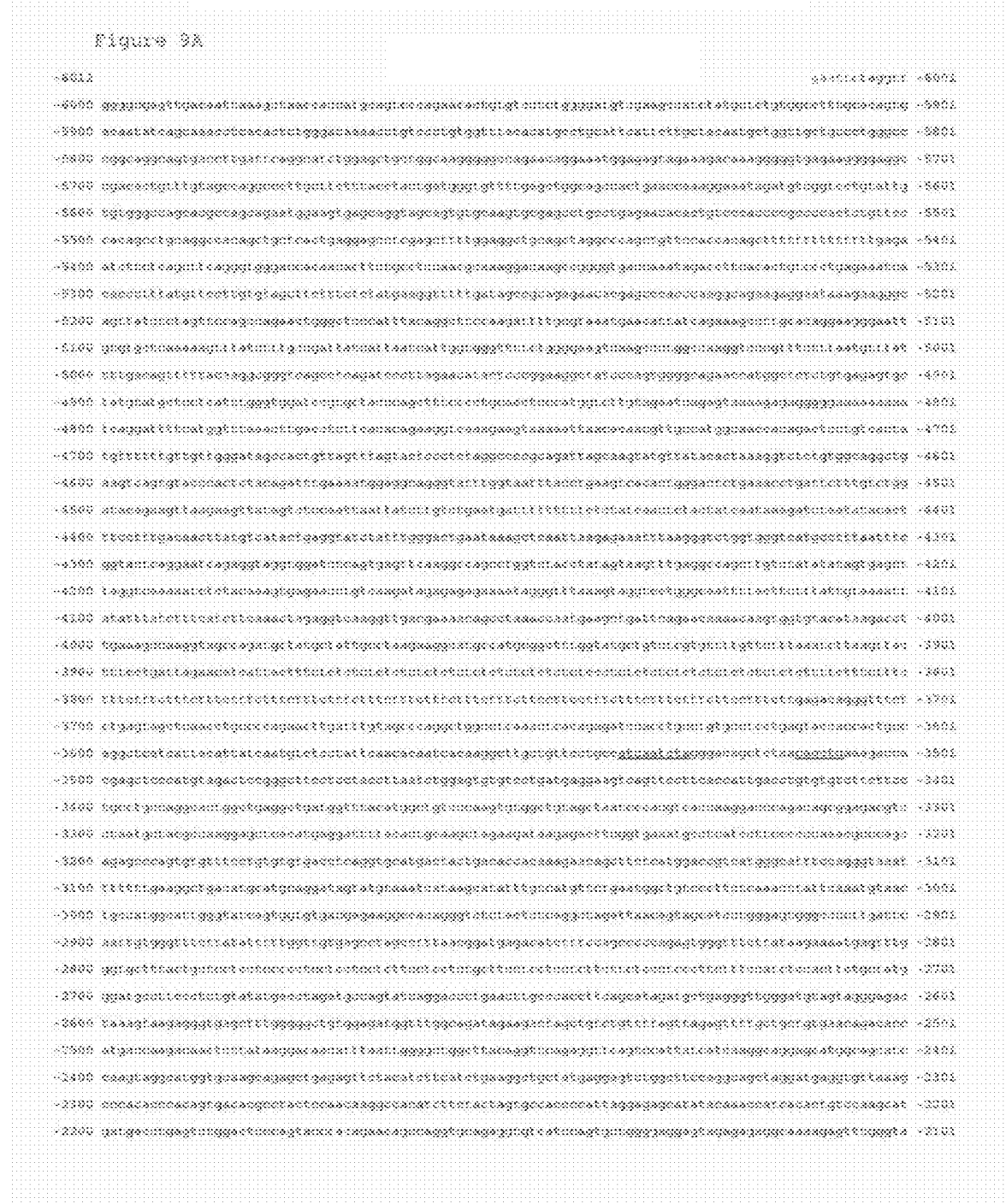
Figure 9B:
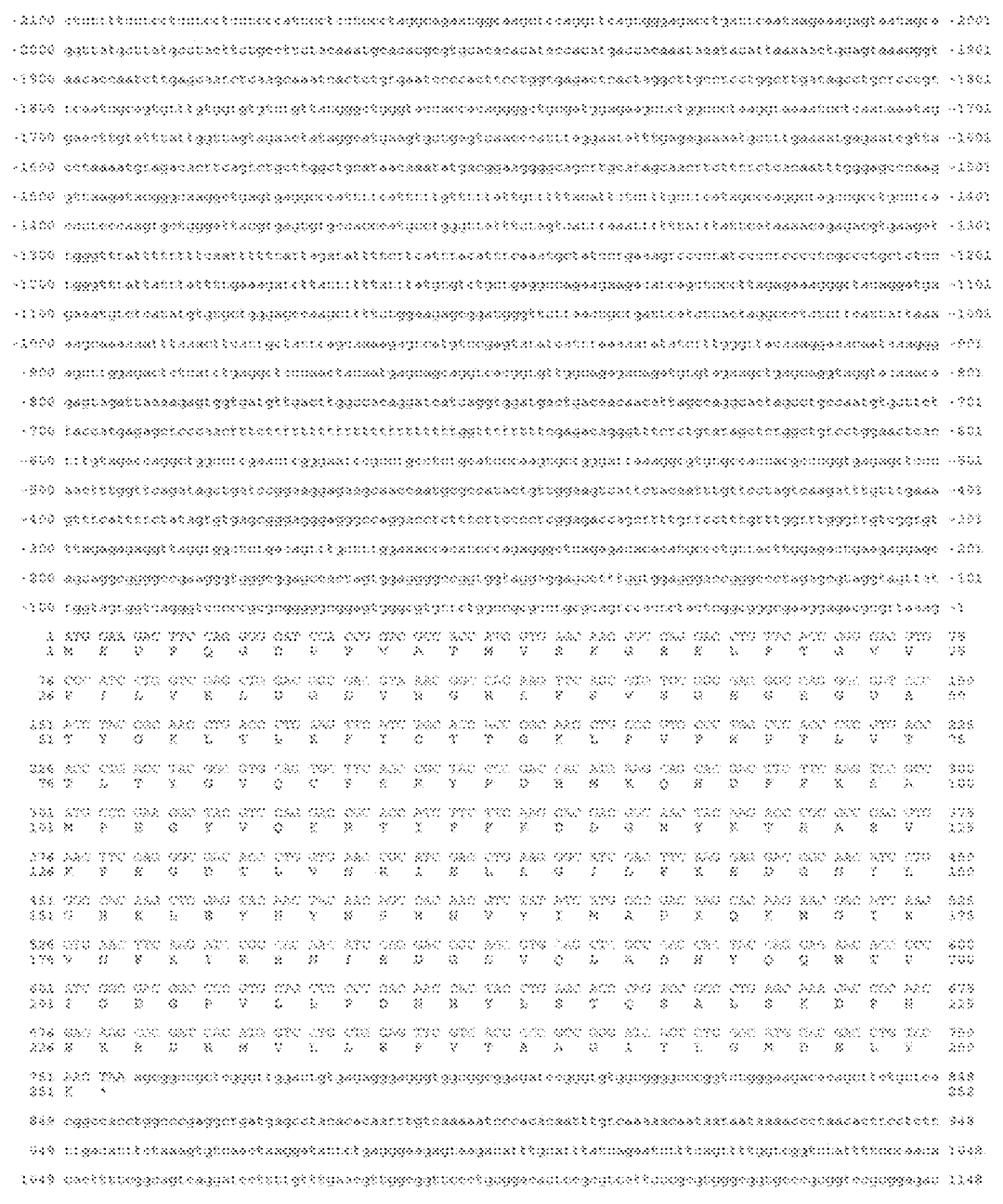

FIG. 9 (presented herein as FIGS. 9A-C). The nucleotide sequence of a synthetic construct including the nucleotide sequence of mouse Tctex-1 regulatory sequence and the nucleotide sequence encoding a modified green fluorescent protein (SEQ ID NO: 6). The six nucleotides set forth at the 5' end and the six nucleotides set forth at the 3' end are endonuclease restriction sites. The nucleotide sequence 5'-GGG-GATCCACCGGTCGCCACC-3' (SEQ ID NO: 7) is a junctional sequence. The amino acid sequence of the modified green fluorescent protein is also set forth (SEQ ID NO: 8).

DETAILED DESCRIPTION OF THE DISCLOSURE

Figure 1:
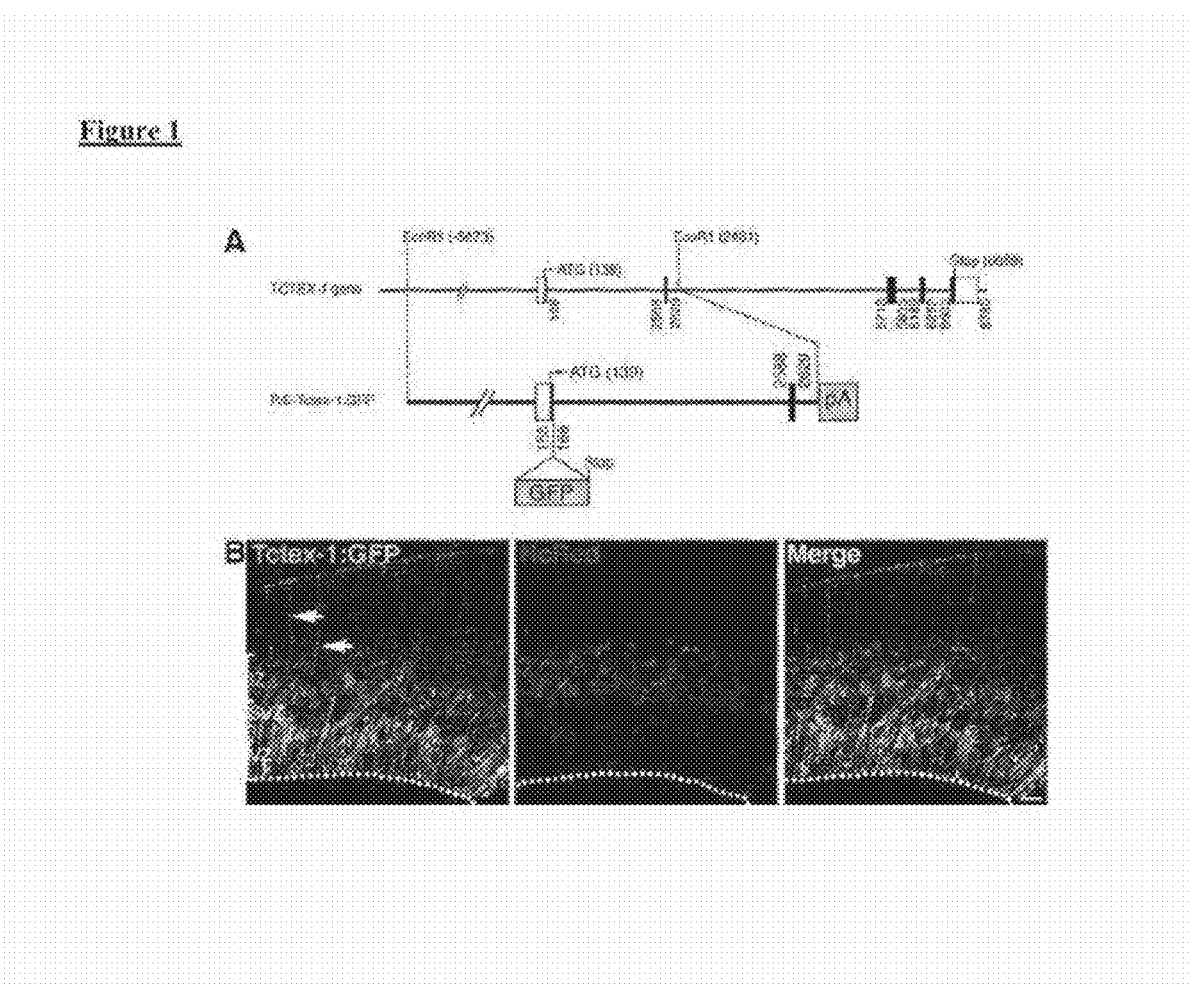
FIG. 1. Identification of the regulatory element of the Tctex-1 gene that specifically targets the VZ/SVZ of developing neocortex. (A) Schematic diagrams of the mouse TCTEX-1 gene (top) and PIE-Tctex-1:GFP report construct that encoded GFP fused 3' to the first 5 residues of Tctex-1 (bottom). Exons are represented by boxes; the horizontal line represents introns; base 1 starts at the first nucleotide of the exon 1; ATG: start codon; pA: rabbit beta-globin poly A, derived from pCAG vector. (B) Confocal images of cortical slices co-transfected with PIE-Tctex-1:GFP (green) and pCAG-HcRed (red). Dotted lines mark the ventricular borders. Arrows point to the radial glial fibers with their endfeet contacting both the ventricular and the pial surfaces. Bar=50 µm.

In the following description, reference is made to the accompanying drawings that form a part hereof, and in which is shown by way of illustration specific embodiments which may be made and used. These embodiments are described in detail to enable those skilled in the art to practice the invention, and it is to be understood that other embodiments may be made and used, and that structural and logical changes may be made without departing from the scope of the present disclosure. The following description of exemplary embodiments is, therefore, not to be taken in a limited sense, and the scope of the present invention is defined by the appended claims.

DEFINITIONS

For convenience, certain terms employed in the specification are collected here. These definitions should be read in light of the entire disclosure and understood as by a person of skill in the art.

The articles "a" and "an" are used herein to refer to one or to more than one (i.e., to at least one) of the grammatical object of the article. By way of example, "an element" means one element or more than one element.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

A "fusion protein" or "fusion polypeptide" refers to a chimeric protein as that term is known in the art and may be constructed using methods known in the art. In many examples of fusion proteins, there are two different polypeptide sequences, and in certain cases, there may be more. The sequences may be linked in frame. A fusion protein may include a domain which is found (albeit in a different protein) in an organism which also expresses the first protein, or it may be an "interspecies", "intergenic", etc. fusion expressed by different kinds of organisms. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. The fusion polypeptides may be fused to the N-terminus, the C-terminus, or the N- and C-terminus of the first polypeptide. Exemplary fusion proteins include polypeptides comprising a glutathione S-transferase tag (GST-tag), histidine tag (His-tag), an immunoglobulin domain, an immunoglobulin binding domain, or a fluorescent protein.

The term "isolated polypeptide" refers to a polypeptide, in certain embodiments prepared from recombinant DNA or RNA, or of synthetic origin, or some combination thereof, which (1) is not associated with proteins with which it is normally found in nature, (2) is isolated from the cell in which it is normally found, (3) is isolated essentially free of other proteins from the same cellular source, (4) is expressed by a cell of a different species, or (5) is not found in nature.

The term "isolated nucleic acid" refers to a polynucleotide of genomic, cDNA, or synthetic origin or some combination thereof, which (1) is not associated with the cell in which the polynucleotide is found in nature, or (2) the nucleotide sequence of the polynucleotide is operably linked to the nucleotide sequence of another polynucleotide, provided that the two nucleotide sequences are not operably linked in nature.

The term "mammal" is known in the art, and exemplary mammals include humans, primates, bovids (e.g., a cow), pigs, canids (e.g., a dog), felids (e.g., a cat), and rodents (e.g., mice and rats).

The term "marker" is known in the art and as used herein with respect to a nucleic acid sequence, does not mean a DNA sequence present on the chromosome of a cell, generally possessing introns, as is often meant by the word "gene" in the art. Rather, the term "marker" means any DNA sequence encoding a protein, a polypeptide, or a nucleic acid, provided that the presence of the encoded protein, polypeptide, or nucleic acid that can be detected or measured. The protein, polypeptide, or nucleic acid which the marker encodes may also be recognized by a reagent such as an antibody, as is known in the art.

The term "modulation," when used in reference to a functional property, a biological activity, or a biological process (e.g., enzyme activity or receptor binding), refers to the capacity to either up-regulate (e.g., activate or stimulate), down-regulate (e.g., inhibit or suppress) or otherwise change a quality or quantity of such functional property, biological activity or biological process.

The term "modulator" refers to a polypeptide, a nucleic acid, a macromolecule, a complex, a molecule, a small molecule, a compound, a species, or the like (naturally-occurring or non-naturally-occurring), or an extract made from biological materials such as bacterial cells, plant cells or tissues, fungal cells, or animal cells or tissues, that may be capable of causing modulation. Modulators may be evaluated for potential activity as inhibitors or activators (directly or indirectly) of a functional property, a biological activity, or a biological process, or a combination of them, (e.g., as an agonist, a partial antagonist, a partial agonist, an inverse agonist, an antagonist, an anti-microbial agent, an inhibitor of microbial infection or proliferation, and the like) by inclusion in assays. In such assays, many modulators may be screened simultaneously. The activity of a modulator may be known, unknown or partially known.

The term "neural" refers to the central and peripheral nervous systems. Examples of cells of the nervous system include neurons and glial cells. Examples of glial cells including oligodendrocytes and astrocytes in the central and peripheral nervous systems.

The term "neural disease, disorder, or condition" refers to a disturbance of function, structure, or both, of the nervous system resulting from, for example, a genetic or embryonic failure in development or from exogenous factors such as poison, trauma, or disease of the nervous system. For example, nervous system disorders include, but are not limited to, stroke (both acute and chronic), spinal cord injury, traumatic injury to the brain or spinal cord, traumatic injury to the brain and the spinal cord, multiple sclerosis, amyotrophic lateral sclerosis, the paroxysmal disorders (e.g., the epilepsies), autonomic nervous system dysfunction (e.g., arterial hypertension), movement disorders (e.g., hyperkinetic disorders, dyskinesias such as resting tremor, basal ganglia hyperkinetic disorders, e.g., Huntington's chorea and hemiballismus, neuropsychiatric disorders, e.g., mania, psychosis, obsessive compulsive disorder, and addiction, Alzheimer's disease, Parkinson's disease, hypothalamic disorders such as hyperlactemia, craniopharyngioma, gondotrophin deficiency, growth hormone deficiency, vassopressin deficiency, prolactinomas, obesity, neuropathic pain syndromes, acrodynia, Charcot-Marie-Tooth disease, diabetic neuropathies, nerve compression syndromes, neuralgias, neuromuscular junction diseases, POEMS syndrome, optical nerve injury diseases (e.g., glaucoma), olfactory disorders such as anosmia, hyponosmia, hypernosmia and impaired olfactory learning and memory and various retinal degenerative diseases (e.g., retinitis pigmentosa, macular degeneration). The term "neural disease, disorder, or condition" also refers to a disease, disorder, or condition related to a deficit or surplus of neurogenesis or of neurite outgrowth at any stage of development, including learning disorders, and other disorders of memory such as dementias and post traumatic stress disorder as well as mood disorders, including anxiety disorders and depressive disorders.

The term "neurite" refers to any process growing out of a neuron. The term neurite as used herein encompasses all such cell processes (including both axon and dendrite) growing out of a neuron.

The term "neurite outgrowth," refers to the process of a cell growing out of a neuron, or to the cells whose individual processes form an outgrowth from a neuron.

The term "nucleic acid" refers to a polymeric form of nucleotides, whether ribonucleotides, deoxynucleotides, or modified forms of either type of nucleotide. The term should also be understood to include analogs of either RNA or DNA made from nucleotide analogs. In certain embodiments the nucleotide sequence of the nucleic acid may be sense or antisense with respect to a gene of interest. In certain embodiments, a first nucleic acid and a second nucleic acid, which has a nucleotide sequence at least partially complementary with the nucleotide sequence of the first nucleic acid, may form a double-stranded structure. In certain other embodiments, a single nucleic acid whose nucleotide sequence has one portion at least partially complementary to a second portion may form a double-stranded structure.

The term "operably linked", when describing the relationship between two nucleotide sequences, refers to a juxtaposition wherein the nucleotide sequences are in a relationship permitting them to function in their intended manner. For example, a control sequence "operably linked" to a coding sequence is juxtaposed in such a way that expression of the coding sequence is achieved under conditions compatible with the control sequences, such as when the appropriate molecules (e.g., inducers and polymerases) are bound to the control or regulatory sequence(s).

A "patient," "subject" or "host" is intended to include human and non-human animals. Non-human animals includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses. The "patient," "subject," or "host" may also be a livestock animal such as, cattle, swine, sheep, poultry, and horses, or domestic animals, such as dogs and cats. The "patient," "subject," or "host" may be male or female, may be elderly, and may be an adult, adolescent, child, or infant. The term "juvenile" shall refer to infants, children, adolescents, or any organism from the time between its birth and the maturation of its nervous system. The human "patient" or "subject" may be Caucasian, or of African, Asian, Semitic, or of other racial backgrounds, or a mixture of such racial backgrounds. Preferred "patients" or "subjects" include humans suffering from or at risk for the neural diseases, conditions, and disorders described herein.

The phrase "pharmaceutically acceptable," in reference to a pharmaceutical composition, refers to those compositions and dosages thereof within the scope of sound medical judgment, suitable for use in contact with the tissues of humans and animals without excessive toxicity, irritation, allergic response, or other problem or complication, commensurate with a reasonable benefit/risk ratio.

The phrase "pharmaceutically acceptable carrier" means a pharmaceutically acceptable material, composition, or vehicle, such as a liquid or solid filler, diluent, excipient, solvent, or encapsulating material, involved in carrying or transporting any supplement or composition, or component thereof, from one organ, or portion of the body, to another organ, or portion of the body. The term "pharmaceutically acceptable carrier" refers to a carrier that is "acceptable" in the sense of being compatible with the other ingredients of a pharmaceutical composition and not deleterious to the recipient thereof. Some examples of materials which may serve as "pharmaceutically acceptable carriers" include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "polypeptide," "protein," and "peptide" are used interchangeably herein. The term "polypeptide" refers to a polymer of amino acid residues. Exemplary polypeptides include gene products, naturally-occurring proteins, homologs, orthologs, paralogs, fragments, and other equivalents, variants and analogs of the foregoing.

The terms "polypeptide fragment" or "fragment", when used in reference to a reference polypeptide, refers to a polypeptide in which amino acid residues are absent as compared to a reference polypeptide itself, but wherein the amino acid sequence that is present is usually identical to the corresponding positions in the reference polypeptide. With respect to the reference polypeptide, such deletions may occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. A fragment can retain one or more of the biological activities of the reference polypeptide. Further, fragments can include a sub-fragment of a specific region, which sub-fragment retains a function of the region from which it is derived.

The term "progenitor" when used in reference to a type of cell, refers to cells that are not fully differentiated. Differentiation of progenitor cells occur both in response to the body's normal attrition of cells and in response to tissue injury. Progenitors can be at various stages of differentiation and can be unipotent, multipotent, pluripotent, or can divide indefinitely. Disclosed progenitor cells include Satellite cells in muscles, Angioblasts, or Endothelial progenitor cells (EP) and others. Also disclosed are neural stem-like cells of the central nervous system, which rarely divide and have elaborated structure, and transient amplifying progenitors of the central nervous system, which are more proliferative and variable in morphology. In some embodiments, progenitors that are less differentiated, that are "stem-like" and/or multipotent, are difficult to distinguish from stem cells in situ.

The term "purified," in reference to a substance of interest, refers to the fact that the substance of interest is the predominant substance present in a preparation (i.e., on a molar basis it is more abundant than any other substance in the preparation). A "purified fraction" is a preparation wherein the substance of interest represents at least about 50 percent (on a molar basis) of all other substances present. In making the determination of the purity of a in solution or dispersion, the solvent or matrix in which the substance is dissolved or dispersed is usually not included in such determination; instead, only the substance (including the one of interest) dissolved or dispersed are taken into account. Generally, a purified composition will have one substance that comprises more than about 80 percent of all substances present in the composition, more than about 85%, 90%, 95%, 99% or more of all substances present. The substance of interest may be purified to essential homogeneity (i.e., contaminant substances cannot be detected in the composition by conventional detection methods) wherein the composition essentially contains only one substance. A skilled artisan may purify a disclosed polypeptide using standard techniques for protein purification in light of the disclosures herein. Purity of a polypeptide may be determined by a number of methods known to those of skill in the art, including for example, amino-terminal amino acid sequence analysis, gel electrophoresis and mass-spectrometry analysis.

The term "selectively" refers to activity within a subpopulation. For example, "selective expression" of a protein of interest refers to the expression of the protein of interest by a subpopulation of cells in a cell population.

The terms "recombinant protein" or "recombinant polypeptide" refer to a polypeptide which is produced by recombinant DNA techniques. An example of such techniques includes the case when DNA encoding an expressed protein is inserted into a suitable expression vector which is in turn used to transform a host cell to produce the protein or polypeptide encoded by the DNA.

The term "regulatory sequence" is a generic term used throughout the specification to refer to polynucleotide sequences, such as initiation signals, enhancers, regulators and promoters, that are necessary or desirable to affect the expression of coding and non-coding sequences to which they are operably linked. Exemplary regulatory sequences are described in Goeddel; *Gene Expression Technology: Methods in Enzymology*, Academic Press, San Diego, Calif. (1990), and include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. The nature and use of such control sequences may differ depending upon the host organism. In prokaryotes, such regulatory sequences generally include promoter, ribosomal binding site, and transcription termination sequences. The term "regulatory sequence" is intended to include, at a minimum, components whose presence may influence expression, and may also include additional components whose presence is advantageous, for example, leader sequences and fusion partner sequences. In certain embodiments, transcription of a polynucleotide sequence is under the control of a promoter sequence (or other regulatory sequence) which controls the expression of the polynucleotide in a cell-type in which expression is intended. It will also be understood that the polynucleotide can be under the control of regulatory sequences which are the same or different from those sequences which control expression of the naturally-occurring form of the polynucleotide. In one embodiment, the regulatory sequence is an isolated nucleic acid having a nucleotide sequence of the Tctex-1 regulatory sequence.

The term "sequence homology" refers to the proportion of base matches between two nucleotide sequences or the proportion of amino acid matches between two amino acid sequences. When sequence homology is expressed as a percentage, e.g., 50%, the percentage denotes the proportion of matches in a portion of one sequence in comparison to a portion of another sequence. Gaps (in either of the two sequences) are permitted to maximize matching; gap lengths of 15 bases or less are usually used, 6 bases or less are used more frequently, with 2 bases or less used even more frequently. The term "sequence identity" means that sequences are identical (i.e., on a nucleotide-by-nucleotide basis for nucleic acids or amino-acid-by-amino-acid basis for polypeptides) over a window of comparison. The term "percentage of sequence identity" is calculated by comparing two optimally aligned sequences over the comparison window, determining the number of positions at which the identical amino acids occurs in both sequences to yield the number of matched positions, dividing the number of matched positions by the total number of positions in the comparison window, and multiplying the result by 100 to yield the percentage of sequence identity. Methods to calculate sequence identity are known to those of skill in the art and described in further detail below.

The phrases "systemic administration," "administered systemically," "peripheral administration," and "administered peripherally" mean the administration of a substance, supplement, composition, therapeutic or other material to a patient, subject, or host, other than by direct administration into the central nervous system, such that the substance is subject to metabolic and other like processes. In one embodiment, the administration is by subcutaneous administration.

The term "Tctex-1" is an abbreviation for "t-complex-associated-testis-expressed 1" or "T-complex testis-specific protein 1." Both terms are used interchangeably by those of skill in the art. Other terms used by those of skill in the art to refer to human Tctex-1 proteins include "CAG33212", "TCTEL1", "AAB03318" and "CW-1p." The term includes mutated Tctex-1 proteins as described in PCT International Publication No. WO/2007/005733, published Jan. 11, 2007, which is hereby incorporated by reference in its entirety.

The term "therapeutically effective amount" refers to that amount of a modulator, drug or other molecule which is sufficient to effect treatment when administered to a patient or subject in need of such treatment. The therapeutically effective amount will vary depending upon the subject and disease condition being treated, the weight and age of the patient or subject, the severity of the disease condition, the manner of administration and the like, which can readily be determined by one of ordinary skill in the art.

The term "treating" as used herein is intended to encompass curing as well as ameliorating at least one symptom of a condition or disease.

The term "vector" refers to a nucleic acid capable of transporting another nucleic acid to which it has been linked. In one embodiment, the vector is an episome, i.e., a nucleic acid capable of extra-chromosomal replication. Other disclosed vectors include those capable of autonomous replication and expression of nucleic acids to which they are linked. Vectors capable of directing the expression of genes to which they are operatively linked are referred to herein as "expression vectors". In general, expression vectors in recombinant DNA techniques are often in the form of "plasmids" which refer to circular double-stranded DNA molecules which, in their vector form, are not bound to the chromosome. Infectious expression vectors, such as recombinant baculoviruses, are used to express proteins in cultured cells. Other infectious expression vectors, such as recombinant adenoviruses and vaccinia viruses, are used as vaccines to express foreign antigens in vacinees. However, the invention is intended to include such other forms of expression vectors which serve equivalent functions and which become known in the art subsequently hereto.

Unless otherwise indicated, all numbers expressing quantities of ingredients, reaction conditions, and so forth are to be understood as being modified in all instances by the term "about." Accordingly, unless indicated to the contrary, the exact numerical parameters may vary depending upon the particular embodiment.

Tctex-1 immunoreactivity is selectively enriched in proliferating neural progenitors and stem cells, but not mature neurons, in the germinal zones of adult brain. Disclosed is a regulatory region of the Tctex-1 gene that is capable of directing transgene expression that recapitulates the spatial and temporal expression pattern of endogenous Tctex-1. In some embodiments, the length of the Tctex-1 regulatory sequence is about 1 kbp, about 2 kbp, about 3 kbp, about 4 kbp, 5 kbp, about 6 kbp, about 7 kbp, about 8 kbp, about 9 kbp, about 10 kbp, about 11 kbp, about 12 kbp, about 13 kbp, about 14 kbp, and about 15 kbp. In some embodiments, the length of the Tctex-1 regulatory sequence is about 6 kbp to about 10 kbp. In some embodiments, the length of the Tctex-1 regulatory sequence is about 9 kbp to about 11 kbp, about 8 kbp to about 12 kbp, about 7 kbp to about 13 kbp, about 6 kbp to about 14 kbp, and about 5 kbp to about 15 kbp. In some embodiments, the length of the Tctex-1 regulatory sequence is about 5 kbp to about 7 kbp, about 4 kbp to about 8 kbp, about 3 kbp to about 9 kbp, about 2 kbp to about 10 kbp, and about 1 kbp to about 11 kbp.

The green fluorescent protein (GFP) reporter gene was placed under the control of 6 kb of 5' upstream sequence, 2 kb of intron 1, and 0.2 kb of intron 2 of mouse Tctex-1. This construct specifically targets expression to the nestin+/Pax6+/GLAST+ radial glial cells and Tbr2+ intermediate progenitors when delivered to developing mouse neocortex via in utero electroporation. Characterization of mice transgenically expressing GFP under the same regulatory element demonstrated that the GFP expression is faithful to endogenous Tctex-1 at the subgranular zone (SGZ) of dentate gyrus, ventricular/subventricular zone of lateral ventricles, and ependymal layer of 3rd ventricle of adult brains. Immunolocalization and bromodeoxyuridine incorporation studies of adult SGZ in four independent mouse lines demonstrated that Tctex-1:GFP reporter selectively marks nestin+/GFAP+/Sox2+ neural stem-like cells in two mouse lines (4 and 13). In two other mouse lines (17 and 18), Tctex-1:GFP was selectively expressed in type-2 and type-3 transient amplifying progenitors and a small subset of young neuronal progeny. The P/E-Tctex-1 reporter mouse studies independently confirmed the specific enrichment of Tctex-1 at adult SGZ stem/progenitor cells. Furthermore, these studies indicate that an analogous transcriptional program may be used to regulate neurogenesis in embryonic cerebral cortex and adult hippocampus.

Tctex-1 Genomic Sequences Specifying GFP Reporter Expression in Neural Stem and Progenitor Cells in Developing Neocortex A recent report suggested that a similar transcriptional program may control neurogenesis in both adult SGZ and in embryonic cerebral cortex (Hodge et al., 2008). Therefore the genomic region of Tctex-1 was searched for a sequence that can direct selective adult SGZ expression by using developing neocortex as an expression model system because the IUE model permits rapid delivery of reporter genes into neocortex (Saito and Nakatsuji, 2001; Tabata and Nakajima, 2001). Based on the alignment of Tctex-1 genes of different species, a GFP reporter construct was designed and generated, in which the GFP cDNA driven by an evolutionally-conserved ~6-kb 5'-upstream, ~2-kb intron 1 and ~0.2 kb intron 2 segment of mouse Tctex-1, which we dubbed P/E-Tctex-1:GFP (FIG. 1A).

The P/E-Tctex-1:GFP plasmid, along with a control reporter plasmid (CAG promoter-directed HcRed), were co-transfected into embryonic day 13.5 mouse neocortices via interuterine electroporation ("IUE"). Confocal examination of the cortical sections harvested 40 hrs after transfection demonstrated that a large fraction of HcRed transfected cells with strong red fluorescence resemble post-mitotic young neurons; they had developed multi-polar process and migrated into the intermediate zone (IZ). The remainder HcRed+ cells at the ventricular zone (VZ) and subventricular zone (SVZ) exhibited much weaker red fluorescence, indicating attenuated promoter activity (FIG. 1B). In contrast, the cell bodies of the large majority of GFP-expressing cells were distributed throughout the VZ and SVZ zones (FIG. 1B). Many of these cells bore features of radial glial (RG) cells, displaying extended radial processes with their endfeet contacting both the ventricular and pial surfaces (FIG. 1B, arrows).

Figure 2:
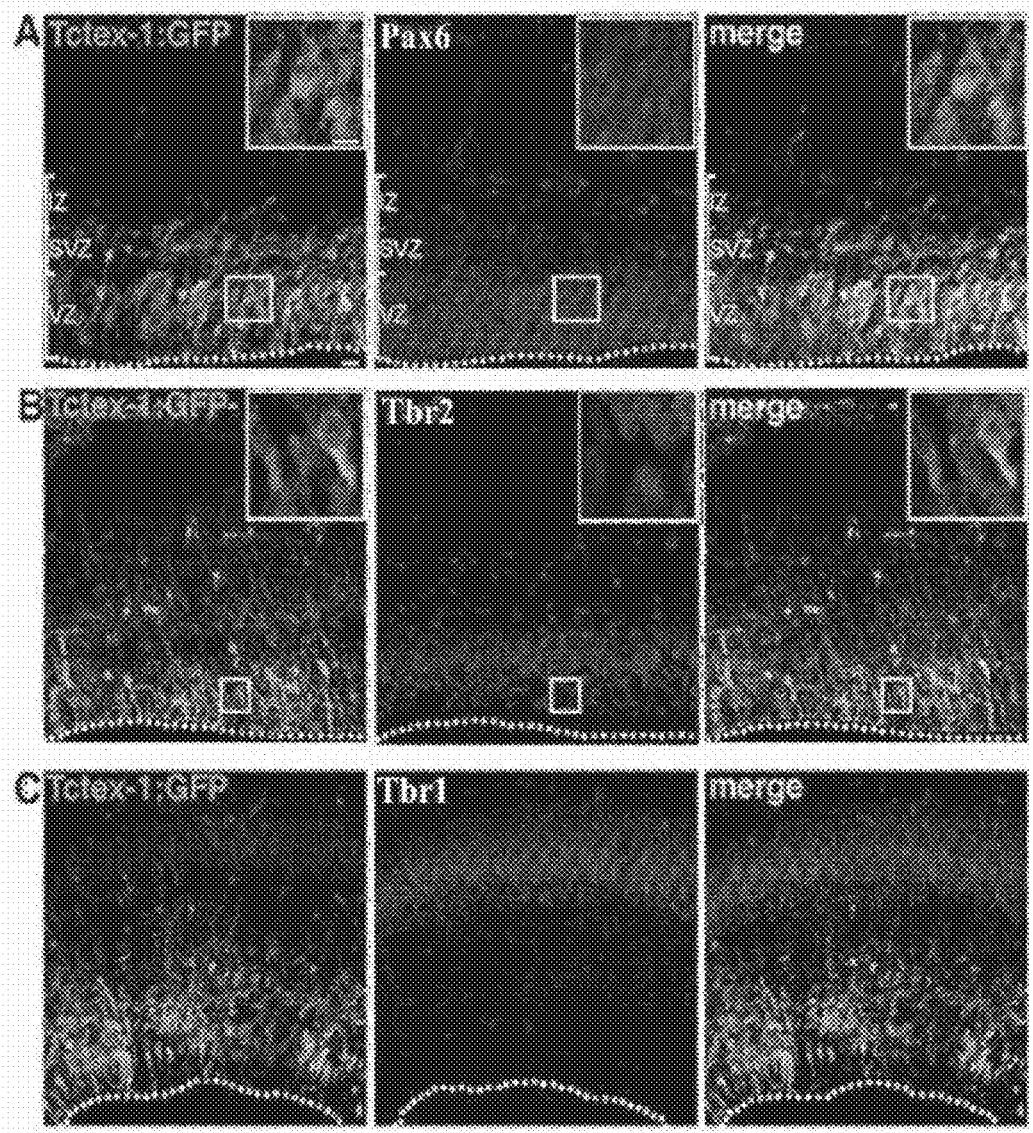
FIG. 2. Colocalization studies demonstrating that P/E–Tctex:GFP targets a mixture of radial glial cells and intermediate progenitors in developing neocortex. Confocal images of PIE-Tctex-1:GFP transfected cortical slices that were co-labeled for Pax6 (A), Tbr2 (B), or Tbr1 (C). Inserts show an enlargement of the boxed areas. Bars=20 µm.; 4 µm. (inserts).

Immunostaining of several transcription factors (e.g., Pax6, Tbr2, Tbr1) that mark cells at different stages during neocortical development was carried out to further characterize the types of cells targeted by the Tctex-1 regulatory sequence (FIG. 2). Pax6 was specially expressed in RG cells whose cell bodies are enriched at the VZ (Englund et al., 2005; Gotz et al., 1998). Tbr2 was expressed in the intermediate progenitors (or transient amplifying progenitors) that are distributed predominantly in the SVZ (Englund et al., 2005; Hodge et al., 2008). Tbr1 has been previously found to be expressed by postmitotic neurons that are distributed throughout the IZ, subplate, and cortical plate (Englund et al., 2005; Hevner et al., 2001). The immunostaining showed that 76%±3% and 33%±1% (n=300 cells in 3 independent experiments) of Tctex-1-GFP+ cells also expressed Pax6 and Tbr2, respectively, and practically no Tctex-1-GFP+ cells were Tbr1 (FIG. 2).

Figure 3:
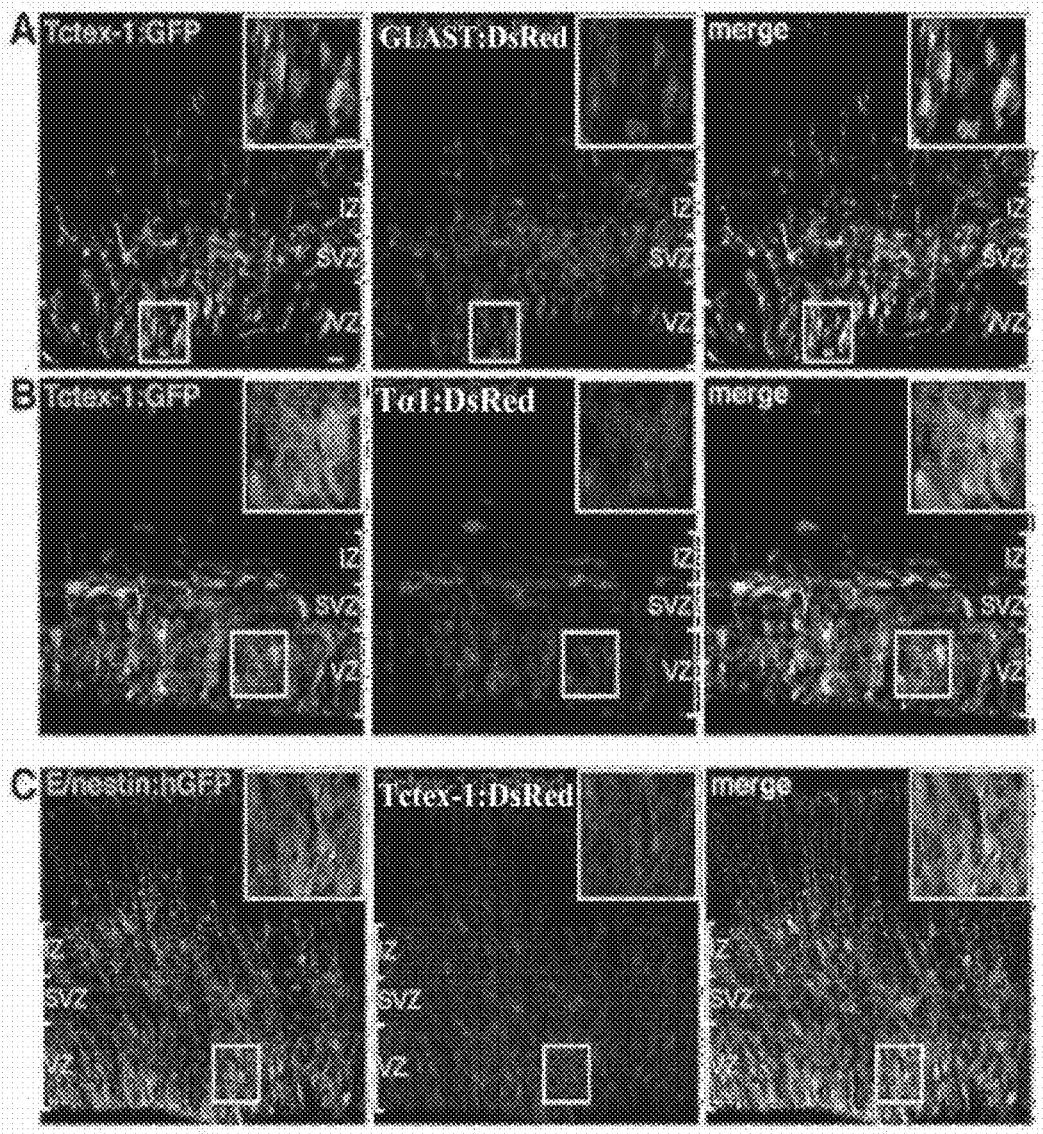
FIG. 3. Promoter activity profiling assays demonstrating that P/E-Tctex:GFP targets a mixture of radial glial cells and intermediate progenitors in developing neocortex. Cortical slices harvested from brains co-transfected with PIE-Tctex-1:GFP and P/GLAST:DsRed (A) or P/Tα-1:DsRed (B) are shown. Cortical slices co-electroporated with PIE-Tctex-1:DsRed and E/nestin:hGFP constructs show that the pools of cells expressing GFP and DsRed are almost completely overlapping (C). Bars=20 µm.; 4 µm. (inserts).

Several cell-type specific reporters have been shown to be able to target distinct populations of neocortical cells (Gal et al., 2006; Wang et al., 2007). For example, Tα-1 promoter preferentially targets intermediate progenitors and post-mitotic young neurons (Wang et al., 2000). The GLAST promoter preferentially targets RG cells (Gal et al., 2006). To independently analyze the cell types that the Tctex-1 regulatory sequence targeted, P/E-Tctex-1:GFP plasmid with pGLAST-DsRed2 or pTα-1-DsRed were co-electroporated into neocorticies and examined the coincidence of cells expressing both GFP and DsRed. Confocal microscopic examination of brain sections harvested 40 hrs post-transfection showed that 80%±4% and 31%±3% of GFP+ cells also expressed GLAST- and Tα-1-promoter-directed DsRed2 (FIG. 3 A, B).

Finally, reporter constructs driven by the enhancer element of nestin (e.g., E/nestin:hGFP) have been reported to be useful for targeting both RG as well as intermediate progenitors in embryonic brains (Gal et al., 2006). The E/nestin:hGFP reporter construct was co-electroporated with the reporter plasmid in which DsRed gene was under the control of P/E-Tctex-1 (i.e. P/E-Tctex-1:DsRed) into developing neocortex and their expression patterns were compared. The transfected cortical slices showed that almost 100% of DsRed+ cells also expressed GFP (FIG. 3 C). The promoter profiling and immunostaining studies suggested that the identified Tctex-1 regulatory sequence directed specific gene expression in both RG and intermediate progenitors in developing neocortex.

Generation and Characterization of P/E-Tctex-1:GFP Transgenic Mice

Figure 4:
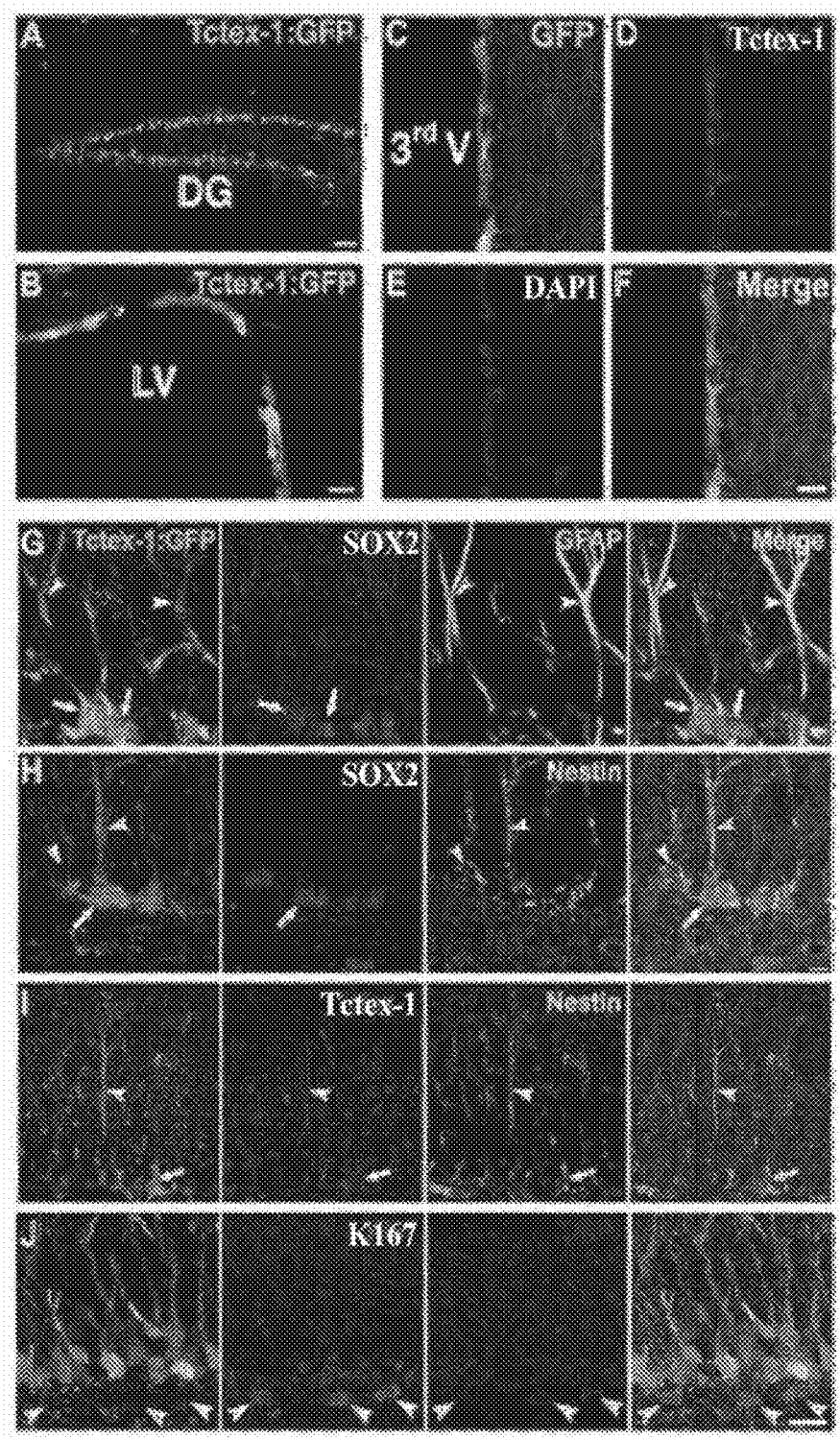
FIG. 4. Expression pattern of PIE-Tctex-1:GFP cells in adult mouse brains (mouse line 4). The distribution patterns of GFP-expressing cells at the DG (A) and lateral ventricle (B) are shown. (C-F) The labeling of endogenous Tctex-1 (red) in GFP-expressing cells at the $3^{rd}$ ventricle was shown. (G, H) Triple labeling of GFP, Sox2 (red in G, H) and GFAP (cyan in G) or nestin (cyan in H) at adult SGZ. Note that the cell bodies of GFP+ cells were often immunoreactive for Sox2 (arrows in G, H). The processes of GFP+ cells were positive for GFAP (arrowheads, G) or nestin (arrowheads, H). (I) Triple labeling of GFP, Tctex-1 (red) and nestin (cyan) showed that endogenous Tctex-1 is localized on both nestin+/GFP+ processes (arrowheads) and GFP+ cell bodies (arrow). (J) Confocal images showed that Ki67-labeled SGZ cells did not expressed Tctex-1:GFP. Scale bars: 50 µm (a); 20 µm (B, C, J), 5 µm (G, H); 10 µm (in I).
Figure 5:
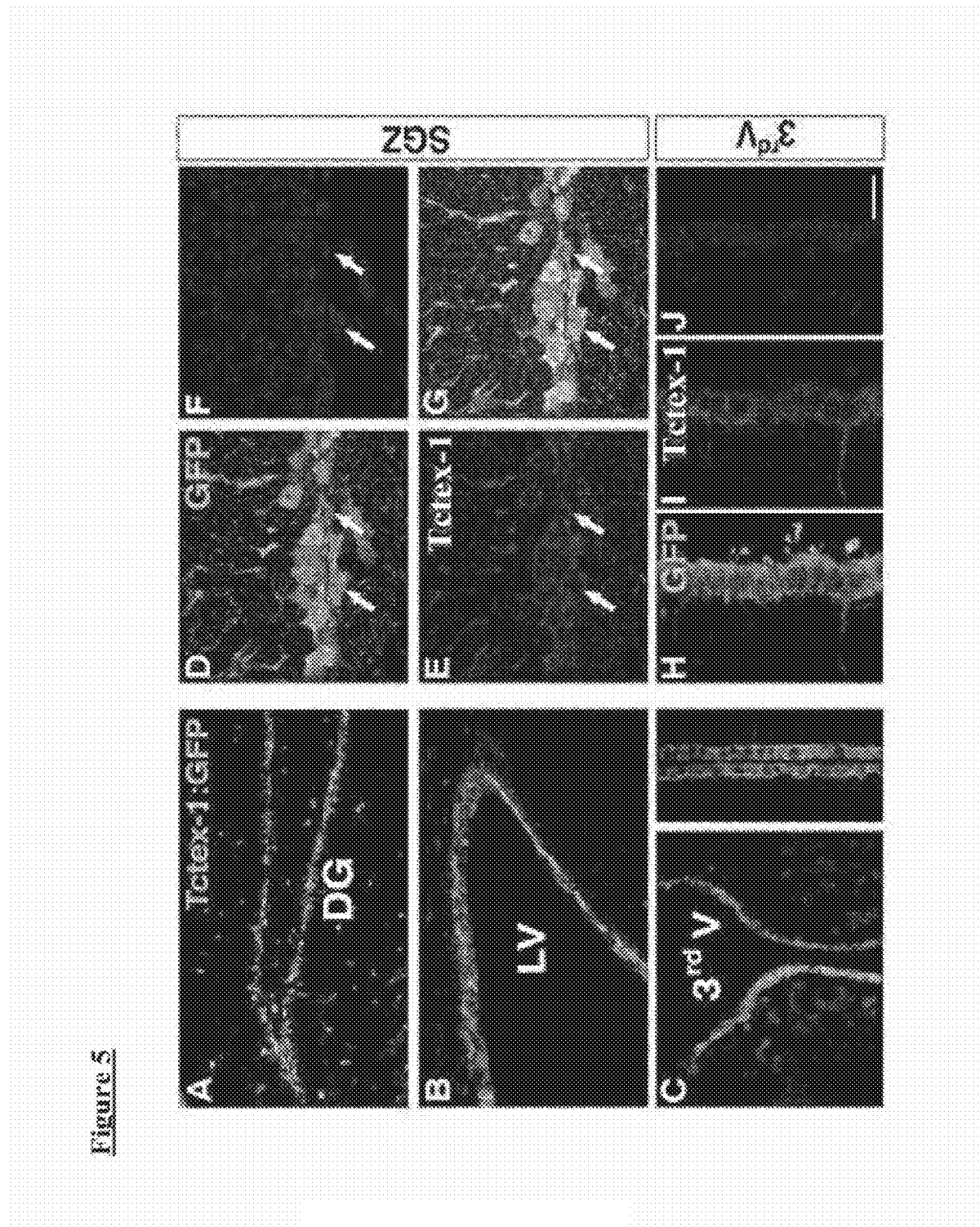
FIG. 5. Transgenically expressing P/E–Tctex-1:GFP cells were enriched in the brain regions that exhibit adult neurogenesis, and these cells also express endogenous Tctex-1 (mouse line 17). The distribution patterns of GFP-expressing cells at the DG (A), lateral ventricle (B), and 3rd ventricle (C) of mice transgenically expressing P/Tctex-1:GFP are shown. Enlarged views showed the co-labeling of Tctex-1 (red) and GFP (green) in the DG (D-G) and 3rd ventricle (H-J) regions. Many Tctex-1+ SGZ cells had irregularly shaped nuclei and horizontally orientated processes (arrows). Bar=20 µm.

To evaluate whether the genomic fragment of Tctex-1 that directed specific expression in the neocortical progenitors also had transcription activity in adult neural stem/progenitors, transgenic mice carrying P/E-Tctex-1: GFP were generated. We obtained a total of 16 independent lines of such mice. Among these, all four independent founder mice tested generated progeny stably expressing the transgene. Examination of the GFP immunoreactivity of 8-week-old mouse brains of all 4 lines (4, 13, 17 18) showed that cells expressing Tctex-1:GFP, like those that expressed endogenous Tctex-1 (Dedesma et al., 2006), were enriched at the SGZ of DG (FIG. 4 A, FIG. 5 A, 5D-G) and the lateral ventricle (FIG. 4 B, FIG. 5 B). In addition, prominent GFP signals were found on almost all cells aligned with the 3rd ventricle (FIG. 4 C-F, FIG. 5 C, H), where specific enrichment of endogenous Tctex-1 was confirmed (FIG. 4 C-F, FIG. 5 H-J). Nevertheless, close examination of the DG region suggested that the GFP expression patterns in these 4 mouse lines fell into two groups and characterization of DG GFP+ cells is described separately below.

P/E-Tctex-1:GFP is Predominantly Expressed in the Sox2+/Nestin+/GFAP+ Stem-Like SGZ Cells In two independent lines (i.e., line 4 and line 13), Tctex-1: GFP expressing cells at DG exhibited long processes that radiated through granular layer and branched out at molecular layer. These cells were morphologically similar to that of neural stem-like cells described for this brain region (Mignone et al., 2004). Indeed, a large subset of GFP expressing cells was positive for Sox2 (arrows in FIG. 4G, H), a transcription factor primarily associated with the DG neural stem-like cells (Komitova and Eriksson, 2004). Furthermore, the radial processes of GFP+/Sox2+ cells were immunolabeled with GFAP (arrowheads in FIG. 4 G) as well as nestin+ (arrowheads in FIG. 4 H). Endogenous Tctex-1 was also detected in both the cell bodies and processes of these GFP+ cells (FIG. 4 I). Finally, the large majority of the SGZ Tctex-1+ cells were negative for Ki67, a marker for cells at cell cycle (arrowheads in FIG. 4J). These results collectively suggested that GFP in these two transgenic lines was predominantly expressed in the Sox2+/GFAP+/nestin+ neural stem-like cells of adult SGZ.

Figure 6:
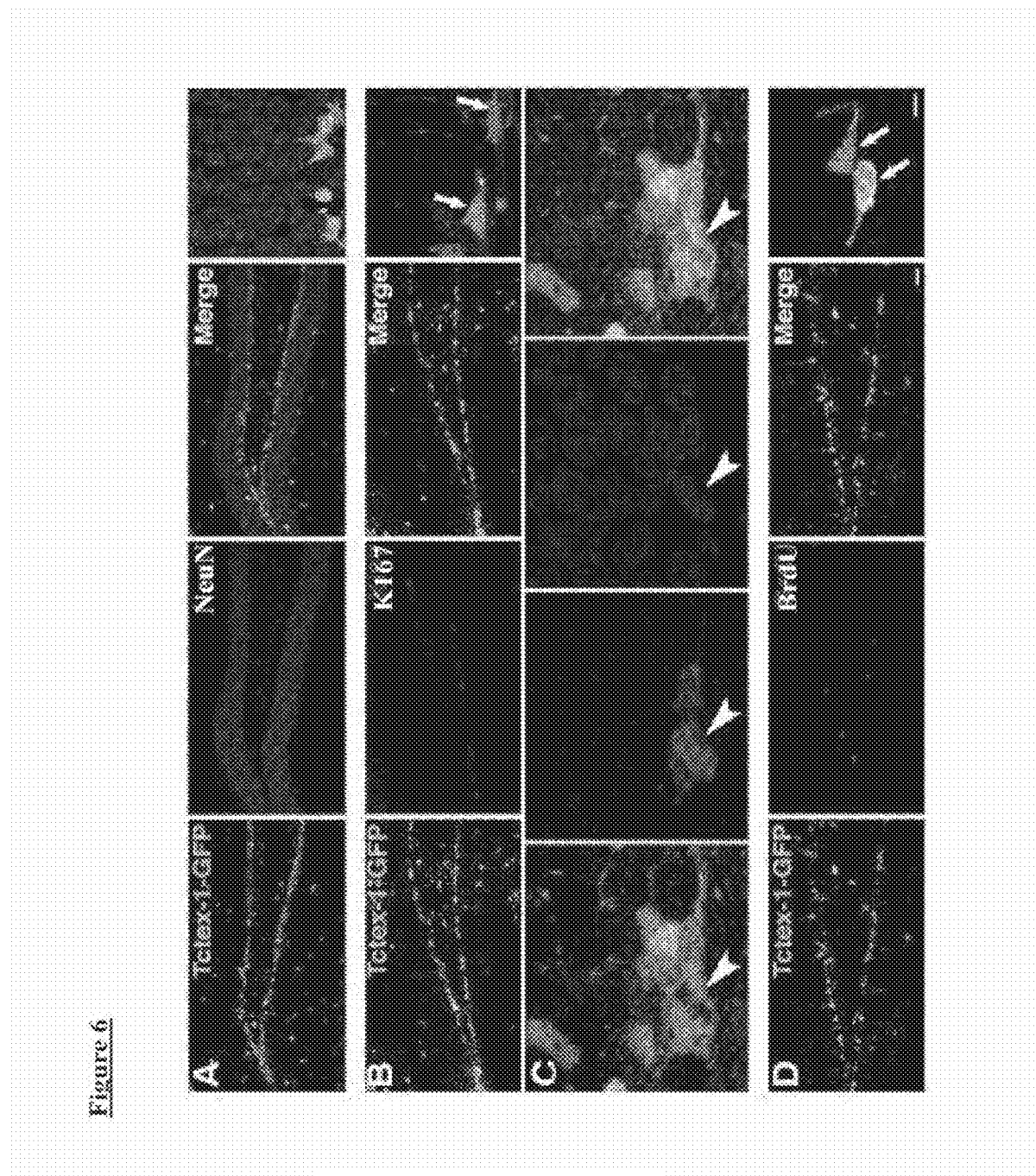
FIG. 6. Transgenically expressed Tctex-1-GFP cells are proliferating mitotic SGZ cells (mouse line 17). Confocal images of adult DG slices obtained from the transgenic mice carrying PIE-Tctex-1:GFP were co-labeled for GFP (green in all panels) along with NeuN (A), Ki67 (B, C), 1-h (BrdU) (D). Inserts show that Tctex-1:GFP and NeuN+ signals were mutually exclusive (A). However, Tctex-1:GFP SGZ cells were often Ki67+ or BrdU+ (Arrows in B and D). A Ki67+/Tctex-1:GFP+ cell under division is also shown (arrowhead in C; blue: DAPI). Scale Bars=20 µm.; 4 µm. (inserts).

P/E-Tctex-1:GFP is Predominantly Expressed in the Transient Amplifying Progenitors of Adult DG Examination of the DG regions of mouse lines 17 and 18 showed that Tctex-1:GFP$^+$ cells and NeuN+ mature granule neurons were mutually exclusive from each other (FIG. 6 A). In contrast to the Tctex-1:GFP cells in mouse lines 4 and 13, a significant fraction of Tctex-1:GFP cells were Ki67-positive (i.e. 48% and 42% of Ki67+ cells were also GFP in lines 17 and 18, respectively; FIG. 6 B, C). The proliferation ability of Tctex-1:GFP+ cells was characterized using a BrdU incorporation assay. In these experiments, the animals received three consecutive injections of BrdU within 6 h and were then allowed to survive for an additional 1 h, 24 h, or 72 h after the last injection. About 26±4% of 1-h BrdU-incorporated cells were also Tctex-1:GFP+; these cells were most likely transient amplifying progenitors. Consistently, these cells tended to have tangentially oriented cell bodies and short horizontal processes (FIG. 6 D, arrows). Longer survival time resulted in an increase in the fraction of Tctex-1:GFP+/BrdU$^+$ cells out of total BrdU$^+$ cells (i.e., 55±6% at 24-h harvest and 70±3.3% at 72-h harvest), indicating that Tctex-1:GFP was also expressed in the later progenitors.

Figure 7:
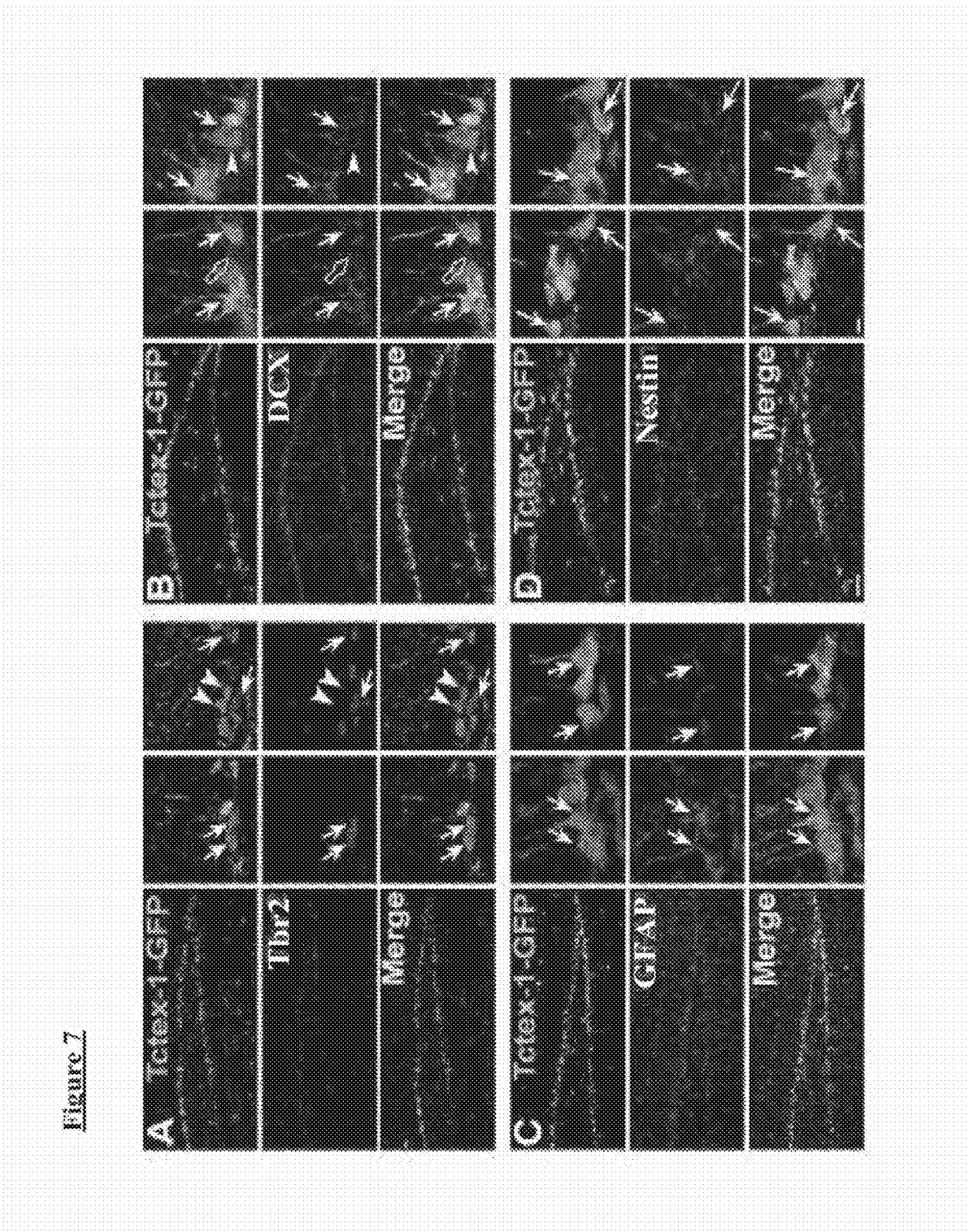
FIG. 7. Adult SGZ Tctex-1-GFP cells represented Type 2 and Type 3 transient amplifying progenitors. Confocal images of adult DG slices of P/E-Tctex-1 GFP mice were co-labeled for Tbr2 (A), DCX (B), GFAP (C) or Nestin (D). Inserts show 2 sets of enlarged views. Arrows in (A) showed that all Tbr2+ cells are Tctex-1:GFP+. Arrows, open arrow and arrowheads in (B) point to Tctex-1:GFP+/DCX, Tctex-1:GFP+/DCX+, Tctex-1:GFP+/DCX-populations, respectively. Arrows in (C) showed that GFAP+ processes were often in close proximity to Tctex-1:GFP+ cells. However, Tctex-1:GFP cells did not express GFAP. Arrows in (D) show that tctex-1:GFP+ cells were occasionally surrounded by nestin-labeled fibers. Bars=50 µm.; 5 µm. (inserts).
Figure 10A:
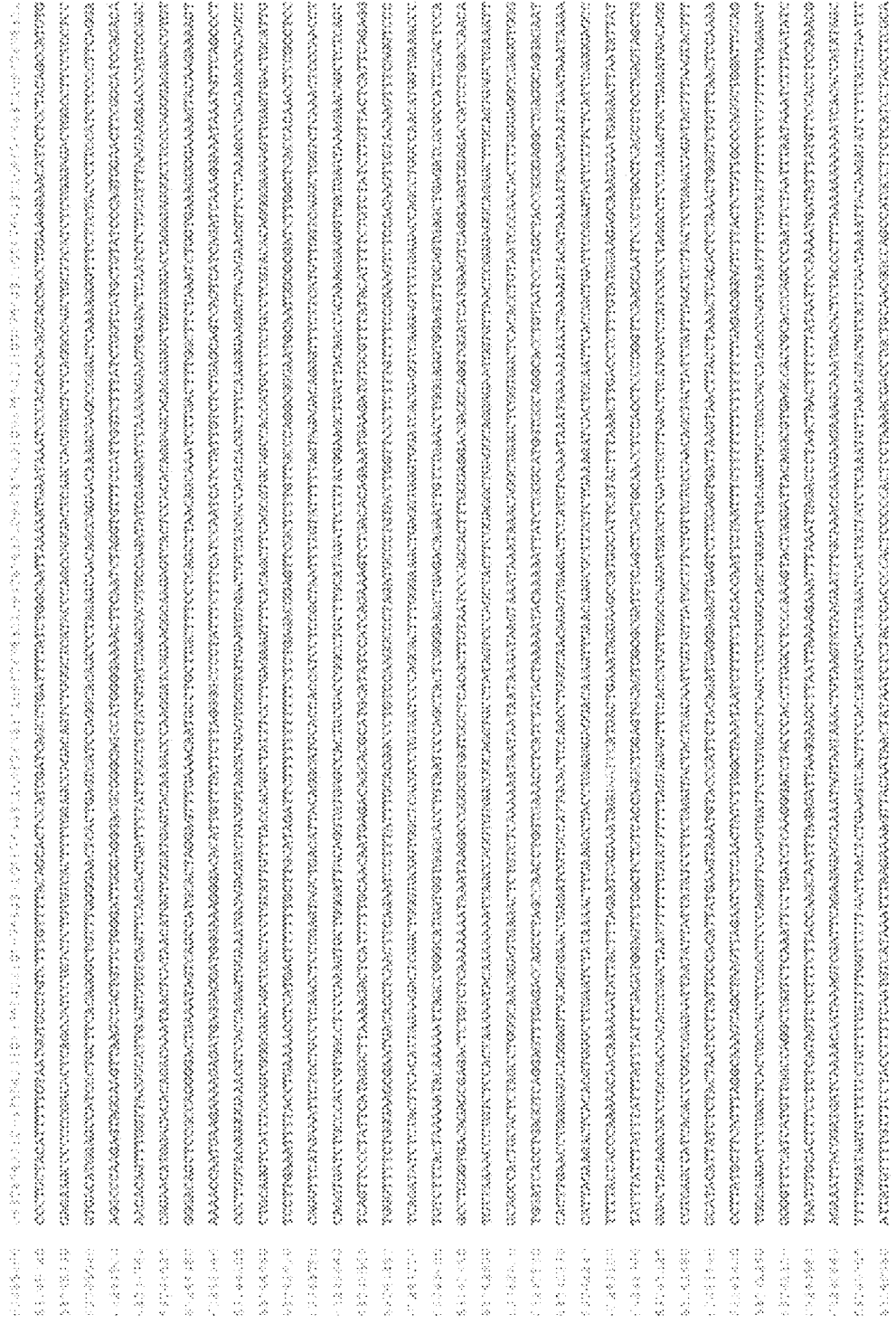
FIG. 10 (presented herein as FIGS. 10A-C). The nucleotide sequence of the human Tctex-1 regulatory sequence operatively linked to a nucleotide sequence partially encoding human Tctex-1 (SEQ ID NO: 9). The amino acid sequence of two fragments of human Tctex-1 are also set forth (SEQ ID NOS 10 and 11).
Figure 10B:
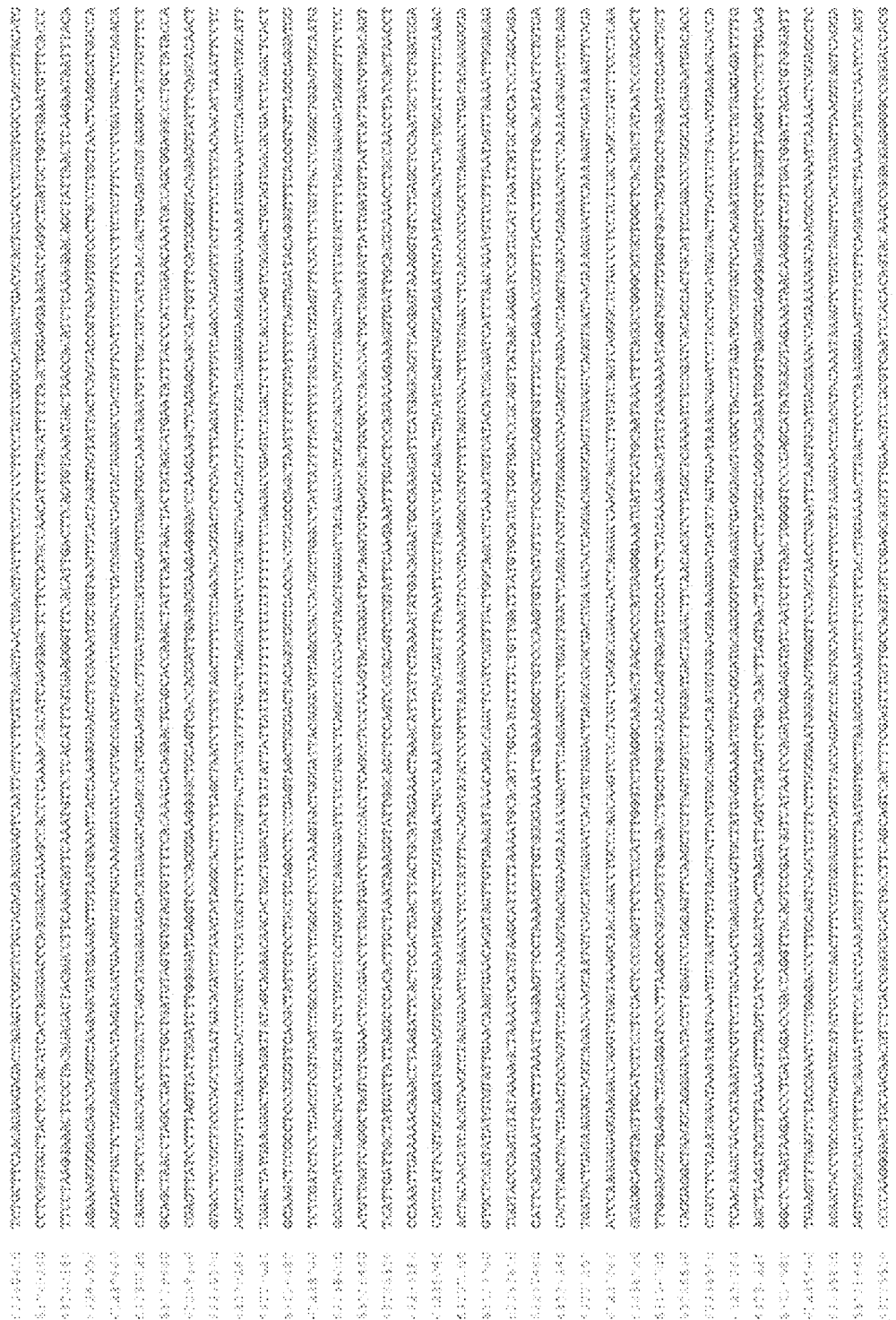

The identities of Tctex-1:GFP SGZ cells in these mouse lines were analyzed by colocalization study using Abs that mark type-2 or type-3 progenitors. Nuclear Tbr2 labeling primarily highlights the type-2 progenitors and a subset of type-3 progenitors (Hodge et al., 2008). In contrast, DCX-derived process labeling was distributed primarily in type-3 progenitors as well as post-mitotic young neurons. Under low-power survey, it appeared at the SGZ, that the DCX cells outnumbered the Tctex-1:GFP$^+$ cells, which outnumbered the Tbr2$^+$ cells. Detailed confocal examination showed that essentially all Tbr2-immunoreactive cells were also Tctex-1:GFP+ (FIG. 7 A, arrows). However, a population of GFP$^+$/Tbr2$^-$ cells also existed (FIG. 7A, arrowheads). The DCX co-localization studies showed that all three populations DCX$^+$/GFP$^+$ cells (FIG. 7B, arrows), DCX+/GFP$^-$ cells (FIG. 7 B, open arrow), and DCX$^-$/GFP+ cells (FIG. 7B, arrowhead) were detected.

Finally, very few, if any, GFP-expressing SGZ cells were positive for Sox2, nestin or GFAP (FIG. 7 C, D). Although the GFAP-labeled processes were often in close proximity with the GFP$^+$ processes, most of them were not coincidental (FIG. 7 C, D). Similarly, none of the radial processes labeled by nestin appeared to display detectable GFP$^+$.

In all four P/E-Tctex-1:GFP mouse lines examined, practically none of the GFP+ cells expressed the mature neuronal marker NeuN in DG, SVZ, or 3rd ventricle (FIG. 5 A). However, examination of the adult SGZ cells expressing GFP reporter of these four mouse lines showed that one group of mice (i.e. lines 4 and 13) had GFP selectively marked type-1 neural-stem like cells whereas the other group of mice (i.e. lines 17 and 18) had type-2/type-3 neural progenitors marked with GFP.

Disclosed are Tctex-1:GFP expressing cells that represent type-2 and type-3 progenitor cells.

Neural Progenitors in Developing and Adult Brains Share a Similar Gene Regulation Pathway In one embodiment, the neocortical and adult SGZ progenitors share common machineries for gene expression regulation, consistent with the recent notion that a parallel cascade of transcription factors (e.g., Pax6, Tbr2) exists in the developing neocorticies and the adult DG (Hodge et al., 2008). In one embodiment, the neural progenitors of different origins and/or of different developmental stages may exhibit overlapping cellular properties.

Although transgenic mice are the conventional method for screening a regulatory element for gene expression, it is nevertheless time-, labor- and cost-consuming. A methodology which could combine the power and certitude of the transgenic approach together with a rapid screening technique would allow researchers to more quickly define regions of DNA involved in the spatial regulation of a given gene. Disclosed is a genomic fragment of the Tctex-1 gene that directs reporter expression in adult brain. Also disclosed is "tissue transfection" for the convenient and rapid method for the in vivo characterization of a promoter/enhancer among several types of retinal cells.

The 3rd ventricle has recently been proposed to be another site exhibiting neurogenic activity outside the SGZ and sub-ventricular zone (SVZ) of the lateral ventricle (Xu et al., 2005). Although the numbers are small, mitotic progenitor cells appear to reside in the ependymal layer of the adult rat 3rd ventricle, and they could differentiate into neurons that could migrate and integrate into the hypothalamus. The neurogenic activity of this area could readily be upregulated upon various stimuli (Xu et al., 2005). Interestingly, GFP driven by the Sox2 promoter has recently been shown to be enriched in 3rd ventricle ependymal cells (Brazel et al., 2005). Our coincidental observation that the 3rd ventricle ependymal cells had a high level of Tctex-1 promoter/enhancer activity as well as endogenous Tctex-1 further implies that the 3rd ventricle cells may possess intrinsic characteristics similar to those of SGZ and SVZ progenitors; however, a yet-to-be-identified suppressor may inhibit their mitogenic activity under normal physiological conditions.

Identification of a Novel Regulatory Element Specifying Adult SGZ Neural Progenitors In all four P/E-Tctex-1:GFP mouse lines examined, practically none of the GFP cells expressed the mature neuronal marker NeuN in DG, SVZ, or 3rd ventricle (FIG. 5A). However, examination of the adult SGZ cells expressing GFP reporter of these four mouse lines showed that one group of mice (i.e. lines 4 and 13) had GFP selectively marked type-1 neural-stem like cells whereas the other group of mice (i.e. lines 17 and 18) had type-2/type-3 neural progenitors marked with GFP.

In lines 17 and 18, the BrdU and colocalization studies suggested that the GFP reporter level was transiently high in the cycling progenitors but sharply reduced upon neuronal differentiation. Although the distribution patterns of Tctex-1: GFP and endogenous Tctex-1 were qualitatively identical at the adult SGZ, the BrdU birth-dating experiments suggested that the expression of GFP-Tctex-1 has a slight delay compared to that of the endogenous Tctex-1. Our previous finding showed that ~90% of 2-h BrdU-labeled type-2 early progenitors displayed endogenous Tctex-1(Dedesma et al., 2006). Less than 30% of 1-h BrdU-labeled cells exhibited Tctex-1: GFP. Instead, a higher fraction of 72-h BrdU labeled, type-3 progenitors expressed Tctex-1:GFP. A delay in reporter expression was observed in transgenic mouse lines targeting the adult-born SGZ cells (FIG. 7). For example, GFP controlled by the enhancer/promoter of the nestin gene was expressed not only in the type-1 cells (where endogenous nestin is present) but also in the type-2 cells (where endogenous nestin is absent; Filippov et al., 2003; Steiner et al., 2006). DCX promoter-directed DsRed was expressed not only in the type 3 progenitors, but also in the NeuN+ mature granular neurons (Couillard-Despres et al., 2006).

A number of genomic sequences that directed specific expression in adult born neural stem/progenitors cells have been isolated (Couillard-Despres et al., 2006; Filippov et al., 2003; Fukuda et al., 2003; Steiner et al., 2006). Nevertheless, isolation of a relatively small genomic fragment with great specificity of targeting the SGZ progenitors adds an additional versatile tool for experimental manipulation of these cells. For example, this regulatory region could be employed for selective loss- or gain-of-function studies of genes of interest. In addition, tools that identify these cells may allow one to directly examine the development of these cells in vivo (i.e., fate mapping). These studies collectively may reveal the bona fide identity of these cells, their biology, and effective strategies to manipulate them.

Perspective Function of Tctex-1 in Adult Stem/Neural Progenitors

The selective enrichment of Tctex-1 in the adult SGZ neural stem/progenitors cells was first described based on the immunohistology and in situ studies (Chuang et al., 2001; Dedesma et al., 2006). Similar expression pattern of the transgenic GFP reporter directed by the regulatory region of Tctex-1 independently confirmed the specific enrichment of Tctex-1 in these cells. Several cellular functions of Tctex-1, both cytoplasmic dynein-dependent and independent, have been reported (Chuang et al., 2005; Machado et al., 2003; Mueller et al., 2002; Nadano et al., 2002; Nagano et al., 1998; Schwarzer et al., 2002; Tai et al., 1999; Tai et al., 2001). Of great interest, Tctex-1 is also synonymous with activator of G protein signaling 2 (AGS2), which binds to the Gβ subunit and is involved in the non-canonical receptor-independent G protein signaling pathway (Sachdev et al., 2007; Takesono et al., 1999). It has been shown that non-canonical receptor-independent G protein signaling pathway plays a key role in the symmetry of cell division of fly neuroblasts and *C. elegans* embryoes (Gotta et al., 2003; Schaefer et al., 2001), but AGS2 has not been shown to be a marker of mammalian neural stem or progenitors. A mammalian activator of G protein signaling 3 (AGS3) (not synonymous with Tctex-1) has recently been suggested to participate in the cell fate determination of neural progenitors during neocortical development (Sanada and Tsai, 2005).

Intestinal Progenitors.

A great deal of interest has been generated of late with regard to the identification of intestinal progenitor cells (Barker et al, 2007) and the role of these cells in cancer (Barker et al., 2009). Tctex-1 has been found in microarray studies to be enriched in intestinal progenitor cells (Mills et al 2002) and thus the regulatory sequence described herein is useful for targeting intestinal progenitors as well.

Txtex-1 Regulatory Sequence

In one embodiment, the regulatory sequence has the nucleotide sequence set forth in SEQ ID NO: 1, i.e., the human tctex-1 regulatory sequence.

In one embodiment, the regulatory sequence has the nucleotide sequence set forth in SEQ. ID NO: 2, i.e., the mouse tctex-1 regulatory sequence.

In one embodiment, the regulatory sequence has the nucleotide sequence set forth in SEQ. ID NO: 3, i.e., the mouse tctex-1 regulatory sequence operatively linked to a nucleotide sequence encoding GFP.

In another embodiment, the regulatory sequence has at least about 95% sequence homology to the nucleotide sequence set forth in SEQ ID NO: 1 or the nucleotide sequence set forth in SEQ ID NO: 2.

In another embodiment, the regulatory sequence has at least about 90% sequence homology to the nucleotide sequence set forth in SEQ ID NO: 1 or the nucleotide sequence set forth in SEQ ID NO: 2.

In another embodiment, the regulatory sequence has at least about 85% sequence homology to the nucleotide sequence set forth in SEQ ID NO: 1 or the nucleotide sequence set forth in SEQ ID NO: 2. In another embodiment, the a regulatory sequence has at least about 80% sequence homology to the nucleotide sequence set forth in SEQ ID NO: 1 or SEQ ID NO: 2.

Disclosed is a method for treating a subject having a neural disease, disorder, or condition, comprising the step of administering a pharmaceutical composition to a subject, thereby treating the subject having the neural disease, disorder, or condition.

Disclosed is a method for selectively expressing a nucleic acid of interest in a progenitor cell in a cell population, said method comprising: placing the nucleic acid of interest under control of a Tctex regulatory sequence which functions selectively in said progenitor cell, and introducing the nucleic acid of interest placed under control said Tctex regulatory sequence into said cell population, thereby selectively expressing the nucleic acid of interest in the progenitor cell in the cell population.

Disclosed is a method for marking progenitor cells in a cell population, said method comprising: placing a marker gene under control of a Tctex regulatory sequence which functions selectively in said progenitor cells; introducing the marker gene placed under control of the Tctex regulatory sequence into said cell population, and allowing expression of said marker gene in said progenitor cells, thereby marking the progenitor cells in a cell population.

Disclosed is a process for separating marked cells from a cell population, said process comprising: placing a marker gene under control of a Tctex regulatory sequence which functions selectively in said progenitor cells; introducing the marker gene placed under control of the Tctex regulatory sequence into said cell population, and allowing expression of said marker gene in said progenitor cells, thereby marking cells which express the marker gene; and separating the marked cells from the cell population.

Disclosed is a method for assessing activity of progenitor cells within a cell population, said method comprising: placing a marker gene under control of a Tctex regulatory sequence which functions selectively in said progenitor cells; introducing the marker gene placed under control of the Tctex regulatory sequence into said cell population, and allowing expression of said marker gene in said progenitor cells, thereby assessing activity of progenitor cells within a cell population.

Utilities

R&D

The isolated Tctex-1 regulatory sequence with great specificity of targeting progenitors provides a versatile tool for experimental manipulation of these cells.

Cells, cell lines, and mice incorporating the Tctex-1 regulatory sequence driving a marker provide a unique tool to examine behavior or progenitors, including the study of neurogenesis in adults and in development and the role of intestinal progenitors in intestinal biology and diseases, such as cancer. First, they could be employed to examine the effect of various experimental agents and conditions on progenitor behavior by simply scoring the GFP$^+$ cycling cells. Like [3-H]-thymidine, BrdU incorporates into the DNA of cells undergoing DNA synthesis. The incorporated BrdU can be subsequently detected by ant'-BrdU antibody. Although useful, this method has several weaknesses: the cytotoxicity; the dilution of BrdU with each cell division; and the long tedious procedures involved in immunolabeling.

Cells, cell lines, and mice incorporating the Tctex-1 regulatory sequence driving a marker are a tool can be used to investigate how injury, disease, or aging affect progenitors. Specifically with regard to the central nervous system, they can be used to study the brain microenvironment and the proliferation and neurogenic ability of cells of the adult germinal zone. With regard the intestine, they can be used to study the intestinal crypt microenvironment and the proliferation of cells therein. They can be used for the fate mapping experiments: transgenic mice with Tctex-1 regulatory sequence directed expression of inducible form of Cre recombinase (e.g., Cre$^{ERT2}$) can be crossed with a dual reporter mouse (e.g., Z/EG), so that the ontogeny, the life span, and the development of the adult-generated cells can be traced in vivo. Cells and cell lines can be used for in vitro characterization and/or comparison to the Type 1 cells isolated from other mice. Likewise, they can be used for selective loss- or gain-of-function studies of genes of interest.

In addition, these research tools are valuable in discovering and evaluating drugs that effect progenitor cells. In the central nervous system, indications for such drugs could related to reversal of the age-, condition-, or disease-related deficit in adult neurogenesis. Conversely, to the extent that progenitor cells are involved in cancers of the central nervous system, the indications could be related to treating said cancers. In the intestine, indications for such drugs could related to reversal of the age-, condition-, or disease-related deficit in renewal of the epithelium. Conversely, to the extent that progenitor cells are involved in intestinal cancers, including colon cancer, the indications could be related to treating said cancers.

Therapeutics that May be Placed Under Control of Tctex-1 Regulatory Sequence

The Tctex-1 regulatory sequence may be employed to selectively introduce a molecule to manipulate the activity of progenitor cells by placing a nucleic acid encoding the molecule under control of the Tctex-1 regulatory sequence. Such a sequence can encode protein that has therapeutic benefit. A protein that affects the progenitor cells' fate, such as a protein that controls or influences cell functions such as cell cycle, proliferation, neurogenesis, cell migration, cell differentiation, cell growth and guidance, cell adhesion, synaptic formation and other functions, is termed a "protein of interest." Sample proteins of interest are listed in Table A. The molecule placed under control of the Tctex-1 regulatory sequence can also encode an siRNA, microRNA, antisense molecule, or aptamer. Such a nucleic acid molecule is termed herein an effector nucleic acid.

Disclosed effector nucleic acids of interest are siRNA, microRNA, antisense molecules, or aptamers, placed under the control of the Tctex-1 regulatory sequence, the products of which inhibit the transcription or translation of a protein of interest or modulate the function of a protein of interest. The products of effector nucleic acids can be used to downregulate or upregulate the level of neurogenesis or intestinal epithelium renewal.

Effector nucleic acids of interest can be a sequence, placed under the control of the Tctex-1 regulatory sequence, which encodes an effector protein, which in turn modulates the function of a protein of interest. The effector protein can be used to downregulate or upregulate the level of neurogenesis or intestinal epithelium renewal Sample Proteins of Interest (Table A):

Neurogenesis stage: Glial fibrillary acidic protein (GFAP); Nestin; T-box brain gene 2 protein (Tbr-2 protein); Doublecortin (CDX); Polysialylated neural cell adhesion molecule (PSA-NCAM); Cyan fluorescent protein (CFP); Ho/rac guanine nucleotide exchange factor (GEF) 2 (Lfc); Vimentin; Sex determining region Y-box 2 (SOX-2); Brain Fatty Acid Binding Protein (BFABP); Prospero-related homeobox 1 (Prox-1); beta III tubulin; Neuronal Nuclei (neuN); Calbindin; Cilliary neurotropic factor (CNTF).

Cell Proliferation: PEgf, Fgf2, Il3, Nrp1, Ptn, Vegfa. Alk, Bai1, Cxcl1, Ndn, Notch2, Odz1. Ache, Cdk5r1, Cdk5rap1, Cdk5rap3, Erbb2, Mdk, Ndph, S100a6, S100b Cell Cycle Genes: Apbb1, Inhba, Ml11, Notch2, Apbb1, Inhba, Ep300, Fgf2, Hdac4, Hdac7, Mdk, Ndn, Pard6b, S100a6, S100b.

Regulation of Cell Motility and Cell Migration: Flna, Ntn1, Pafah1b1, Pard6b, Slit2, Stat3, Vegfa.

Regulation of Cell Differentiation: Cdk5r1, Cdk5rap1, Cdk5rap2, Cdk5rap3, Ywhah, Dl11, Notch2, Shh, Ascl1, Hdac4, Hdac7, Inhba, Mdk, Ncoa6, Neurod1, Nog, Nrcam, Nrg1, Pax5, Pax6.

Growth Factors and Cytokines: Artn, Bdnf, Bmp15, Bmp2, Bmp4, Bmp8b, Cxcl1, Gpi1, Egf, Fgf13, Fgf2, Gdnf, 113, Inhba, Mdk, Ndph, Nrg1, Ptn, S100a6, Vegfa. Bmp15, Bmp2, Bmp4, Bmp8b, Cxcl1, Gpi1, Il3, Inhba, Mdk, Ptn.

Genes Involved in Synaptic Functions: Apoe, Grin1, S100b, Ywhah, Chrm2, Dlg4, Drd2, Drd5, Grin1, Nptx1, Ache, Nrcam, Pou4f1.

Apoptosis: Gdnf, Notch2, Sema4d, Adora1, Apoe, Inhba, Notch2, S100b, Adora2a, Ep300, Ntnl1, Pax3, Rtn4, Vegfa Ywhah.

Cell Adhesion: Robo1, Ache, Bai1, Dl11, Efnb1, Fez1, Nrcam, Nrp1, Nrp2, Pard3, Rac1, Sema4d, Slit2, Tnr.

Cell Signaling Genes Involved in Neurogenesis: Dl11, Notch2, Dvl3, Adora1, Adora2a, Bai1, Chrm2, Cxcl1, Drd2, Drd5, Gnao1, Ncoa6, Notch2.

Or other genes as are known in the art, including mutated Tctex-1 genes as described in WO/2007/005733, published Jan. 11, 2007, which is incorporated herein by reference.

Isolated Cell Populations

Disclosed are methods for the isolation of Tctex-1 marked cells, using any of the marking approaches described herein or known in the art. The Tctex-1 gene is well conserved among mammalian species (2/113 bases change between mice and human). Also disclosed are methods for harvesting of tctex-1-GFP marked neural progenitor cells, including such cells for neural transplantation. For example, in the case of Parkinson's disease there is a progressive neuronal loss affecting preferentially the dopaminergic neurons of the nigrostriatal projection. Transplantation of fetal dopaminergic precursor cells can ameliorate clinical symptoms in affected patients. Cell populations isolated using the Tctex-1 regulatory sequence may be used to ameliorate clinical symptoms of diseases, conditions, and disorders described herein.

Neurogenesis

While not wishing to be bound by any particular theory, and the following is set forth as only one point of view on neurogenesis; however, other valid theories may exist and will exist.

Neural Development

During gastrulation cells migrate to the interior of embryo, forming three germ layers—the endoderm (the deepest layer), mesoderm and ectoderm (the surface layer)—from which all tissues and organs will arise. In a simplified way, it can be said that the ectoderm gives rise to skin and nervous system, the endoderm to the guts and the mesoderm to the rest of the organs. In all vertebrates, following gastrulation there is neurulation, the formation of the neural tube from the ectoderm of the embryo. After gastrulation the notochord—a flexible, rod-shaped body that runs along the back of the embryo—has been formed from the mesoderm. The notochord sends signals to the overlying ectoderm, inducing it to become neuroectoderm. This results in a strip of neuronal stem cells that runs along the back of the fetus. This strip is called the neural plate, and is the origin of the entire nervous system.

The neural plate folds outwards during the third week of gestation to form the neural groove. Beginning in the future neck region, the neural folds of this groove close to create the neural tube. The anterior part of the neural tube is called the basal plate; the posterior part is called the alar plate. The hollow interior is called the neural canal. By the end of the fourth week of gestation, the open ends of the neural tube (the neuropores) close off. Late in the fourth week, the superior part of the neural tube flexes at the level of the future midbrain—the mesencephalon. Above the mesencephalon is the prosencephalon (future forebrain) and beneath it is the rhombencephalon (future hindbrain).

The embryonic neural tube has three layers: the ventricular zone, later called the ependyma, around the lumen (central canal) of the tube; the intermediate zone, which is formed by the dividing cells of the ventricular zone (including the earliest radial glial cell type) and stretches between the ventricular surface and the outer (pial) layer; and the external marginal zone, which is formed later by processes of the nerve cells in the intermediate zone.

The intermediate zone, or mantle layer, increases in cellularity and becomes gray matter via neurogenesis and differentiation of progenitor cells. The ventricular zone and subventricular zone also mature via neurogenesis and differentiation of progenitor cells. The nerve cell processes in the marginal zone, as well as other cell processes, become white matter when myelinated.

Neuronal migration is the method by which neurons travel from their origin or birth place to their final position in the brain. There are several ways they can do this, e.g., by radial migration or tangential migration.

Neuronal precursor cells proliferate in the ventricular zone of the developing neocortex. The first postmitotic cells to migrate form the preplate which are destined to become Cajal-Retzius cells and subplate neurons. These cells do so by somal translocation. Radial glia, whose fibers serve as a scaffolding for migrating cells, can themselves divide or translocate to the cortical plate and differentiate either into astrocytes or neurons. Somal translocation can occur at any time during development. Subsequent waves of neurons split the preplate by migrating along radial glial fibres to form the cortical plate. Each wave of migrating cells travel past their predecessors forming layers in an inside-out manner, meaning that the youngest neurons are the closest to the surface.

Adult Neurogenesis

New neurons are continually born from birth throughout adulthood in predominantly two regions of the brain: 1) The subventricular zone (SVZ) lining the lateral ventricles, where the new cells migrate to the olfactory bulb via the rostral migratory stream.

The subgranular zone (SGZ), part of the dentate gyrus of hippocampus.

Many of the newborn cells in the SGZ die shortly after their birth, but a number of them become functionally integrated into the surrounding hippocampal brain tissue.

There is evidence that adult neurogenesis may also occur in other brain regions such as neocortex, cerebellum and hypothalamus.

Stages of Adult SGZ Neurogenesis

At least three partially overlapping SGZ cell populations have been identified based on their distinct morphologies and expression of specific molecular markers (Ehninger and Kempermann, 2008); (Duan et al., 2008; Zhao et al., 2008). They are described schematically in FIG. 7.

Type-1 progenitors (or neural stem-like cells, Type B cells (Seri et al., 2001)), which rarely divide, can be identified by their expression of glial fibrillary acidic protein (GFAP) and nestin (Fukuda et al., 2003) and by their radial processes with highly elaborated arbors branching into the molecular layers (Mignone et al., 2004). A nuclear transcription protein Sox2 has also been recognized as a marker for mainly Type-1 cells (Steiner et al., 2006)

There are at least two types of GFAP$^-$/Nestin$^-$ transient amplifying progenitors: Type 2 SGZ progenitors have short horizontal processes; they express transcription factor Tbr2 (T-box brain gene 2) (Hodge et al., 2008) and low-level neuronal-lineage markers such as doublecortin (DCX) and polysialylated neural cell adhesion molecule (PSA-NCAM). Type 3 progenitors represent cells committed to the neural fate, and during their transit to become postmitotic immature neurons; these cells have vertical processes and selectively express neuronal DCX, PSA-NCAM, and TuII. Cycling progenitors (i.e., Type 2 and 3) in this brain region appear to be excellent targets for manipulation because of their strong ability to respond to various regulatory influences in vivo (Kempermann et al., 1998; Kronenberg et al., 2003).

Stages of Adult SVZ Neurogenesis

In contrast to adult neurogenesis in the dentate gyrus, cells that were born in the SVZ migrate a long distance into their target area, the olfactory bulb. This long migration gives olfactory neurogenesis a different timescale from DG neurogenesis.: Migration: (2-6 Days) Newborn cells migrate in chains along the rostral migratory stream (RMS), a structure maintained by specialized astrocytes. After the newborn neurons reach the middle of the OB they detach from the chains and migrate radially. Neuronal Differentiation: (15-30 Days) After immature neurons reach the OB, they begin to differentiate into two different types of local interneurons. Over 95% differentiate into GABA-ergic granule neurons whereas the remainder become periglomerular neurons expressing either GABA and/or dopamine as neurotransmitter. Newborn granule cells can be distinguished into cells with dendrites that do not extend beyond the mitral cell layer and other cells that possess non-spiny dendrites reaching into the external plexiform layer. Integration into network: (15-30 Days) Newborn granule cells and periglomerluar neurons become integrated into the OB circuitry and respond to olfactory stimuli.

Juvenile Neurogenesis

The juvenile period of development is an important stage for both neuromaturation, particularly in cortical and limbic brain regions, and behavioral maturation, especially in complex learning such as social interaction skills Juvenile development is also characterized by marked changes in hormones and growth factors. The significant neurochemical and neuroanatomical remodeling during this highly plastic development shapes neuronal networks and behavioral characteristics that persist into adulthood. Various studies using juvenile rodent models have shown that overproduction of axons and synapses occurs during early puberty and is followed by a rapid pruning later in adolescence, which likely contributes to maturation of the brain and the transition to adult. Neurogenesis in both forebrain and dentate gyrus and dorsal hippocampus decreases dramatically following the juvenile period (He and Crews 2007). The high level of neurogenesis in juvenile brain could be reflective of the high level of neuroplasticity during maturation.

EXAMPLES

Example 1

Plasmids and Generation of Transgenic Mice

Chicken actin-CMV (CAG) promoter-directed HcRed was obtained from Dr. Connie Cepko (Harvard). E/nestin:hGFP (Roy et al., 2000a; Roy et al., 2000b; Wang et al., 2000) was obtained from Dr. Neeta Roy (Weill Medical College). pGLAST-DsRed2 and pTα-1-DsRed2 (Ever and Gaiano, 2005) were obtained from Dr. Nicholas Gaiano (Johns Hopkins University School of Medicine). To generate the reporter constructs P/E-Tctex-1:GFP and P/E-Tctex-1:DsRed, an EcoR1 fragment (spanning −5,873 NT to 2861NT of Tctex-1 genomic sequence) was taken from a mouse Tctex-1 bacterial artificial chromosome contig (clone RP23-122p23, CHORE). The sequences between NT 155 and NT165 was replaced by GFP or DsRed coding sequence (FIG. 1A). Finally, ~9.5 kb fragments containing the entire Tctex-1 regulatory domain and reporter gene of the above constructs were transferred and inserted into the backbone of pCAGIG vector (obtained from Connie Cepko (Matsuda and Cepko, 2004)) to produce the transgenes P/E-Tctex-1:GFP (FIG. 1A) and P/E-Tctex-1:DsRed.

For transgenic mouse production, the ~10 kb SfoI/StuI fragment from P/E-Tctex-1:GFP construct was gel purified and used for pronuclear injection (Hogan et al., 1986). DNA was injected into fertilized F2 eggs obtained from matings of C57BL/6JxCBA/J F1 mice. Sixteen founders out of a total of 47 live-born mice were identified to be positive for transgene by genomic Southern blot assay and polymerase chain reaction (PCR) using primers recognizing GFP (5'-GAGGAGCT-GTTCACCGGGGTG-3' (SEQ ID NO: 4) and 5'-GTGGT-TGTCGGGCAGCAGCAC-3' (SEQ ID NO: 5)). Adult animals of two independent lines (13 and 17) were used for experiments. Lines were propagated through breeding with CD1 mice. All animal procedures were approved by the Institutional Animal Care and Use Committee of Weill Cornell Medical College.

Example 2

Antibodies

The primary antibodies (Abs) we used were NeuN (Immunogen: purified cell nuclei from mouse brain, purified mouse IgG1, 1:400, cat# MAB377, Chemicon, Temecula, Calif.), GFAP (Immunogen: purified glial filament, mouse clone G-A-5, 1:400, cat# G3893, Sigma, (Debus et al., 1983)), BρdU (rat IgG2a, clone BU1/75; cat# MAS250C, 1:200, Harlan Sera-Lab Ltd., Loughborough, United Kingdom; Immunogen: BrdU-bovine serum albumin conjugate, mouse IgG1, clone BMC9318, cat #1170376, 1:200, Roche Applied Science, Indianapolis, Ind.), Doublecortin (DCX) (Immunogen: human DCX C-terminus, goat IgG, cat# sc-8066, 1:500, Santa Cruz Biotechnologies, Santa Cruz, Calif.), Sox2 (rabbit Ab, 1:100, Stem Cell Tech), and nestin (Immunogen: paraformaldehyde fixed spinal cord from day 15 rat embryos, purified mouse IgG1, clone Rat 401 (Hockfield and McKay, 1985), 1:1,000, cat#: 556309, BD Pharmingen, San Jose, Calif.), DsRed rabbit Ab (Immunogen: *Discosoma* sp. red fluorescent protein, rabbit polyclonal antibody, cat#632496, Clontech, Mountain View, Calif.), GFP rabbit Ab (Immunogen: green fluorescent protein, rabbit serum, cat# A6455, 1:1000, Molecular Probes, Eugene, Oreg.), GFP chicken Ab (Immunogen: green fluorescent protein, chicken IgY, 1:1,000, cat# ab13970, Abcam, Cambridge, Mass.), Tbr1, and Tbr2 rabbit antibodies (1:1000, rabbit antibody, gifts from Dr Robert Hevner) (Englund et al., 2005), Ki67 (Immunogen: Ki67, rabbit polyclonal antibody, 1:1,000, cat# NCL-Ki67p, Novacostral, Newcastle, UK), and IIax6 mouse MAb (Immunogen: Pax6, purified mouse IgG1, 1:200, Developmental Studies Hybridoma Bank, the University of Iowa, Iowa) were used in this study. Alexa dye-conjugated (Invitrogen), biotinylated-conjugated secondary antibody (Vector), and Cy5-conjugated (Jackson) secondary antibodies were used. Alexa dye-conjugated (Invitrogen), biotinylated-conjugated secondary Ab (Vector), and Cy5-conjugated (Jackson ImmunoResearch, West Grove, Pa.) secondary Ab were used.

Example 3

In Utero Electroporation

In utero electroporation (IUE) was performed exactly as described (Saito and Nakatsuji, 2001; Tabata and Nakajima, 2001). Briefly, CD1 mice (gestational day 13.5) were anesthetized with an i.p. injection of ketamine/xylazine mixture. Endotoxin-free plasmid DNA (1 µl total volume containing either 2 µg of a single plasmid or 1 µg each of two plasmids) was injected through the uterus into the targeted brain regions of embryos using pulled glass capillaries (Drummond Scientific). Voltage pulses (37V, 50 msec; BTX Square Wave gene pulser) are generally delivered into the embryo by holding the embryo in parallel along its anterior-posterior axis through the uterus with forceps-type electrodes.

Example 4

Bromodeoxyuridine (BrdU) Treatment and Immunohistochemistry

Embryonic brains positively transfected based on the fluorescent protein expression were harvested 40 h later and fixed in 4% PFA in 0.1 M phosphate buffer overnight at 4° C. For adult brain harvest, animals were perfused with 4% PFA (Chuang et al., 2001; Dedesma et al., 2006). Coronal sections of 40 µm were cut on a Leica vibratome (Leica, Nussloch, Germany). Immunostaining was carried out by using a free floating method previously described (Chuang et al., 2001) except an antigen retrieval procedure was incorporated for Tbr1 and Tbr2 detection (Hevner et al., 2001). Immunolabeling of GFP and DsRed were used routinely to detect the reporter proteins in electroporated brain slices. Negative controls (e.g., omitting primary antibodies) did not give rise to specific signal in all studies. All immunolabeled samples were examined on a Leica confocal microscope. At least 3 mice were analyzed for each experiment. Statistical analysis was performed using GraphPad Prism 4.0b software (GraphPad Software, Inc).

For BrdU labeling, animals were injected with a single pulse of BrdU (100 μg/g body weight). The injections were repeated 3 times with 2-h intervals. Animals were perfused at survival time points of 1 h, 24 h, and 72 h after the last BrdU administration. Brains were sectioned, stained, and scored as described (Dedesma et al., 2006).

REFERENCES

Altman J, Das G D. 1965. Autoradiographic and histological evidence of postnatal hippocampal neurogenesis in rats. J Comp Neurol 124:319-335.
Barker N, et al (2007) Identification of stem cells in small intestine and colon by marker gene Lgr5. Nature 449(7165):1003-7
Barker N, et al (2009) Crypt stem cells as the cells-of-origin of intestinal cancer. Nature. 457(7229):608-11.
Brazel C Y, Limke T L, Osborne J K, Miura T, Cai J, Pevny L, Rao M S. 2005. Sox2 expression defines a heterogeneous population of neurosphere-forming cells in the adult murine brain. Aging Cell 4(4):197-207.
Cameron H A, Woolley C S, McEwen B S, Gould E. 1993. Differentiation of newly born neurons and glia in the dentate gyrus of the adult rat. Neuroscience 56:337-344.
Chuang J Z, Milner T A, Sung C H. 2001. Subunit heterogeneity of cytoplasmic dynein: Differential expression of 14 kDa dynein light chains in rat hippocampus. J Neurosci 21(15):5501-5512.
Chuang J Z, Yeh T Y, Bollati F, Conde C, Canavosio F, Caceres A, Sung C H. 2005. The dynein light chain Tctex-1 has a dynein-independent role in actin remodeling during neurite outgrowth. Dev Cell 9:75-86.
Couillard-Despres S, Winner B, Karl C, Lindemann G, Schmid P, Aigner R, Laemke J, Bogdahn U, Winkler J, Bischofberger J, Aigner L. 2006. Targeted transgene expression in neuronal precursors: watching young neurons in the old brain. Eur J Neurosci 24(6):1535-1545.
Dedesma C, Chuang J Z, Alfinito P D, Sung C H. 2006. Dynein light chain Tctex-1 identifies neural progenitors in adult brain. J Comp Neurol 496(6):773-786.
Duan X, Kang E, Liu C Y, Ming G L, Song H. 2008. Development of neural stem cell in the adult brain. Curr Opin Neurobiol 18(1):108-115.
Ehninger D, Kempermann G. 2008. Neurogenesis in the adult hippocampus. Cell Tissue Res 331(1):243-250.
Englund C, Fink A, Lau C, Pham D, Daza R A, Bulfone A, Kowalczyk T, Hevner R F. 2005. Pax6, Tbr2, and Tbr1 are expressed sequentially by radial glia, intermediate progenitor cells, and postmitotic neurons in developing neocortex. J Neurosci 25(1):247-251.
Eriksson P S, Perfilieva E, Bjork-Eriksson T, Alborn A M, Nordborg C, Peterson D A, Gage F H. 1998. Neurogenesis in the adult human hippocampus. Nat Med 4(11):1313-1317
Ever L, Gaiano N. 2005. Radial 'glial' progenitors: neurogenesis and signaling. Curr Opin Neurobiol 15(1):29-33.
Filippov V, Kronenberg G, Pivneva T, Reuter K, Steiner B, Wang L P, Yamaguchi M, Kettenmann H, Kempermann G. 2003. Subpopulation of nestin-expressing progenitor cells in the adult murine hippocampus shows electrophysiological and morphological characteristics of astrocytes. Mol Cell Neurosci 23(3):373-382.
Fukuda S, Kato F, Tozuka Y, Yamaguchi M, Miyamoto Y, Hisatsune T. 2003. Two distinct subpopulations of nestin-positive cells in adult mouse dentate gyrus. J Neurosci 23(28):9357-9366.
Gal J S, Morozov Y M, Ayoub A E, Chatterjee M, Rakic P, Haydar T F. 2006. Molecular and morphological heterogeneity of neural precursors in the mouse neocortical proliferative zones. J Neurosci 26(3):1045-1056.
Garcia A D, Doan N B, Imura T, Bush T G, Sofroniew M V. 2004. GFAP-expressing progenitors are the principal source of constitutive neurogenesis in adult mouse forebrain. Nat Neurosci 7(11):1233-1241.
Gotta M, Dong Y, Peterson Y K, Lanier S M, Ahringer J. 2003. Asymmetrically distributed C. elegans homologs of AGS3/PINS control spindle position in the early embryo. Curr Biol 13(12):1029-1037.
Gotz M, Stoykova A, Gruss P. 1998. Pax6 controls radial glia differentiation in the cerebral cortex. Neuron 21(5):1031-1044.
Hastings N B, Gould E. 1999. Rapid extension of axons into the CA3 region by adult-generated granule cells. J Comp Neurol 413(1):146-154.
Hevner R F, Shi L, Justice N, Hsueh Y, Sheng M, Smiga S, Bulfone A, Goffinet A M, Campagnoni A T, Rubenstein J L. 2001. Tbr1 regulates differentiation of the preplate and layer 6. Neuron 29(2):353-366.
Hodge R D, Kowalczyk T D, Wolf S A, Encinas J M, Rippey C, Enikolopov G, Kempermann G, Hevner R F. 2008. Intermediate progenitors in adult hippocampal neurogenesis: Tbr2 expression and coordinate regulation of neuronal output. J Neurosci 28(14):3707-3717.
Hogan B, Constantini F, Lacy E. 1986. Manipulating the Mouse Embryo: A Laboratory Manuel. N.Y.: Cold Spring Harbor.
Jessberger S, Romer B, Babu H, Kempermann G. 2005. Seizures induce proliferation and dispersion of doublecortin-positive hippocampal progenitor cells. Exp Neurol 196(2):342-351.
Kempermann G, Kuhn H G, Gage F H. 1998. Experience-induced neurogenesis in the senescent dentate gyrus. J Neurosci 18(9):3206-3212.
King S M, Dillman J Fr, Benashski S E, Lye R J, Patel-King R S, Pfister K K. 1996. The mouse t-complex-encoded protein Tctex-1 is a light chain of brain cytoplasmic dynein. J Biol Chem 271 (50):32281-32287.
Komitova M, Eriksson P S. 2004. Sox-2 is expressed by neural progenitors and astroglia in the adult rat brain. Neurosci Lett 369(1):24-27.
Kornack D R, Rakic P. 1999. Continuation of neurogenesis in the hippocampus of the adult macaque monkey. Proc Natl Acad Sci USA 96(10):5768-5773.
Kronenberg G, Reuter K, Steiner B, Brandt M D, Jessberger S, Yamaguchi M, Kempermann G. 2003. Subpopulations of proliferating cells of the adult hippocampus respond differently to physiologic neurogenic stimuli. J Comp Neurol 467(4):455-463.
Machado R D, Rudarakanchana N, Atkinson C, Flanagan J A, Harrison R, Morrell N W, Trembath R C. 2003. Functional interaction between BMPR-II and Tctex-1, a light chain of Dynein, is isoform-specific and disrupted by mutations underlying primary pulmonary hypertension. Hum Mol Genet 12(24):3277-3286.

Markakis E A, Gage F H. 1999. Adult-generated neurons in the dentate gyrus send axonal projections to field CA3 and are surrounded by synaptic vesicles. J Comp Neurol 406 (4):449-460.

Matsuda T, Cepko C L. 2004. INAUGURAL ARTICLE: Electroporation and RNA interference in the rodent retina in vivo and in vitro. Proc Natl Acad Sci USA 101(1):16-22.

Mignone J L, Kukekov V, Chiang A S, Steindler D, Enikolopov G. 2004. Neural stem and progenitor cells in nestin-GFP transgenic mice. J Comp Neurol 469(3):311-324.

Mills J C et al (2002) Molecular characterization of mouse gastric epithelial progenitor cells. PNAS 99(23): 14819-14824. (this has the microarray data showing tctex-1 is upregulated)

Mueller S, Cao X, Welker R, Wimmer E. 2002. Interaction of the poliovirus receptor CD155 with the dynein light chain Tctex-1 and its implication for poliovirus pathogenesis. J Biol Chem 277(10):7897-7904.

Nadano D, Nakayama J, Matsuzawa S, Sato T A, Matsuda T, Fukuda M N. 2002. Human tastin, a proline-rich cytoplasmic protein, associates with the microtubular cytoskeleton. Biochem J 364(Pt 3):669-677.

Nagano F, Orita S, Sasaki T, Naito A, Sakaguchi G, Maeda M, Watanabe T, Kominami E, Uchiyama Y, Takai Y. 1998. Interaction of Doc2 with tctex-1, a light chain of cytoplasmic dynein. Implication in dynein-dependent vesicle transport. J Biol Chem 273:30065-30068.

Palmer T D, Takahashi J, Gage F H. 1997. The adult rat hippocampus contains primordial neural stem cells. Mol Cell Neurosci 8(6):389-404.

Pfister K K, Fisher E M, Gibbons I R, Hays T S, Holzbaur E L, McIntosh J R, Porter M E, Schroer T A, Vaughan K T, Witman G B, King S M, Vallee R B. 2005. Cytoplasmic dynein nomenclature. J Cell Biol 171:411-413.

Roy N S, Benraiss A, Wang S, Fraser R A, Goodman R, Couldwell W T, Nedergaard M, Kawaguchi A, Okano H, Goldman S A. 2000a. Promoter-targeted selection and isolation of neural progenitor cells from the adult human ventricular zone. J Neurosci Res 59(3):321-331.

Roy N S, Wang S, Jiang L, Kang J, Benraiss A, Harrison-Restelli C, Fraser R A, Couldwell W T, Kawaguchi A, Okano H, Nedergaard M, Goldman S A. 2000b. In vitro neurogenesis by progenitor cells isolated from the adult human hippocampus. Nat Med 6:271-277.

Sachdev P, Menon S, Kastner D B, Chuang J Z, Yeh T Y, Conde C, Caceres A, Sung C H, Sakmar T P. 2007. G protein beta gamma subunit interaction with the dynein light-chain component Tctex-1 regulates neurite outgrowth. Embo J 26(11):2621-2632.

Saito T, Nakatsuji N. 2001. Efficient gene transfer into the embryonic mouse brain using in vivo electroporation. Dev Biol 240(1):237-246.

Sanada K, Tsai L H. 2005. G Protein betagamma Subunits and AGS3 Control Spindle Orientation and Asymmetric Cell Fate of Cerebral Cortical Progenitors. Cell 122(1): 119-131.

Schaefer M, Petronczki M, Dorner D, Forte M, Knoblich J A. 2001. Heterotrimeric G proteins direct two modes of asymmetric cell division in the Drosophila nervous system. Cell 107(2):183-194.

Schwarzer C, Barnikol-Watanabe S, Thinnes F P, Hilschmann N. 2002. Voltage-dependent anion-selective channel (VDAC) interacts with the dynein light chain Tctex1 and the heat-shock protein PBP74. Int J Biochem Cell Biol 34(9):1059-1070.

Seaberg R M, van der Kooy D. 2002. Adult rodent neurogenic regions: the ventricular subependyma contains neural stem cells, but the dentate gyrus contains restricted progenitors. J Neurosci 22(5):1784-1793.

Seri B, Garcia-Verdugo J M, Collado-Morente L, McEwen B S, Alvarez-Buylla A. 2004. Cell types, lineage, and architecture of the germinal zone in the adult dentate gyrus. J Comp Neurol 478(4):359-378.

Seri B, Garcia-Verdugo J M, McEwen B S, Alvarez-Buylla A. 2001. Astrocytes give rise to new neurons in the adult mammalian hippocampus. J Neurosci 21(18):7153-7160.

Steiner B, Klempin F, Wang L, Kott M, Kettenmann H, Kempermann G. 2006. Type-2 cells as link between glial and neuronal lineage in adult hippocampal neurogenesis. Glia 54(8):805-814.

Tabata H, Nakajima K. 2001. Efficient in utero gene transfer system to the developing mouse brain using electroporation: visualization of neuronal migration in the developing cortex. Neuroscience 103(4):865-872.

Tai A W, Chuang J-Z, Bode C, Wolfrum U, Sung C-H. 1999. Rhodopsin's carboxy-terminal cytoplasmic tail acts as a membrane receptor for cytoplasmic dynein by binding to the dynein light chain Tctex-1. Cell 97:877-887.

Tai A W, Chuang J-Z, Sung C-H. 2001. Cytoplasmic dynein regulation by subunit heterogeneity and its role in apical transport. J Cell Biol 153:1499-1509.

Takesono A, Cismowski M J, Ribas C, Bernard M, Chung P, Hazard S, 3rd, Duzic E, Lanier S M. 1999. Receptor-independent activators of heterotrimeric G-protein signaling pathways. J Biol Chem 274(47):33202-33205.

van Praag H, Schinder A F, Christie B R, Toni N, Palmer T D, Gage F H. 2002. Functional neurogenesis in the adult hippocampus. Nature 415(6875):1030-1034.

Wang S, Roy N S, Benraiss A, Goldman S A. 2000. Promoter-based isolation and fluorescence-activated sorting of mitotic neuronal progenitor cells from the adult mammalian ependymal/subependymal zone. Dev Neurosci 22(1-2): 167-176.

Wang S, Wu H, Jiang J, Delohery T M, Isdell F, Goldman S A. 1998. Isolation of neuronal precursors by sorting embryonic forebrain transfected with GFP regulated by the T alpha 1 tubulin promoter. Nat Biotechnol 16(2):196-201.

Wang X, Qiu R, Tsark W, Lu Q. 2007. Rapid promoter analysis in developing mouse brain and genetic labeling of young neurons by doublecortin-DsRed-express. J Neurosci Res 85(16):3567-3573.

Xu Y, Tamamaki N, Noda T, Kimura K, Itokazu Y, Matsumoto N, Dezawa M, Ide C. 2005. Neurogenesis in the ependymal layer of the adult rat 3rd ventricle. Exp Neurol 192(2):251-264.

Yamaguchi M, Saito H, Suzuki M, Mori K. 2000. Visualization of neurogenesis in the central nervous system using nestin promoter-GFP transgenic mice. Neuroreport 11(9): 1991-1996.

Zhao C, Deng W, Gage F H. 2008. Mechanisms and functional implications of adult neurogenesis. Cell 132(4):645-660.

What is claimed is:

1. A vector comprising a nucleic acid encoding a Tctex-1 promoter operably linked to a heterologous nucleic acid, said promoter comprising the nucleotide sequence set forth in SEQ ID NO: 1 or SEQ ID NO: 2.

2. The vector of claim 1, wherein said nucleic acid of interest encodes a marker gene.

3. The vector of claim 1, wherein said nucleic acid of interest encodes an effector nucleic acid.

4. The vector of claim 1, wherein said nucleic acid of interest encodes a protein of interest.

5. A host cell comprising a vector of any one of claims 1-4.

6. A pharmaceutical composition comprising a vector of any one of claims 1-4.

7. A pharmaceutical composition comprising the host cell of claim 5.

8. A kit comprising a vector of any one of claims 1-4.

* * * * *